United States Patent
Berelsman et al.

(10) Patent No.: US 9,918,826 B2
(45) Date of Patent: Mar. 20, 2018

(54) SCAFFOLD FOR SPRING LIGAMENT REPAIR

(71) Applicant: Biomet Sports Medicine, LLC, Warsaw, IN (US)

(72) Inventors: Brian K. Berelsman, Warsaw, IN (US); Mark S. Myerson, Baltimore, MD (US); Kevin T. Stone, Winona Lake, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 585 days.

(21) Appl. No.: 14/095,614

(22) Filed: Dec. 3, 2013

(65) Prior Publication Data

US 2014/0094913 A1    Apr. 3, 2014

Related U.S. Application Data

(60) Continuation-in-part of application No. 14/055,191, filed on Oct. 16, 2013, now Pat. No. 9,539,003, which
(Continued)

(51) Int. Cl.
*A61B 17/04* (2006.01)
*A61F 2/08* (2006.01)
(Continued)

(52) U.S. Cl.
CPC ........ *A61F 2/0811* (2013.01); *A61B 17/0401* (2013.01); *A61B 17/06166* (2013.01);
(Continued)

(58) Field of Classification Search
CPC ............ A61B 17/0401; A61B 17/1714; A61B 17/1764; A61B 2017/06185; A61F 2/08; A61F 2/0805; A61F 2/0811; A61F 2002/0817; A61F 2002/0835; A61F 2002/0847; A61F 2002/0852; A61F 2002/0858; A61F 2002/0864;
(Continued)

(56) References Cited

U.S. PATENT DOCUMENTS 65,499 A    6/1867  Miller
126,366 A   4/1872  Wills
(Continued)

FOREIGN PATENT DOCUMENTS

AU    4957264    3/1966
AU    440266    10/1967
(Continued)

OTHER PUBLICATIONS

US 6,238,418, 05/2001, Schwartz et al. (withdrawn)
(Continued)

*Primary Examiner* — Dianne Dornbusch
(74) *Attorney, Agent, or Firm* — Schwegman Lundberg & Woessner, P.A.

(57) ABSTRACT

A construct is disclosed that may be used to repair or replace a natural ligament. The construct may be formed of materials for biocompatibility and/or resorbtion. The construct may be provided or connected to a soft anchor for connection to a bone portion.

25 Claims, 7 Drawing Sheets

Related U.S. Application Data is a division of application No. 13/098,897, filed on May 2, 2011, now Pat. No. 8,562,645, which is a continuation-in-part of application No. 12/702,067, filed on Feb. 8, 2010, now Pat. No. 8,672,968, which is a continuation of application No. 11/541,505, filed on Sep. 29, 2006, now Pat. No. 7,658,751, application No. 14/095,614, filed on Dec. 3, 2013, which is a continuation-in-part of application No. 12/719,337, filed on Mar. 8, 2010, now Pat. No. 9,078,644, which is a continuation-in-part of application No. 12/489,168, filed on Jun. 22, 2009, now Pat. No. 8,361,113, which is a continuation-in-part of application No. 12/474,802, filed on May 29, 2009, now Pat. No. 8,088,130, which is a continuation-in-part of application No. 12/196,405, filed on Aug. 22, 2008, now Pat. No. 8,128,658, and a continuation-in-part of application No. 12/196,407, filed on Aug. 22, 2008, now Pat. No. 8,137,382, and a continuation-in-part of application No. 12/196,410, filed on Aug. 22, 2008, now Pat. No. 8,118,836, and a continuation-in-part of application No. 11/541,506, filed on Sep. 29, 2006, now Pat. No. 7,601,165.

(60) Provisional application No. 61/783,976, filed on Mar. 14, 2013.

(51) Int. Cl.
   *A61B 17/06* (2006.01)
   *A61B 17/00* (2006.01)

(52) U.S. Cl.
   CPC ....... *A61B 17/0482* (2013.01); *A61B 17/0487* (2013.01); *A61B 2017/00858* (2013.01); *A61B 2017/0406* (2013.01); *A61B 2017/0417* (2013.01); *A61B 2017/0477* (2013.01); *A61B 2017/06185* (2013.01); *A61F 2002/0852* (2013.01); *A61F 2002/0882* (2013.01)

(58) Field of Classification Search
   CPC ........ A61F 2002/087; A61F 2002/0876; A61F 2002/0882; A61F 2002/0888
   See application file for complete search history.

(56) References Cited

U.S. PATENT DOCUMENTS

| | | | |
|---|---|---|---|
| 233,475 A | 10/1880 | Cook et al. | |
| 261,501 A | 7/1882 | Vandermark | |
| 268,407 A | 12/1882 | Hughes | |
| 330,087 A | 11/1885 | Binns | |
| 394,739 A | 12/1888 | Toulmin | |
| 401,677 A | 4/1889 | Autenrieth | |
| 417,805 A | 12/1889 | Beaman | |
| 487,304 A | 12/1892 | Todd | |
| 762,710 A | 6/1901 | Hall | |
| 837,767 A | 12/1906 | Aims | |
| 838,203 A | 12/1906 | Neil | |
| 1,059,631 A | 4/1913 | Popovics | |
| 1,131,155 A | 3/1915 | Murphy | |
| 1,153,450 A | 9/1915 | Schaff | |
| 1,346,940 A | 7/1920 | Collins | |
| 1,635,066 A | 7/1927 | Wells | |
| 1,950,799 A | 3/1934 | Jones | |
| 2,065,659 A | 12/1936 | Cullen | |
| 2,108,206 A | 2/1938 | Meeker | |
| 2,121,193 A | 6/1938 | Hanicke | |
| 2,242,003 A | 5/1941 | Lorenzo | |
| 2,267,925 A | 12/1941 | Johnston | |
| 2,302,986 A | 11/1942 | Vollrath | |
| 2,329,398 A | 9/1943 | Duffy | |
| 2,397,216 A | 3/1946 | Stellin | |
| RE22,857 E | 3/1947 | Ogburn | |
| 2,526,959 A | 10/1950 | Lorenzo | |
| 2,528,456 A | 10/1950 | Stevenson | |
| 2,562,419 A | 7/1951 | Ferris | |
| 2,581,564 A | 1/1952 | Villegas | |
| 2,600,395 A | 6/1952 | Domoj et al. | |
| 2,610,631 A | 9/1952 | Calicchio | |
| 2,665,597 A | 1/1954 | Hill | |
| 2,669,774 A | 2/1954 | Mitchell | |
| 2,698,986 A | 1/1955 | Brown | |
| 2,760,488 A | 8/1956 | Pierce | |
| 2,833,284 A | 5/1958 | Springer | |
| 2,846,712 A | 8/1958 | Markman | |
| 2,860,393 A | 11/1958 | Brock | |
| 2,880,728 A | 4/1959 | Rights | |
| 2,881,762 A | 4/1959 | Lowrie | |
| 2,883,096 A | 4/1959 | Dawson | |
| 2,913,042 A | 11/1959 | Taylor | |
| 2,947,504 A * | 8/1960 | Ruhlman | H01B 17/22 174/173 |
| 3,000,009 A | 9/1961 | Selstad | |
| 3,003,155 A | 10/1961 | Mielzynski et al. | |
| 3,013,559 A | 12/1961 | Thomas | |
| 3,037,619 A | 6/1962 | Stevans | |
| 3,039,460 A | 6/1962 | Chandler | |
| 3,081,781 A | 3/1963 | Stermer | |
| 3,090,386 A | 5/1963 | Curtis | |
| 3,103,666 A | 9/1963 | Bone | |
| 3,123,077 A | 3/1964 | Alcamo | |
| 3,125,095 A | 3/1964 | Kaufman et al. | |
| 3,209,422 A | 10/1965 | Dritz | |
| 3,234,938 A | 2/1966 | Robinson | |
| 3,240,379 A | 3/1966 | Bremer et al. | |
| 3,250,271 A | 5/1966 | Lippes | |
| 3,399,432 A | 9/1968 | Merser | |
| 3,409,014 A | 11/1968 | Shannon | |
| RE26,501 E | 12/1968 | Himmelstein et al. | |
| 3,435,475 A | 4/1969 | Bisk | |
| 3,467,089 A | 9/1969 | Hasson | |
| 3,470,834 A | 10/1969 | Bone | |
| 3,470,875 A | 10/1969 | Johnson | |
| 3,500,820 A | 3/1970 | Almen | |
| 3,507,274 A | 4/1970 | Soichet | |
| 3,513,484 A | 5/1970 | Hausner | |
| 3,515,132 A | 6/1970 | McKnight | |
| 3,522,803 A | 8/1970 | Majzlin | |
| 3,527,223 A | 9/1970 | Shein | |
| 3,533,406 A | 10/1970 | Hutterer et al. | |
| 3,541,591 A | 11/1970 | Hoegerman | |
| 3,545,008 A * | 12/1970 | Bader, Jr. | A61F 2/08 128/DIG. 21 |
| 3,547,389 A | 12/1970 | Mitchell | |
| 3,579,831 A | 5/1971 | Stevens et al. | |
| 3,590,616 A | 7/1971 | Schussler | |
| 3,608,095 A | 9/1971 | Barry | |
| 3,618,447 A | 11/1971 | Goins | |
| 3,628,530 A | 12/1971 | Schwartz | |
| 3,643,649 A | 2/1972 | Amato | |
| 3,648,705 A | 3/1972 | Lary | |
| 3,650,274 A | 3/1972 | Edwards et al. | |
| 3,656,483 A | 4/1972 | Rudel | |
| 3,659,597 A | 5/1972 | Wolfers | |
| 3,664,345 A | 5/1972 | Dabbs et al. | |
| 3,665,560 A | 5/1972 | Bennett et al. | |
| 3,675,639 A | 7/1972 | Cimber | |
| 3,683,422 A | 8/1972 | Stemmer et al. | |
| 3,692,022 A | 9/1972 | Ewing | |
| 3,695,271 A | 10/1972 | Chodorow | |
| 3,699,969 A | 10/1972 | Allen | |
| 3,716,058 A | 2/1973 | Tanner, Jr. | |
| 3,744,488 A | 7/1973 | Cox | |
| 3,752,516 A | 8/1973 | Mumma | |
| 3,757,629 A | 9/1973 | Schneider | |
| 3,763,856 A | 10/1973 | Blomberg | |
| 3,771,520 A | 11/1973 | Lerner | |
| 3,777,748 A | 12/1973 | Abramson | |
| 3,807,407 A | 4/1974 | Schweizer | |
| 3,810,456 A | 5/1974 | Karman | |

(56) References Cited

U.S. PATENT DOCUMENTS

| | | |
|---|---|---|
| 3,825,010 A | 7/1974 | McDonald |
| 3,840,017 A | 10/1974 | Violante et al. |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,877,570 A | 4/1975 | Barry |
| 3,880,156 A | 4/1975 | Hoff |
| 3,881,475 A | 5/1975 | Gordon et al. |
| 3,889,666 A | 6/1975 | Lerner |
| 3,892,240 A | 7/1975 | Park |
| 3,896,500 A | 7/1975 | Rambert et al. |
| 3,907,442 A | 9/1975 | Reid |
| 3,910,281 A | 10/1975 | Kletschka et al. |
| 3,918,444 A | 11/1975 | Hoff et al. |
| 3,918,455 A | 11/1975 | Coplan |
| 3,927,666 A | 12/1975 | Hoff |
| 3,931,667 A | 1/1976 | Merser et al. |
| 3,933,153 A | 1/1976 | Csatary et al. |
| 3,937,217 A | 2/1976 | Kosonen et al. |
| 3,943,932 A | 3/1976 | Woo |
| 3,946,446 A | 3/1976 | Schofield |
| 3,946,728 A | 3/1976 | Bettex |
| 3,946,740 A | 3/1976 | Bassett |
| 3,953,896 A | 5/1976 | Treace |
| 3,954,103 A | 5/1976 | Garcia-Roel et al. |
| 3,961,632 A | 6/1976 | Moossun |
| 3,973,560 A | 8/1976 | Emmett et al. |
| 3,976,079 A | 8/1976 | Samuels et al. |
| 3,977,050 A | 8/1976 | Perez et al. |
| 3,979,799 A | 9/1976 | Merser et al. |
| 3,985,138 A | 10/1976 | Jarvik |
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |
| 4,013,071 A | 3/1977 | Rosenberg et al. |
| 4,026,281 A | 5/1977 | Mayberry et al. |
| 4,036,101 A | 7/1977 | Burnett |
| 4,050,100 A | 9/1977 | Barry |
| 4,054,954 A | 10/1977 | Nakayama et al. |
| 4,084,478 A | 4/1978 | Simmons |
| 4,085,466 A | 4/1978 | Goodfellow et al. |
| 4,094,313 A | 6/1978 | Komamura et al. |
| 4,099,750 A | 7/1978 | McGrew |
| 4,103,690 A | 8/1978 | Harris |
| RE29,819 E | 10/1978 | Bone |
| 4,121,487 A | 10/1978 | Bone |
| 4,143,656 A | 3/1979 | Holmes et al. |
| 4,144,876 A | 3/1979 | DeLeo |
| 4,146,022 A | 3/1979 | Johnson et al. |
| 4,149,277 A | 4/1979 | Bokros |
| 4,157,714 A | 6/1979 | Foltz et al. |
| 4,158,250 A | 6/1979 | Ringwald |
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert et al. |
| 4,185,636 A | 1/1980 | Gabbay et al. |
| 4,196,883 A | 4/1980 | Einhorn et al. |
| 4,210,148 A | 7/1980 | Stivala |
| 4,235,161 A | 11/1980 | Kunreuther |
| 4,235,238 A | 11/1980 | Ogiu et al. |
| 4,237,779 A | 12/1980 | Kunreuther |
| 4,243,037 A | 1/1981 | Smith |
| 4,249,525 A | 2/1981 | Krzeminski |
| 4,263,913 A | 4/1981 | Malmin |
| 4,265,246 A | 5/1981 | Barry |
| 4,273,117 A | 6/1981 | Neuhauser et al. |
| 4,275,490 A | 6/1981 | Bivins |
| 4,275,717 A | 6/1981 | Bolesky |
| 4,287,807 A | 9/1981 | Pacharis et al. |
| 4,291,698 A | 9/1981 | Fuchs et al. |
| 4,301,551 A | 11/1981 | Dore et al. |
| 4,307,723 A | 12/1981 | Finney |
| 4,312,337 A | 1/1982 | Donohue |
| 4,316,469 A | 2/1982 | Kapitanov et al. |
| 4,326,531 A | 4/1982 | Shimonaka et al. |
| 4,345,601 A | 8/1982 | Fukuda |
| 4,349,027 A | 9/1982 | DiFrancesco |
| 4,388,921 A | 6/1983 | Sutter et al. |
| 4,400,833 A | 8/1983 | Kurland |
| 4,402,445 A | 9/1983 | Green |
| 4,409,974 A | 10/1983 | Freedland |
| 4,438,769 A | 3/1984 | Pratt et al. |
| 4,441,489 A | 4/1984 | Evans et al. |
| 4,454,875 A | 6/1984 | Pratt et al. |
| 4,462,395 A | 7/1984 | Johnson |
| 4,463,753 A | 8/1984 | Gustilo |
| 4,473,102 A | 9/1984 | Ohman et al. |
| 4,484,570 A | 11/1984 | Sutter et al. |
| 4,489,446 A | 12/1984 | Reed |
| 4,489,464 A | 12/1984 | Massari et al. |
| 4,493,323 A | 1/1985 | Albright et al. |
| 4,496,468 A | 1/1985 | House et al. |
| 4,505,274 A | 3/1985 | Speelman |
| 4,509,516 A | 4/1985 | Richmond |
| 4,531,522 A | 7/1985 | Bedi et al. |
| 4,532,926 A | 8/1985 | O'Holla |
| 4,534,350 A | 8/1985 | Golden et al. |
| 4,535,764 A | 8/1985 | Ebert |
| 4,537,185 A | 8/1985 | Stednitz |
| 4,549,545 A | 10/1985 | Levy |
| 4,549,652 A | 10/1985 | Free |
| 4,561,432 A | 12/1985 | Mazor |
| 4,564,007 A | 1/1986 | Coombs et al. |
| 4,570,623 A | 2/1986 | Ellison et al. |
| 4,573,844 A | 3/1986 | Smith |
| 4,576,608 A | 3/1986 | Homsy |
| 4,584,722 A | 4/1986 | Levy et al. |
| 4,587,963 A | 5/1986 | Leibinger et al. |
| 4,590,928 A | 5/1986 | Hunt et al. |
| 4,595,007 A | 6/1986 | Mericle |
| 4,596,249 A | 6/1986 | Freda et al. |
| 4,602,635 A | 7/1986 | Mulhollan et al. |
| 4,602,636 A | 7/1986 | Noiles |
| 4,604,997 A | 8/1986 | De Bastiani et al. |
| 4,605,414 A | 8/1986 | Czajka |
| 4,616,650 A | 10/1986 | Green et al. |
| 4,621,640 A | 11/1986 | Mulhollan et al. |
| 4,624,254 A | 11/1986 | McGarry et al. |
| 4,632,100 A | 12/1986 | Somers et al. |
| 4,635,637 A | 1/1987 | Schreiber |
| 4,636,121 A | 1/1987 | Miller |
| 4,640,271 A | 2/1987 | Lower |
| 4,641,652 A | 2/1987 | Hutterer et al. |
| 4,649,916 A | 3/1987 | Frimberger |
| 4,649,952 A | 3/1987 | Jobe |
| 4,653,486 A | 3/1987 | Coker |
| 4,653,487 A | 3/1987 | Maale |
| 4,653,489 A | 3/1987 | Tronzo |
| 4,655,777 A | 4/1987 | Dunn et al. |
| 4,662,068 A | 5/1987 | Polonsky |
| 4,667,662 A | 5/1987 | Titone et al. |
| 4,667,675 A | 5/1987 | Davis |
| 4,669,473 A | 6/1987 | Richards et al. |
| 4,683,895 A | 8/1987 | Pohndorf |
| 4,688,561 A | 8/1987 | Reese |
| 4,690,169 A | 9/1987 | Jobe |
| 4,696,300 A | 9/1987 | Anderson |
| 4,705,040 A | 11/1987 | Mueller et al. |
| 4,708,132 A | 11/1987 | Silvestrini |
| 4,714,475 A | 12/1987 | Grundei et al. |
| 4,716,893 A | 1/1988 | Fischer et al. |
| 4,719,671 A | 1/1988 | Ito et al. |
| 4,719,917 A | 1/1988 | Barrows et al. |
| 4,723,540 A | 2/1988 | Gilmer, Jr. |
| 4,724,839 A | 2/1988 | Bedi et al. |
| 4,728,332 A | 3/1988 | Albrektsson |

(56) References Cited

U.S. PATENT DOCUMENTS

| | | |
|---|---|---|
| 4,736,746 A | 4/1988 | Anderson |
| 4,738,255 A | 4/1988 | Goble et al. |
| 4,739,751 A | 4/1988 | Sapega et al. |
| 4,741,330 A | 5/1988 | Hayhurst |
| 4,741,336 A | 5/1988 | Failla et al. |
| 4,744,353 A | 5/1988 | McFarland |
| 4,744,793 A | 5/1988 | Parr et al. |
| 4,750,492 A | 6/1988 | Jacobs |
| 4,751,922 A | 6/1988 | Dipietropolo |
| 4,760,843 A | 8/1988 | Fischer et al. |
| 4,760,844 A | 8/1988 | Kyle |
| 4,760,848 A | 8/1988 | Hasson |
| 4,770,663 A | 9/1988 | Hanslik et al. |
| 4,772,261 A | 9/1988 | Von Hoff et al. |
| 4,772,286 A | 9/1988 | Goble et al. |
| 4,773,910 A | 9/1988 | Chen et al. |
| 4,775,380 A | 10/1988 | Seedhom et al. |
| 4,776,328 A | 10/1988 | Frey et al. |
| 4,781,190 A | 11/1988 | Lee et al. |
| 4,784,126 A | 11/1988 | Hourahane |
| 4,787,882 A | 11/1988 | Claren et al. |
| 4,790,297 A | 12/1988 | Luque et al. |
| 4,790,850 A | 12/1988 | Dunn et al. |
| 4,793,363 A | 12/1988 | Ausherman et al. |
| 4,809,695 A | 3/1989 | Gwathmey et al. |
| 4,813,406 A | 3/1989 | Ogle, II |
| 4,823,794 A | 4/1989 | Pierce |
| 4,828,562 A | 5/1989 | Kenna |
| 4,832,026 A | 5/1989 | Jones |
| 4,834,098 A | 5/1989 | Jones |
| 4,838,282 A | 6/1989 | Strasser et al. |
| 4,841,960 A | 6/1989 | Garner |
| 4,851,005 A | 7/1989 | Hunt et al. |
| 4,858,603 A | 8/1989 | Clemow et al. |
| 4,858,608 A | 8/1989 | McQuilkin et al. |
| 4,860,513 A | 8/1989 | Whitman |
| 4,863,383 A | 9/1989 | Grafelmann et al. |
| 4,870,957 A | 10/1989 | Goble et al. |
| 4,873,976 A | 10/1989 | Schreiber |
| 4,884,572 A | 12/1989 | Bays et al. |
| 4,887,601 A | 12/1989 | Richards |
| 4,889,110 A | 12/1989 | Galline et al. |
| 4,890,615 A | 1/1990 | Caspari et al. |
| 4,893,619 A | 1/1990 | Dale et al. |
| 4,893,974 A | 1/1990 | Fischer et al. |
| 4,895,148 A | 1/1990 | Bays et al. |
| 4,896,668 A | 1/1990 | Popoff et al. |
| 4,898,156 A | 2/1990 | Gatturna et al. |
| 4,899,743 A | 2/1990 | Nicholson et al. |
| 4,901,721 A | 2/1990 | Hakki |
| 4,922,897 A | 5/1990 | Sapega et al. |
| 4,923,461 A | 5/1990 | Caspari et al. |
| 4,927,421 A | 5/1990 | Goble et al. |
| 4,946,377 A | 8/1990 | Kovach |
| 4,946,468 A | 8/1990 | Li |
| 4,950,270 A | 8/1990 | Bowman et al. |
| 4,950,285 A | 8/1990 | Wilk |
| 4,960,381 A | 10/1990 | Niznick |
| 4,961,741 A | 10/1990 | Hayhurst |
| 4,968,315 A | 11/1990 | Gatturna |
| 4,968,317 A | 11/1990 | Tormala et al. |
| 4,969,886 A | 11/1990 | Cziffer et al. |
| 4,974,488 A | 12/1990 | Spralja |
| 4,976,736 A | 12/1990 | White et al. |
| 4,978,350 A | 12/1990 | Wagenknecht et al. |
| 4,979,956 A | 12/1990 | Silvestrini |
| 4,983,176 A | 1/1991 | Cushman et al. |
| 4,988,351 A | 1/1991 | Paulos et al. |
| 4,994,074 A | 2/1991 | Bezwada et al. |
| 4,997,433 A | 3/1991 | Goble et al. |
| 5,002,550 A | 3/1991 | Li |
| 5,002,562 A | 3/1991 | Oberlander |
| 5,002,574 A | 3/1991 | May et al. |
| 5,007,921 A | 4/1991 | Brown |
| 5,020,713 A | 6/1991 | Kunreuther |
| 5,026,398 A * | 6/1991 | May ................. A61F 2/08 606/151 |
| 5,030,224 A | 7/1991 | Wright et al. |
| 5,030,235 A | 7/1991 | Campbell, Jr. |
| 5,035,701 A | 7/1991 | Kabbara |
| 5,037,422 A | 8/1991 | Hayhurst et al. |
| 5,037,426 A | 8/1991 | Goble et al. |
| 5,041,129 A | 8/1991 | Hayhurst et al. |
| 5,046,513 A | 9/1991 | Gatturna et al. |
| 5,047,030 A | 9/1991 | Draenert et al. |
| 5,053,046 A | 10/1991 | Janese |
| 5,053,047 A | 10/1991 | Yoon |
| 5,059,201 A | 10/1991 | Asnis |
| 5,059,206 A | 10/1991 | Winters |
| 5,061,277 A | 10/1991 | Carpentier et al. |
| 5,062,344 A | 11/1991 | Gerker |
| 5,062,843 A | 11/1991 | Mahony, III |
| 5,064,431 A | 11/1991 | Gilbertson et al. |
| 5,071,420 A | 12/1991 | Paulos et al. |
| 5,074,874 A | 12/1991 | Yoon et al. |
| 5,078,731 A | 1/1992 | Hayhurst |
| 5,078,843 A | 1/1992 | Pratt |
| 5,084,050 A | 1/1992 | Draenert |
| 5,084,058 A | 1/1992 | Li |
| 5,085,661 A | 2/1992 | Moss |
| 5,087,263 A | 2/1992 | Li |
| 5,087,309 A | 2/1992 | Melton, Jr. |
| 5,089,012 A | 2/1992 | Prou |
| 5,092,866 A | 3/1992 | Breard et al. |
| 5,098,433 A | 3/1992 | Freedland |
| 5,098,435 A | 3/1992 | Stednitz et al. |
| 5,100,415 A | 3/1992 | Hayhurst |
| 5,100,417 A | 3/1992 | Cerier et al. |
| 5,108,433 A | 4/1992 | May et al. |
| 5,116,337 A | 5/1992 | Johnson |
| 5,116,373 A | 5/1992 | Jakob et al. |
| 5,116,375 A | 5/1992 | Hofmann |
| 5,123,913 A | 6/1992 | Wilk et al. |
| 5,123,914 A | 6/1992 | Cope |
| 5,127,785 A | 7/1992 | Faucher et al. |
| 5,129,901 A | 7/1992 | Decoste |
| 5,129,902 A | 7/1992 | Goble et al. |
| 5,129,904 A | 7/1992 | Illi et al. |
| 5,129,906 A | 7/1992 | Ross et al. |
| 5,139,498 A | 8/1992 | Astudillo Ley |
| 5,139,499 A | 8/1992 | Small et al. |
| 5,139,520 A | 8/1992 | Rosenberg |
| 5,143,498 A | 9/1992 | Whitman |
| 5,147,362 A | 9/1992 | Goble |
| 5,149,329 A | 9/1992 | Richardson |
| 5,151,104 A | 9/1992 | Kenna |
| 5,152,790 A | 10/1992 | Rosenberg et al. |
| 5,154,189 A | 10/1992 | Oberlander |
| 5,156,616 A | 10/1992 | Meadows et al. |
| 5,163,960 A | 11/1992 | Bonutti |
| D331,626 S | 12/1992 | Hayhurst et al. |
| 5,169,400 A | 12/1992 | Muhling et al. |
| 5,171,274 A | 12/1992 | Fluckiger et al. |
| 5,176,682 A | 1/1993 | Chow |
| 5,178,629 A | 1/1993 | Kammerer |
| 5,183,458 A | 2/1993 | Marx |
| 5,190,545 A | 3/1993 | Corsi et al. |
| 5,192,282 A | 3/1993 | Draenert et al. |
| 5,197,987 A | 3/1993 | Koch et al. |
| 5,199,135 A | 4/1993 | Gold |
| 5,203,784 A | 4/1993 | Ross et al. |
| 5,203,787 A | 4/1993 | Noblitt et al. |
| 5,207,679 A | 5/1993 | Li |
| 5,209,753 A | 5/1993 | Biedermann et al. |
| 5,209,805 A | 5/1993 | Spraggins |
| 5,211,647 A | 5/1993 | Schmieding |
| 5,211,650 A | 5/1993 | Noda |
| 5,214,987 A | 6/1993 | Fenton, Sr. |
| 5,219,359 A | 6/1993 | McQuilkin et al. |
| 5,222,976 A | 6/1993 | Yoon |
| 5,224,946 A | 7/1993 | Hayhurst et al. |
| 5,230,699 A | 7/1993 | Grasinger |
| 5,232,436 A | 8/1993 | Janevski |
| 5,234,435 A | 8/1993 | Seagrave, Jr. |

(56) References Cited

U.S. PATENT DOCUMENTS

| | | |
|---|---|---|
| 5,235,238 A | 8/1993 | Nomura et al. |
| 5,236,445 A | 8/1993 | Hayhurst et al. |
| 5,236,461 A | 8/1993 | Forte |
| 5,242,447 A | 9/1993 | Borzone |
| 5,246,441 A | 9/1993 | Ross et al. |
| 5,249,899 A | 10/1993 | Wilson |
| 5,250,053 A | 10/1993 | Snyder |
| 5,258,015 A | 11/1993 | Li et al. |
| 5,258,016 A | 11/1993 | DiPoto et al. |
| 5,258,040 A | 11/1993 | Bruchman et al. |
| 5,261,908 A | 11/1993 | Campbell, Jr. |
| 5,268,001 A | 12/1993 | Nicholson et al. |
| 5,269,160 A | 12/1993 | Wood |
| 5,269,783 A | 12/1993 | Sander |
| 5,269,806 A | 12/1993 | Sardelis et al. |
| 5,269,809 A | 12/1993 | Hayhurst et al. |
| 5,279,311 A | 1/1994 | Snyder |
| 5,281,422 A | 1/1994 | Badylak et al. |
| 5,282,809 A | 2/1994 | Kammerer et al. |
| 5,282,832 A | 2/1994 | Toso et al. |
| 5,282,867 A | 2/1994 | Mikhail |
| 5,285,040 A | 2/1994 | Brandberg et al. |
| 5,290,217 A | 3/1994 | Campos |
| 5,290,243 A | 3/1994 | Chodorow et al. |
| 5,306,301 A | 4/1994 | Graf et al. |
| 5,312,410 A | 5/1994 | Miller et al. |
| 5,312,422 A | 5/1994 | Trott |
| 5,312,438 A | 5/1994 | Johnson |
| 5,314,429 A | 5/1994 | Goble |
| 5,318,566 A | 6/1994 | Miller |
| 5,318,575 A | 6/1994 | Chesterfield et al. |
| 5,318,577 A | 6/1994 | Li |
| 5,318,578 A | 6/1994 | Hasson |
| 5,320,115 A | 6/1994 | Kenna |
| 5,320,626 A | 6/1994 | Schmieding |
| 5,320,633 A | 6/1994 | Allen et al. |
| 5,324,308 A | 6/1994 | Pierce |
| 5,330,489 A | 7/1994 | Green et al. |
| 5,333,625 A | 8/1994 | Klein |
| 5,334,204 A | 8/1994 | Clewett et al. |
| 5,336,229 A | 8/1994 | Noda |
| 5,336,231 A | 8/1994 | Adair |
| 5,336,240 A | 8/1994 | Metzler et al. |
| 5,339,870 A | 8/1994 | Green et al. |
| 5,342,369 A | 8/1994 | Harryman, II |
| 5,346,462 A | 9/1994 | Barber |
| 5,350,380 A | 9/1994 | Goble et al. |
| RE34,762 E | 10/1994 | Goble et al. |
| 5,354,292 A | 10/1994 | Braeuer et al. |
| 5,354,298 A | 10/1994 | Lee et al. |
| 5,356,412 A | 10/1994 | Golds et al. |
| 5,356,413 A | 10/1994 | Martins et al. |
| 5,356,417 A | 10/1994 | Golds |
| 5,358,511 A | 10/1994 | Gatturna et al. |
| 5,360,431 A | 11/1994 | Puno et al. |
| 5,362,294 A | 11/1994 | Seitzinger |
| 5,364,400 A | 11/1994 | Rego, Jr. et al. |
| 5,366,461 A | 11/1994 | Blasnik |
| 5,368,599 A | 11/1994 | Hirsch et al. |
| 5,370,646 A | 12/1994 | Reese et al. |
| 5,370,661 A | 12/1994 | Branch |
| 5,370,662 A | 12/1994 | Stone et al. |
| 5,372,146 A | 12/1994 | Branch |
| 5,372,604 A | 12/1994 | Trott |
| 5,372,821 A | 12/1994 | Badylak et al. |
| 5,374,268 A | 12/1994 | Sander |
| 5,374,269 A | 12/1994 | Rosenberg |
| 5,379,492 A | 1/1995 | Glesser |
| 5,383,878 A | 1/1995 | Roger et al. |
| 5,383,904 A | 1/1995 | Totakura et al. |
| 5,385,567 A | 1/1995 | Goble |
| 5,391,171 A | 2/1995 | Schmieding |
| 5,391,176 A | 2/1995 | de la Torre |
| 5,391,182 A | 2/1995 | Chin |
| 5,393,302 A | 2/1995 | Clark et al. |
| RE34,871 E | 3/1995 | McGuire et al. |
| 5,395,374 A | 3/1995 | Miller et al. |
| 5,397,356 A | 3/1995 | Goble et al. |
| 5,403,328 A | 4/1995 | Shallman |
| 5,403,329 A | 4/1995 | Hinchcliffe |
| 5,403,348 A | 4/1995 | Bonutti |
| 5,405,359 A | 4/1995 | Pierce |
| 5,411,550 A | 5/1995 | Herweck et al. |
| 5,415,658 A | 5/1995 | Kilpela et al. |
| 5,417,690 A | 5/1995 | Sennett et al. |
| 5,417,691 A | 5/1995 | Hayhurst |
| 5,417,698 A | 5/1995 | Green et al. |
| 5,417,712 A | 5/1995 | Whittaker et al. |
| 5,423,819 A | 6/1995 | Small et al. |
| 5,423,821 A | 6/1995 | Pasque |
| 5,423,823 A | 6/1995 | Schmieding |
| 5,423,824 A | 6/1995 | Akerfeldt et al. |
| 5,423,860 A | 6/1995 | Lizardi et al. |
| 5,425,733 A | 6/1995 | Schmieding |
| 5,425,766 A | 6/1995 | Bowald et al. |
| 5,433,751 A | 7/1995 | Christel et al. |
| 5,437,680 A | 8/1995 | Yoon |
| 5,437,685 A | 8/1995 | Blasnik |
| 5,439,684 A | 8/1995 | Prewett et al. |
| 5,441,508 A | 8/1995 | Gazielly et al. |
| 5,443,468 A | 8/1995 | Johnson |
| 5,443,482 A | 8/1995 | Stone et al. |
| 5,443,483 A | 8/1995 | Kirsch et al. |
| 5,443,509 A | 8/1995 | Boucher et al. |
| 5,445,833 A | 8/1995 | Badylak et al. |
| 5,447,512 A | 9/1995 | Wilson et al. |
| 5,449,361 A | 9/1995 | Preissman |
| 5,451,203 A | 9/1995 | Lamb |
| 5,454,811 A | 10/1995 | Huebner |
| 5,454,821 A | 10/1995 | Harm et al. |
| 5,456,685 A | 10/1995 | Huebner |
| 5,456,721 A | 10/1995 | Legrand |
| 5,456,722 A | 10/1995 | McLeod et al. |
| 5,458,601 A | 10/1995 | Young, Jr. et al. |
| 5,458,604 A | 10/1995 | Schmieding |
| 5,462,542 A | 10/1995 | Alesi, Jr. |
| 5,462,560 A | 10/1995 | Stevens |
| 5,464,426 A | 11/1995 | Bonutti |
| 5,464,427 A | 11/1995 | Curtis et al. |
| 5,464,440 A | 11/1995 | Johansson et al. |
| 5,466,237 A | 11/1995 | Byrd, III et al. |
| 5,467,786 A | 11/1995 | Allen et al. |
| 5,470,334 A | 11/1995 | Ross et al. |
| 5,470,337 A | 11/1995 | Moss |
| 5,470,338 A | 11/1995 | Whitfield et al. |
| 5,472,452 A | 12/1995 | Trott |
| 5,474,565 A | 12/1995 | Trott |
| 5,474,568 A | 12/1995 | Scott |
| 5,474,572 A | 12/1995 | Hayhurst |
| 5,476,465 A | 12/1995 | Preissman |
| 5,478,344 A | 12/1995 | Stone et al. |
| 5,478,345 A | 12/1995 | Stone et al. |
| 5,480,403 A | 1/1996 | Lee et al. |
| 5,480,406 A | 1/1996 | Nolan et al. |
| 5,484,442 A | 1/1996 | Melker et al. |
| 5,486,197 A | 1/1996 | Le et al. |
| 5,489,210 A | 2/1996 | Hanosh |
| 5,490,750 A | 2/1996 | Gundy |
| 5,495,974 A | 3/1996 | Deschenes et al. |
| 5,496,331 A | 3/1996 | Xu et al. |
| 5,496,348 A | 3/1996 | Bonutti |
| 5,500,000 A | 3/1996 | Feagin et al. |
| 5,505,735 A | 4/1996 | Li |
| 5,505,736 A | 4/1996 | Reimels et al. |
| 5,507,754 A | 4/1996 | Green et al. |
| 5,520,691 A | 5/1996 | Branch |
| 5,520,694 A | 5/1996 | Dance et al. |
| 5,520,700 A | 5/1996 | Beyar et al. |
| 5,520,702 A | 5/1996 | Sauer et al. |
| 5,522,817 A | 6/1996 | Sander et al. |
| 5,522,820 A | 6/1996 | Caspari et al. |
| 5,522,843 A | 6/1996 | Zang |
| 5,522,844 A | 6/1996 | Johnson |
| 5,522,845 A | 6/1996 | Wenstrom, Jr. |

(56) References Cited

U.S. PATENT DOCUMENTS

| | | |
|---|---|---|
| 5,522,846 A | 6/1996 | Bonutti |
| 5,524,946 A | 6/1996 | Thompson |
| 5,527,321 A | 6/1996 | Hinchliffe |
| 5,527,342 A | 6/1996 | Pietrzak et al. |
| 5,527,343 A | 6/1996 | Bonutti |
| 5,531,759 A | 7/1996 | Kensey et al. |
| 5,534,012 A | 7/1996 | Bonutti |
| 5,536,270 A | 7/1996 | Songer et al. |
| 5,540,698 A | 7/1996 | Preissman |
| 5,540,703 A | 7/1996 | Barker, Jr. et al. |
| 5,540,718 A | 7/1996 | Bartlett |
| 5,545,168 A | 8/1996 | Burke |
| 5,545,178 A | 8/1996 | Kensey et al. |
| 5,545,180 A | 8/1996 | Le et al. |
| 5,545,228 A | 8/1996 | Kambin |
| 5,549,613 A | 8/1996 | Goble et al. |
| 5,549,617 A | 8/1996 | Green et al. |
| 5,549,619 A | 8/1996 | Peters et al. |
| 5,549,630 A | 8/1996 | Bonutti |
| 5,549,631 A | 8/1996 | Bonutti |
| 5,562,668 A | 10/1996 | Johnson |
| 5,562,669 A | 10/1996 | McGuire |
| 5,562,683 A | 10/1996 | Chan |
| 5,562,685 A | 10/1996 | Mollenauer et al. |
| 5,562,686 A | 10/1996 | Sauer et al. |
| 5,569,269 A | 10/1996 | Hart et al. |
| 5,569,305 A | 10/1996 | Bonutti |
| 5,569,306 A | 10/1996 | Thal |
| 5,570,706 A | 11/1996 | Howell |
| 5,571,090 A | 11/1996 | Sherts |
| 5,571,104 A | 11/1996 | Li |
| 5,571,139 A | 11/1996 | Jenkins, Jr. |
| 5,572,655 A | 11/1996 | Tuljapurkar et al. |
| 5,573,286 A | 11/1996 | Rogozinski |
| 5,573,542 A | 11/1996 | Stevens |
| 5,573,547 A | 11/1996 | LeVeen et al. |
| 5,573,548 A | 11/1996 | Nazre et al. |
| 5,577,299 A | 11/1996 | Thompson et al. |
| 5,578,057 A | 11/1996 | Wenstrom, Jr. |
| 5,584,695 A | 12/1996 | Lal Sachdeva et al. |
| 5,584,835 A | 12/1996 | Greenfield |
| 5,584,836 A | 12/1996 | Ballintyn et al. |
| 5,584,862 A | 12/1996 | Bonutti |
| 5,586,986 A | 12/1996 | Hinchliffe |
| 5,588,575 A | 12/1996 | Davignon |
| 5,591,180 A | 1/1997 | Hinchliffe |
| 5,591,181 A | 1/1997 | Stone et al. |
| 5,591,207 A | 1/1997 | Coleman |
| 5,593,407 A | 1/1997 | Reis et al. |
| 5,593,425 A | 1/1997 | Bonutti et al. |
| 5,601,557 A | 2/1997 | Hayhurst |
| 5,601,559 A | 2/1997 | Melker et al. |
| 5,601,571 A | 2/1997 | Moss |
| 5,603,716 A | 2/1997 | Morgan et al. |
| 5,607,429 A | 3/1997 | Hayano et al. |
| 5,607,430 A | 3/1997 | Bailey |
| 5,613,971 A | 3/1997 | Lower et al. |
| 5,618,290 A | 4/1997 | Toy et al. |
| 5,626,611 A | 5/1997 | Liu et al. |
| 5,626,614 A | 5/1997 | Hart |
| 5,628,756 A | 5/1997 | Barker, Jr. et al. |
| 5,628,766 A | 5/1997 | Johnson |
| 5,630,824 A | 5/1997 | Hart |
| 5,632,748 A | 5/1997 | Beck, Jr. et al. |
| 5,641,256 A | 6/1997 | Gundy |
| 5,643,266 A | 7/1997 | Li |
| 5,643,269 A | 7/1997 | Harle et al. |
| 5,643,273 A | 7/1997 | Clark |
| 5,643,295 A | 7/1997 | Yoon |
| 5,643,319 A | 7/1997 | Green et al. |
| 5,643,320 A | 7/1997 | Lower et al. |
| 5,643,321 A | 7/1997 | McDevitt |
| 5,645,546 A | 7/1997 | Fard |
| 5,645,547 A | 7/1997 | Coleman |
| 5,645,568 A | 7/1997 | Chervitz et al. |
| 5,645,588 A | 7/1997 | Graf et al. |
| 5,647,874 A | 7/1997 | Hayhurst |
| 5,649,959 A | 7/1997 | Hannam et al. |
| 5,649,960 A | 7/1997 | Pavletic |
| 5,649,963 A | 7/1997 | McDevitt |
| 5,658,289 A | 8/1997 | Boucher et al. |
| 5,658,299 A | 8/1997 | Hart |
| 5,658,313 A | 8/1997 | Thal |
| 5,662,658 A | 9/1997 | Wenstrom, Jr. |
| 5,662,663 A | 9/1997 | Shallman |
| 5,662,681 A | 9/1997 | Nash et al. |
| 5,665,112 A | 9/1997 | Thal |
| 5,667,513 A | 9/1997 | Torrie et al. |
| 5,671,695 A | 9/1997 | Schroeder |
| 5,674,224 A | 10/1997 | Howell et al. |
| 5,679,723 A | 10/1997 | Cooper et al. |
| 5,681,334 A | 10/1997 | Evans et al. |
| 5,681,352 A | 10/1997 | Clancy, III et al. |
| 5,683,404 A | 11/1997 | Johnson |
| 5,683,419 A | 11/1997 | Thal |
| 5,688,284 A | 11/1997 | Chervitz et al. |
| 5,688,285 A | 11/1997 | Yamada et al. |
| 5,690,655 A | 11/1997 | Hart et al. |
| 5,690,676 A | 11/1997 | DiPoto et al. |
| 5,690,678 A | 11/1997 | Johnson |
| 5,693,046 A | 12/1997 | Songer et al. |
| 5,695,497 A | 12/1997 | Stahelin et al. |
| 5,697,929 A | 12/1997 | Mellinger |
| 5,699,657 A * | 12/1997 | Paulson ............... B65H 69/06 28/142 |
| 5,702,397 A | 12/1997 | Goble et al. |
| 5,702,422 A | 12/1997 | Stone |
| 5,702,462 A | 12/1997 | Oberlander |
| 5,707,373 A | 1/1998 | Sevrain et al. |
| 5,709,708 A | 1/1998 | Thal |
| 5,711,969 A | 1/1998 | Patel et al. |
| 5,713,005 A | 1/1998 | Proebsting |
| 5,713,897 A | 2/1998 | Goble et al. |
| 5,713,904 A | 2/1998 | Errico et al. |
| 5,713,905 A | 2/1998 | Goble et al. |
| 5,713,921 A | 2/1998 | Bonutti |
| 5,715,578 A | 2/1998 | Knudson |
| 5,716,359 A | 2/1998 | Ojima et al. |
| 5,716,397 A | 2/1998 | Myers |
| 5,718,717 A | 2/1998 | Bonutti |
| 5,720,747 A | 2/1998 | Burke |
| 5,720,765 A | 2/1998 | Thal |
| 5,720,766 A | 2/1998 | Zang et al. |
| 5,722,976 A | 3/1998 | Brown |
| 5,725,529 A | 3/1998 | Nicholson et al. |
| 5,725,549 A | 3/1998 | Lam |
| 5,725,556 A | 3/1998 | Moser et al. |
| 5,725,557 A | 3/1998 | Gatturna et al. |
| 5,725,581 A | 3/1998 | Brånemark |
| 5,725,582 A | 3/1998 | Bevan et al. |
| 5,726,722 A | 3/1998 | Uehara et al. |
| 5,728,107 A | 3/1998 | Zlock et al. |
| 5,728,109 A | 3/1998 | Schulze et al. |
| 5,728,136 A | 3/1998 | Thal |
| 5,733,293 A | 3/1998 | Scirica et al. |
| 5,733,306 A | 3/1998 | Bonutti |
| 5,733,307 A | 3/1998 | Dinsdale |
| 5,735,875 A | 4/1998 | Bonutti et al. |
| 5,741,259 A | 4/1998 | Chan |
| 5,741,260 A | 4/1998 | Songer et al. |
| 5,741,281 A | 4/1998 | Martin et al. |
| 5,743,912 A | 4/1998 | Lahille et al. |
| 5,746,751 A | 5/1998 | Sherts |
| 5,746,752 A | 5/1998 | Burkhart |
| 5,746,754 A | 5/1998 | Chan |
| 5,749,898 A | 5/1998 | Schulze et al. |
| 5,755,729 A | 5/1998 | de la Torre et al. |
| 5,755,791 A | 5/1998 | Whitson et al. |
| 5,766,176 A | 6/1998 | Duncan |
| 5,766,218 A | 6/1998 | Arnott |
| 5,766,250 A | 6/1998 | Chervitz et al. |
| 5,769,894 A | 6/1998 | Ferragamo |
| 5,769,899 A | 6/1998 | Schwartz et al. |
| 5,772,673 A | 6/1998 | Cuny et al. |

(56) References Cited

U.S. PATENT DOCUMENTS

| | | | |
|---|---|---|---|
| 5,776,196 A | 7/1998 | Matsuzaki et al. |
| 5,782,845 A | 7/1998 | Shewchuk |
| 5,782,862 A | 7/1998 | Bonutti |
| 5,782,864 A | 7/1998 | Lizardi |
| 5,782,866 A | 7/1998 | Wenstrom, Jr. |
| 5,785,714 A | 7/1998 | Morgan et al. |
| 5,792,142 A | 8/1998 | Galitzer |
| 5,792,149 A | 8/1998 | Sherts et al. |
| 5,796,127 A | 8/1998 | Hayafuji et al. |
| 5,797,913 A | 8/1998 | Dambreville et al. |
| 5,797,915 A | 8/1998 | Pierson, III et al. |
| 5,797,916 A | 8/1998 | McDowell |
| 5,797,928 A | 8/1998 | Kogasaka |
| 5,800,407 A | 9/1998 | Eldor et al. |
| 5,800,543 A * | 9/1998 | McLeod ............... A61F 2/08 623/13.19 |
| 5,810,824 A | 9/1998 | Chan |
| 5,810,848 A | 9/1998 | Hayhurst |
| 5,814,056 A | 9/1998 | Prosst et al. |
| 5,814,069 A | 9/1998 | Schulze et al. |
| 5,814,070 A | 9/1998 | Borzone et al. |
| 5,814,071 A | 9/1998 | Mcdevitt et al. |
| 5,814,072 A | 9/1998 | Bonutti |
| 5,814,073 A | 9/1998 | Bonutti |
| 5,823,980 A | 10/1998 | Kopfer |
| 5,824,011 A | 10/1998 | Stone et al. |
| 5,824,066 A | 10/1998 | Gross |
| 5,830,234 A | 11/1998 | Wojciechowicz et al. |
| 5,836,955 A | 11/1998 | Buelna et al. |
| 5,843,084 A | 12/1998 | Hart et al. |
| 5,845,645 A | 12/1998 | Bonutti |
| 5,846,254 A | 12/1998 | Schulze et al. |
| 5,848,983 A | 12/1998 | Basaj et al. |
| 5,849,012 A | 12/1998 | Abboudi |
| 5,860,973 A | 1/1999 | Michelson |
| 5,860,978 A | 1/1999 | McDevitt et al. |
| 5,868,740 A | 2/1999 | LeVeen et al. |
| 5,868,748 A | 2/1999 | Burke |
| 5,868,789 A | 2/1999 | Huebner |
| 5,871,484 A | 2/1999 | Spievack et al. |
| 5,871,486 A | 2/1999 | Huebner et al. |
| 5,871,490 A | 2/1999 | Schulze et al. |
| 5,885,294 A | 3/1999 | Pedlick et al. |
| 5,891,168 A | 4/1999 | Thal |
| 5,893,592 A | 4/1999 | Schulze et al. |
| 5,895,395 A | 4/1999 | Yeung |
| 5,897,564 A | 4/1999 | Schulze et al. |
| 5,897,574 A | 4/1999 | Bonutti |
| 5,899,902 A | 5/1999 | Brown et al. |
| 5,899,938 A | 5/1999 | Sklar et al. |
| 5,908,421 A | 6/1999 | Beger et al. |
| 5,908,436 A | 6/1999 | Cuschieri et al. |
| 5,910,148 A | 6/1999 | Reimels et al. |
| 5,911,721 A | 6/1999 | Nicholson et al. |
| 5,918,604 A | 7/1999 | Whelan |
| 5,921,986 A | 7/1999 | Bonutti |
| 5,925,008 A | 7/1999 | Douglas |
| 5,928,231 A | 7/1999 | Klein et al. |
| 5,928,267 A | 7/1999 | Bonutti et al. |
| RE36,289 E | 8/1999 | Le et al. |
| 5,931,838 A | 8/1999 | Vito |
| 5,931,844 A | 8/1999 | Thompson et al. |
| 5,931,869 A | 8/1999 | Boucher et al. |
| 5,935,119 A | 8/1999 | Guy et al. |
| 5,935,129 A | 8/1999 | Mcdevitt et al. |
| 5,935,133 A | 8/1999 | Wagner et al. |
| 5,935,149 A | 8/1999 | Ek |
| 5,938,668 A | 8/1999 | Scirica et al. |
| 5,941,439 A | 8/1999 | Kammerer et al. |
| 5,941,900 A | 8/1999 | Bonutti |
| 5,944,739 A | 8/1999 | Zlock et al. |
| 5,946,783 A | 9/1999 | Plociennik et al. |
| 5,947,915 A | 9/1999 | Thibodo, Jr. |
| 5,947,982 A | 9/1999 | Duran |
| 5,947,999 A | 9/1999 | Groiso |
| 5,948,002 A | 9/1999 | Bonutti |
| 5,951,559 A | 9/1999 | Burkhart |
| 5,951,560 A | 9/1999 | Simon et al. |
| 5,954,747 A | 9/1999 | Clark |
| 5,957,953 A | 9/1999 | DiPoto et al. |
| 5,961,520 A | 10/1999 | Beck, Jr. et al. |
| 5,961,521 A | 10/1999 | Roger et al. |
| 5,961,524 A | 10/1999 | Crombie |
| 5,964,764 A | 10/1999 | West, Jr. et al. |
| 5,964,767 A | 10/1999 | Tapia et al. |
| 5,964,769 A | 10/1999 | Wagner et al. |
| 5,964,783 A | 10/1999 | Grafton et al. |
| 5,968,045 A | 10/1999 | Frazier |
| 5,968,047 A | 10/1999 | Reed |
| 5,968,077 A | 10/1999 | Wojciechowicz et al. |
| 5,970,697 A | 10/1999 | Jacobs et al. |
| 5,972,006 A | 10/1999 | Sciaino, Jr. |
| 5,976,125 A | 11/1999 | Graham |
| 5,976,127 A | 11/1999 | Lax |
| 5,980,473 A | 11/1999 | Korakianitis et al. |
| 5,980,524 A | 11/1999 | Justin et al. |
| 5,980,539 A | 11/1999 | Kontos |
| 5,980,548 A | 11/1999 | Evans et al. |
| 5,980,558 A | 11/1999 | Wiley |
| 5,980,559 A | 11/1999 | Bonutti |
| 5,989,252 A | 11/1999 | Fumex |
| 5,989,256 A | 11/1999 | Kuslich et al. |
| 5,989,282 A | 11/1999 | Bonutti |
| 5,993,452 A | 11/1999 | Vandewalle |
| 5,993,476 A | 11/1999 | Groiso |
| 5,997,542 A | 12/1999 | Burke |
| 5,997,552 A | 12/1999 | Person et al. |
| 5,997,575 A | 12/1999 | Whitson et al. |
| 6,001,100 A | 12/1999 | Sherman et al. |
| 6,001,106 A | 12/1999 | Ryan et al. |
| 6,007,538 A | 12/1999 | Levin |
| 6,007,567 A | 12/1999 | Bonutti |
| 6,010,525 A | 1/2000 | Bonutti et al. |
| 6,016,727 A | 1/2000 | Morgan |
| 6,019,767 A | 2/2000 | Howell |
| 6,022,352 A | 2/2000 | Vandewalle |
| 6,022,373 A | 2/2000 | Li |
| 6,024,758 A | 2/2000 | Thal |
| 6,027,523 A | 2/2000 | Schmieding |
| 6,030,410 A | 2/2000 | Zurbrugg |
| 6,033,429 A | 3/2000 | Magovern |
| 6,033,430 A | 3/2000 | Bonutti |
| 6,039,753 A | 3/2000 | Meislin |
| 6,041,485 A | 3/2000 | Pedlick et al. |
| 6,042,601 A | 3/2000 | Smith |
| 6,042,609 A | 3/2000 | Giordano et al. |
| 6,045,551 A | 4/2000 | Bonutti |
| 6,045,571 A | 4/2000 | Hill et al. |
| 6,045,572 A | 4/2000 | Johnson et al. |
| 6,045,573 A | 4/2000 | Wenstrom, Jr. et al. |
| 6,045,574 A | 4/2000 | Thal |
| 6,047,826 A | 4/2000 | Kalinski et al. |
| 6,048,343 A | 4/2000 | Mathis et al. |
| 6,051,006 A | 4/2000 | Shluzas et al. |
| 6,051,007 A | 4/2000 | Hogendijk et al. |
| 6,053,916 A | 4/2000 | Moore |
| 6,053,921 A | 4/2000 | Wagner et al. |
| 6,056,752 A | 5/2000 | Roger |
| 6,056,772 A | 5/2000 | Bonutti |
| 6,056,773 A | 5/2000 | Bonutti |
| 6,059,817 A | 5/2000 | Bonutti et al. |
| 6,059,818 A | 5/2000 | Johnson et al. |
| 6,062,344 A | 5/2000 | Okabe et al. |
| 6,066,173 A | 5/2000 | McKernan et al. |
| 6,068,648 A | 5/2000 | Cole et al. |
| 6,071,305 A | 6/2000 | Brown et al. |
| 6,074,403 A | 6/2000 | Nord |
| 6,077,277 A | 6/2000 | Mollenauer et al. |
| 6,077,292 A | 6/2000 | Bonutti |
| 6,080,185 A | 6/2000 | Johnson et al. |
| 6,086,591 A | 7/2000 | Bojarski |
| 6,086,592 A | 7/2000 | Rosenberg et al. |
| 6,086,608 A | 7/2000 | Ek et al. |
| 6,093,200 A | 7/2000 | Liu et al. |

(56) References Cited

U.S. PATENT DOCUMENTS

| | | |
|---|---|---|
| 6,096,060 A | 8/2000 | Fitts et al. |
| 6,099,527 A | 8/2000 | Hochschuler et al. |
| 6,099,530 A | 8/2000 | Simonian et al. |
| 6,099,568 A | 8/2000 | Simonian et al. |
| 6,102,934 A | 8/2000 | Li |
| 6,106,545 A | 8/2000 | Egan |
| 6,110,128 A | 8/2000 | Andelin et al. |
| 6,110,207 A | 8/2000 | Eichhorn et al. |
| 6,113,604 A | 9/2000 | Whittaker et al. |
| 6,117,160 A | 9/2000 | Bonutti |
| 6,117,162 A | 9/2000 | Schmieding et al. |
| 6,123,710 A | 9/2000 | Pinczewski et al. |
| 6,132,433 A | 10/2000 | Whelan |
| 6,132,437 A | 10/2000 | Omurtag et al. |
| 6,136,010 A | 10/2000 | Modesitt et al. |
| 6,139,565 A | 10/2000 | Stone et al. |
| RE36,974 E | 11/2000 | Bonutti |
| 6,143,017 A | 11/2000 | Thal |
| 6,146,406 A | 11/2000 | Shluzas et al. |
| 6,146,408 A | 11/2000 | Bartlett |
| 6,149,653 A | 11/2000 | Deslauriers |
| 6,149,669 A | 11/2000 | Li |
| 6,152,928 A | 11/2000 | Wenstrom, Jr. |
| 6,152,934 A | 11/2000 | Harper et al. |
| 6,152,936 A | 11/2000 | Christy et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,165,203 A | 12/2000 | Krebs |
| 6,168,598 B1 | 1/2001 | Martello |
| 6,168,628 B1 | 1/2001 | Huebner |
| 6,171,310 B1 | 1/2001 | Giordano et al. |
| 6,174,324 B1 | 1/2001 | Egan et al. |
| 6,179,840 B1 | 1/2001 | Bowman |
| 6,183,461 B1 | 2/2001 | Matsuura et al. |
| 6,187,025 B1 | 2/2001 | Machek |
| 6,190,401 B1 | 2/2001 | Green et al. |
| 6,190,411 B1 | 2/2001 | Lo et al. |
| 6,193,754 B1 | 2/2001 | Seedhom |
| 6,200,318 B1 | 3/2001 | Har-Shai et al. |
| 6,200,329 B1 | 3/2001 | Fung et al. |
| 6,200,330 B1 | 3/2001 | Benderev et al. |
| 6,203,556 B1 | 3/2001 | Evans et al. |
| 6,203,565 B1 | 3/2001 | Bonutti et al. |
| 6,203,572 B1 | 3/2001 | Johnson et al. |
| 6,206,883 B1 | 3/2001 | Tunc |
| 6,210,376 B1 | 4/2001 | Grayson |
| 6,214,007 B1 | 4/2001 | Anderson |
| 6,214,012 B1 | 4/2001 | Karpman et al. |
| 6,217,580 B1 | 4/2001 | Levin |
| 6,221,107 B1 | 4/2001 | Steiner et al. |
| 6,228,096 B1 | 5/2001 | Marchand |
| 6,231,592 B1 | 5/2001 | Bonutti et al. |
| 6,235,057 B1 | 5/2001 | Roger et al. |
| 6,238,395 B1 | 5/2001 | Bonutti |
| 6,241,734 B1 | 6/2001 | Scribner et al. |
| 6,241,747 B1 | 6/2001 | Ruff |
| 6,241,771 B1 | 6/2001 | Gresser et al. |
| 6,245,081 B1 | 6/2001 | Bowman et al. |
| 6,254,604 B1 | 7/2001 | Howell |
| 6,258,091 B1 | 7/2001 | Sevrain et al. |
| 6,267,766 B1 | 7/2001 | Burkhart |
| 6,269,716 B1 | 8/2001 | Amis |
| 6,270,518 B1 | 8/2001 | Pedlick et al. |
| 6,273,890 B1 | 8/2001 | Frazier |
| 6,280,474 B1 | 8/2001 | Cassidy et al. |
| 6,283,973 B1 | 9/2001 | Hubbard et al. |
| 6,283,996 B1 | 9/2001 | Chervitz et al. |
| 6,287,307 B1 | 9/2001 | Abboudi |
| 6,287,325 B1 | 9/2001 | Bonutti |
| 6,293,961 B2 | 9/2001 | Schwartz et al. |
| 6,296,659 B1 | 10/2001 | Foerster |
| 6,299,615 B1 | 10/2001 | Huebner |
| 6,302,888 B1 | 10/2001 | Mellinger et al. |
| 6,302,899 B1 | 10/2001 | Johnson et al. |
| 6,303,158 B1 | 10/2001 | Odgaard et al. |
| 6,306,156 B1 | 10/2001 | Clark |
| 6,306,158 B1 | 10/2001 | Bartlett |
| 6,306,159 B1 | 10/2001 | Schwartz et al. |
| 6,309,405 B1 | 10/2001 | Bonutti |
| 6,312,448 B1 | 11/2001 | Bonutti |
| 6,315,788 B1 | 11/2001 | Roby |
| 6,319,271 B1 | 11/2001 | Schwartz et al. |
| 6,328,758 B1 | 12/2001 | Tornier et al. |
| 6,334,064 B1 | 12/2001 | Fiddian-Green |
| 6,342,060 B1 | 1/2002 | Adams |
| 6,343,531 B2 | 2/2002 | Amis |
| 6,355,066 B1 | 3/2002 | Kim |
| 6,358,270 B1 | 3/2002 | Lemer |
| 6,364,897 B1 | 4/2002 | Bonutti |
| 6,368,322 B1 | 4/2002 | Luks et al. |
| 6,368,326 B1 | 4/2002 | Dakin et al. |
| 6,368,343 B1 | 4/2002 | Bonutti et al. |
| 6,371,124 B1 | 4/2002 | Whelan |
| 6,379,361 B1 | 4/2002 | Beck, Jr. et al. |
| 6,383,190 B1 | 5/2002 | Preissman |
| 6,383,199 B2 | 5/2002 | Carter et al. |
| 6,387,111 B1 | 5/2002 | Barber |
| 6,387,113 B1 | 5/2002 | Hawkins et al. |
| 6,387,129 B2 | 5/2002 | Rieser et al. |
| 6,391,030 B1 | 5/2002 | Wagner et al. |
| 6,398,785 B2 | 6/2002 | Carchidi et al. |
| 6,406,479 B1 | 6/2002 | Justin et al. |
| 6,409,743 B1 | 6/2002 | Fenton, Jr. |
| 6,413,260 B1 | 7/2002 | Berrevoets et al. |
| 6,423,073 B2 | 7/2002 | Bowman |
| 6,423,088 B1 | 7/2002 | Fenton, Jr. |
| 6,425,924 B1 | 7/2002 | Rousseau |
| 6,428,562 B2 | 8/2002 | Bonutti |
| 6,432,123 B2 | 8/2002 | Schwartz et al. |
| 6,436,123 B1 | 8/2002 | Magovern |
| 6,436,124 B1 | 8/2002 | Anderson et al. |
| 6,440,134 B1 | 8/2002 | Zaccherotti et al. |
| 6,440,136 B1 | 8/2002 | Gambale et al. |
| 6,447,516 B1 | 9/2002 | Bonutti |
| 6,451,030 B2 | 9/2002 | Li et al. |
| 6,454,768 B1 | 9/2002 | Jackson |
| 6,458,134 B1 | 10/2002 | Songer et al. |
| 6,461,373 B2 | 10/2002 | Wyman et al. |
| 6,464,690 B1 | 10/2002 | Castaneda et al. |
| 6,464,713 B2 | 10/2002 | Bonutti |
| 6,468,293 B2 | 10/2002 | Bonutti et al. |
| 6,471,707 B1 | 10/2002 | Miller et al. |
| 6,475,230 B1 | 11/2002 | Bonutti et al. |
| 6,478,753 B2 | 11/2002 | Reay-Young |
| 6,482,210 B1 | 11/2002 | Skiba et al. |
| 6,485,504 B1 | 11/2002 | Johnson et al. |
| 6,491,714 B1 | 12/2002 | Bennett |
| 6,497,901 B1 | 12/2002 | Royer |
| 6,500,184 B1 | 12/2002 | Chan et al. |
| 6,500,195 B2 | 12/2002 | Bonutti |
| RE37,963 E | 1/2003 | Thal |
| 6,503,267 B2 | 1/2003 | Bonutti et al. |
| 6,506,190 B1 | 1/2003 | Walshe |
| 6,508,820 B2 | 1/2003 | Bales |
| 6,508,821 B1 | 1/2003 | Schwartz et al. |
| 6,508,830 B2 | 1/2003 | Steiner |
| 6,511,498 B1 | 1/2003 | Fumex |
| 6,511,499 B2 | 1/2003 | Schmieding et al. |
| 6,514,274 B1 | 2/2003 | Boucher et al. |
| 6,517,542 B1 | 2/2003 | Papay et al. |
| 6,517,552 B1 | 2/2003 | Nord et al. |
| 6,517,564 B1 | 2/2003 | Grafton et al. |
| 6,517,578 B2 | 2/2003 | Hein |
| 6,517,579 B1 | 2/2003 | Paulos et al. |
| 6,520,964 B2 | 2/2003 | Tallarida et al. |
| 6,520,980 B1 | 2/2003 | Foerster |
| 6,524,317 B1 | 2/2003 | Ritchart et al. |
| 6,527,777 B2 | 3/2003 | Justin |
| 6,527,794 B1 | 3/2003 | McDevitt et al. |
| 6,527,795 B1 | 3/2003 | Lizardi |
| 6,533,795 B1 | 3/2003 | Tran et al. |
| 6,533,802 B2 | 3/2003 | Bojarski et al. |

(56) References Cited

U.S. PATENT DOCUMENTS

| | | |
|---|---|---|
| 6,537,319 B2 | 3/2003 | Whelan |
| 6,540,750 B2 | 4/2003 | Burkhart |
| 6,540,769 B1 | 4/2003 | Miller, III |
| 6,540,770 B1 | 4/2003 | Tornier et al. |
| 6,540,783 B1 | 4/2003 | Whittaker et al. |
| 6,543,094 B2 | 4/2003 | D'Addario |
| 6,544,281 B2 | 4/2003 | ElAttrache et al. |
| 6,547,564 B1 | 4/2003 | Hansson et al. |
| 6,547,778 B1 | 4/2003 | Sklar et al. |
| 6,547,800 B2 | 4/2003 | Foerster et al. |
| 6,551,330 B1 | 4/2003 | Bain et al. |
| 6,551,343 B1 | 4/2003 | Tormala et al. |
| 6,551,353 B1 | 4/2003 | Baker et al. |
| 6,553,802 B1 | 4/2003 | Jacob et al. |
| 6,554,830 B1 | 4/2003 | Chappius |
| 6,554,852 B1 | 4/2003 | Oberlander |
| 6,554,862 B2 | 4/2003 | Hays et al. |
| 6,558,389 B2 | 5/2003 | Clark et al. |
| 6,562,071 B2 | 5/2003 | Jarvinen et al. |
| 6,565,572 B2 | 5/2003 | Chappius |
| 6,565,573 B1 | 5/2003 | Ferrante et al. |
| 6,569,167 B1 | 5/2003 | Bobechko et al. |
| 6,569,186 B1 | 5/2003 | Winters et al. |
| 6,569,187 B1 | 5/2003 | Bonutti et al. |
| 6,572,635 B1 | 6/2003 | Bonutti |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,595,911 B2 | 7/2003 | LoVuolo |
| 6,599,289 B1 | 7/2003 | Bojarski et al. |
| 6,599,319 B2 | 7/2003 | Knudsen et al. |
| 6,605,096 B1 | 8/2003 | Ritchart |
| 6,607,548 B2 | 8/2003 | Pohjonen et al. |
| 6,610,064 B1 | 8/2003 | Goble et al. |
| 6,610,079 B1 | 8/2003 | Li et al. |
| 6,613,018 B2 | 9/2003 | Bagga et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 | 9/2003 | Berube et al. |
| 6,623,524 B2 | 9/2003 | Schmieding |
| 6,626,910 B1 | 9/2003 | Hugues |
| 6,626,919 B1 | 9/2003 | Swanstrom |
| 6,626,930 B1 | 9/2003 | Allen et al. |
| 6,629,977 B1 | 10/2003 | Wolf |
| 6,632,245 B2 | 10/2003 | Kim |
| 6,635,073 B2 | 10/2003 | Bonutti |
| 6,638,279 B2 | 10/2003 | Bonutti |
| 6,638,286 B1 | 10/2003 | Burbank et al. |
| 6,638,312 B2 | 10/2003 | Plouhar et al. |
| 6,641,596 B1 | 11/2003 | Lizardi |
| 6,641,597 B2 | 11/2003 | Burkhart et al. |
| 6,645,211 B2 | 11/2003 | Magana |
| 6,645,227 B2 | 11/2003 | Fallin et al. |
| 6,648,903 B1 | 11/2003 | Pierson, III |
| 6,648,921 B2 | 11/2003 | Anderson et al. |
| 6,652,450 B2 | 11/2003 | Neisz et al. |
| 6,652,560 B1 | 11/2003 | Gerke et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier et al. |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,666,877 B2 | 12/2003 | Morgan et al. |
| 6,669,707 B1 | 12/2003 | Swanstrom et al. |
| 6,679,889 B1 | 1/2004 | West, Jr. et al. |
| 6,682,533 B1 | 1/2004 | Dinsdale et al. |
| 6,682,549 B2 | 1/2004 | Bartlett |
| 6,685,728 B2 | 2/2004 | Sinnott et al. |
| 6,689,137 B2 | 2/2004 | Reed |
| 6,689,153 B1 | 2/2004 | Skiba |
| 6,689,154 B2 | 2/2004 | Bartlett |
| 6,692,499 B2 | 2/2004 | Tormala et al. |
| 6,692,516 B2 | 2/2004 | West, Jr. et al. |
| 6,695,852 B2 | 2/2004 | Gleason |
| 6,712,849 B2 | 3/2004 | Re et al. |
| 6,712,859 B2 | 3/2004 | Rousseau |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,736,799 B1 | 5/2004 | Erbe et al. |
| 6,737,053 B1 | 5/2004 | Goh et al. |
| 6,746,483 B1 | 6/2004 | Bojarski et al. |
| 6,752,810 B1 | 6/2004 | Gao et al. |
| 6,752,831 B2 | 6/2004 | Sybert et al. |
| 6,755,836 B1 | 6/2004 | Lewis |
| 6,755,868 B2 | 6/2004 | Rousseau |
| 6,761,722 B2 | 7/2004 | Cole et al. |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,779,701 B2 | 8/2004 | Bailly et al. |
| 6,780,190 B2 | 8/2004 | Maroney |
| 6,780,198 B1 | 8/2004 | Gregoire et al. |
| 6,793,595 B1 * | 9/2004 | Monnet ............... A63B 63/004 473/478 |
| 6,802,862 B1 | 10/2004 | Roger et al. |
| 6,808,502 B2 | 10/2004 | Nguyen et al. |
| 6,808,526 B1 | 10/2004 | Magerl et al. |
| 6,814,741 B2 | 11/2004 | Bowman et al. |
| 6,830,572 B2 | 12/2004 | McDevitt et al. |
| 6,833,005 B2 | 12/2004 | Mantas et al. |
| 6,840,953 B2 | 1/2005 | Martinek |
| 6,860,885 B2 | 3/2005 | Bonutti |
| 6,860,895 B1 | 3/2005 | Akerfeldt et al. |
| 6,863,671 B1 | 3/2005 | Strobel et al. |
| 6,872,040 B2 | 3/2005 | Deeg et al. |
| 6,872,210 B2 | 3/2005 | Hearn |
| 6,875,216 B2 | 4/2005 | Wolf |
| 6,884,249 B2 | 4/2005 | May et al. |
| 6,887,243 B2 | 5/2005 | Culbert |
| 6,887,259 B2 | 5/2005 | Lizardi |
| 6,887,271 B2 | 5/2005 | Justin et al. |
| 6,890,354 B2 | 5/2005 | Steiner et al. |
| 6,893,448 B2 | 5/2005 | O'Quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,905,513 B1 | 6/2005 | Metzger |
| 6,908,466 B1 | 6/2005 | Bonutti et al. |
| 6,916,292 B2 | 7/2005 | Morawski et al. |
| 6,916,321 B2 | 7/2005 | TenHuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,939,379 B2 | 9/2005 | Sklar |
| 6,949,102 B2 | 9/2005 | Andrews |
| 6,951,565 B2 | 10/2005 | Keane et al. |
| 6,966,887 B1 | 11/2005 | Chin |
| 6,966,916 B2 | 11/2005 | Kumar |
| 6,969,391 B1 | 11/2005 | Gazzani |
| 6,969,398 B2 | 11/2005 | Stevens et al. |
| 6,972,027 B2 | 12/2005 | Fallin et al. |
| 6,980,903 B2 | 12/2005 | Daniels et al. |
| 6,984,237 B2 | 1/2006 | Hatch et al. |
| 6,986,781 B2 | 1/2006 | Smith |
| 6,989,034 B2 | 1/2006 | Hammer et al. |

(56) References Cited

U.S. PATENT DOCUMENTS

| | | | |
|---|---|---|---|
| 6,994,719 B2 | 2/2006 | Grafton | |
| 6,994,725 B1 | 2/2006 | Goble | |
| 7,001,429 B2 | 2/2006 | Ferguson | |
| 7,004,959 B2 | 2/2006 | Bonutti | |
| 7,008,451 B2 | 3/2006 | Justin et al. | |
| 7,048,754 B2 | 5/2006 | Martin et al. | |
| 7,052,499 B2 | 5/2006 | Steger et al. | |
| 7,066,942 B2 | 6/2006 | Treace | |
| 7,066,944 B2 | 6/2006 | Laufer et al. | |
| 7,081,126 B2 | 7/2006 | McDevitt et al. | |
| 7,083,638 B2 | 8/2006 | Foerster | |
| 7,087,064 B1 | 8/2006 | Hyde | |
| 7,087,073 B2 | 8/2006 | Bonutti | |
| 7,097,654 B1 | 8/2006 | Freedland | |
| 7,101,395 B2 | 9/2006 | Tremulis et al. | |
| 7,105,010 B2 | 9/2006 | Hart et al. | |
| 7,112,221 B2 | 9/2006 | Harris | |
| 7,118,578 B2 | 10/2006 | West, Jr. et al. | |
| 7,118,583 B2 | 10/2006 | O'Quinn et al. | |
| 7,125,421 B2 | 10/2006 | Tremulis et al. | |
| 7,131,467 B2 | 11/2006 | Gao et al. | |
| 7,137,996 B2 | 11/2006 | Steiner et al. | |
| 7,141,066 B2 | 11/2006 | Steiner et al. | |
| 7,144,414 B2 | 12/2006 | Harvie et al. | |
| 7,153,127 B2 | 12/2006 | Struble et al. | |
| 7,153,307 B2 | 12/2006 | Scribner et al. | |
| 7,153,312 B1 | 12/2006 | Torrie et al. | |
| 7,153,327 B1 | 12/2006 | Metzger | |
| 7,160,285 B2 | 1/2007 | Sklar et al. | |
| 7,160,333 B2 | 1/2007 | Plouhar et al. | |
| 7,172,626 B1 | 2/2007 | Andrews | |
| 7,201,722 B2 | 4/2007 | Krueger | |
| 7,207,993 B1 | 4/2007 | Baldwin et al. | |
| 7,229,441 B2 | 6/2007 | Trieu et al. | |
| 7,255,675 B2 | 8/2007 | Gertner et al. | |
| 7,255,700 B2 | 8/2007 | Kaiser et al. | |
| 7,255,715 B2 | 8/2007 | Metzger | |
| 7,261,716 B2 | 8/2007 | Strobel et al. | |
| 7,264,634 B2 | 9/2007 | Schmieding | |
| 7,279,008 B2 | 10/2007 | Brown et al. | |
| 7,285,124 B2 | 10/2007 | Foerster | |
| 7,303,577 B1 | 12/2007 | Dean | |
| 7,306,417 B2 | 12/2007 | Dorstewitz | |
| 7,309,355 B2 | 12/2007 | Donnelly et al. | |
| 7,326,222 B2 | 2/2008 | Dreyfuss et al. | |
| 7,329,272 B2 | 2/2008 | Burkhart et al. | |
| 7,361,179 B2 | 4/2008 | Rousseau et al. | |
| 7,377,845 B2 | 5/2008 | Stewart et al. | |
| 7,390,329 B2 | 6/2008 | Westra et al. | |
| 7,390,332 B2 | 6/2008 | Selvitelli et al. | |
| 7,399,018 B1* | 7/2008 | Khachaturian | B66C 1/12 294/74 |
| 7,442,210 B2 | 10/2008 | Segal et al. | |
| 7,465,308 B2 | 12/2008 | Sikora et al. | |
| 7,468,074 B2 | 12/2008 | Caborn et al. | |
| 7,481,814 B1 | 1/2009 | Metzger | |
| 7,484,539 B1* | 2/2009 | Huang | D03D 3/02 139/384 R |
| 7,485,149 B1 | 2/2009 | White | |
| 7,494,506 B2 | 2/2009 | Brulez et al. | |
| D587,807 S | 3/2009 | Wolf et al. | |
| 7,500,983 B1 | 3/2009 | Kaiser et al. | |
| 7,513,910 B2 | 4/2009 | Buskirk et al. | |
| 7,517,357 B2 | 4/2009 | Abrams et al. | |
| 7,572,275 B2 | 8/2009 | Fallin et al. | |
| 7,572,298 B2 | 8/2009 | Roller et al. | |
| 7,578,825 B2 | 8/2009 | Huebner | |
| 7,585,311 B2 | 9/2009 | Green et al. | |
| 7,588,587 B2 | 9/2009 | Barbieri et al. | |
| 7,591,823 B2 | 9/2009 | Tipirneni | |
| 7,597,705 B2 | 10/2009 | Forsberg et al. | |
| 7,601,165 B2 | 10/2009 | Stone | |
| 7,604,636 B1 | 10/2009 | Walters et al. | |
| 7,608,092 B1 | 10/2009 | Schaffhausen | |
| 7,608,098 B1 | 10/2009 | Stone et al. | |
| 7,615,076 B2 | 11/2009 | Cauthen, III et al. | |
| 7,621,937 B2 | 11/2009 | Pipenhagen et al. | |
| 7,632,287 B2 | 12/2009 | Baker et al. | |
| 7,651,509 B2 | 1/2010 | Bojarski et al. | |
| 7,658,750 B2 | 2/2010 | Li | |
| 7,658,751 B2 | 2/2010 | Stone et al. | |
| 7,670,279 B2 | 3/2010 | Gertner | |
| 7,678,123 B2 | 3/2010 | Chanduszko | |
| 7,691,112 B2 | 4/2010 | Chanduszko et al. | |
| 7,695,493 B2 | 4/2010 | Saadat et al. | |
| 7,695,503 B1 | 4/2010 | Kaiser et al. | |
| 7,703,372 B1 | 4/2010 | Shakespeare | |
| 7,713,285 B1 | 5/2010 | Stone et al. | |
| 7,717,929 B2 | 5/2010 | Fallman | |
| 7,731,732 B2 | 6/2010 | Ken | |
| 7,736,364 B2 | 6/2010 | Stone | |
| 7,736,379 B2 | 6/2010 | Ewers et al. | |
| 7,749,250 B2 | 7/2010 | Stone et al. | |
| 7,758,594 B2 | 7/2010 | Lamson et al. | |
| 7,758,611 B2 | 7/2010 | Kato | |
| 7,762,942 B2 | 7/2010 | Neisz et al. | |
| 7,776,041 B1 | 8/2010 | Walters | |
| 7,790,945 B1 | 9/2010 | Watson, Jr. | |
| 7,803,173 B2 | 9/2010 | Burkhart et al. | |
| 7,819,895 B2 | 10/2010 | Ginn et al. | |
| 7,828,820 B2 | 11/2010 | Stone et al. | |
| 7,828,850 B2 | 11/2010 | Cauthen, III et al. | |
| 7,856,698 B2 | 12/2010 | Hays | |
| 7,857,830 B2 | 12/2010 | Stone et al. | |
| 7,867,252 B2 | 1/2011 | Criscuolo et al. | |
| 7,867,264 B2 | 1/2011 | McDevitt et al. | |
| 7,875,058 B2 | 1/2011 | Holmes, Jr. | |
| 7,878,058 B2 | 2/2011 | Blendinger et al. | |
| 7,887,586 B2 | 2/2011 | Linares | |
| 7,896,907 B2 | 3/2011 | Mcdevitt et al. | |
| 7,905,903 B2 | 3/2011 | Stone et al. | |
| 7,905,904 B2 | 3/2011 | Stone et al. | |
| 7,909,851 B2 | 3/2011 | Stone et al. | |
| 7,914,539 B2 | 3/2011 | Stone et al. | |
| 7,938,847 B2 | 5/2011 | Fanton et al. | |
| 7,951,198 B2 | 5/2011 | Sucec et al. | |
| 7,955,388 B2 | 6/2011 | Jensen et al. | |
| 7,959,650 B2 | 6/2011 | Kaiser et al. | |
| 7,976,565 B1 | 7/2011 | Meridew | |
| 7,981,140 B2 | 7/2011 | Burkhart | |
| 7,998,203 B2 | 8/2011 | Blum | |
| 8,034,090 B2 | 10/2011 | Stone et al. | |
| 8,062,334 B2 | 11/2011 | Green et al. | |
| 8,075,574 B2 | 12/2011 | May et al. | |
| 8,088,130 B2 | 1/2012 | Kaiser et al. | |
| 8,109,867 B2* | 2/2012 | Rosenblatt | A61F 2/0063 600/30 |
| 8,114,127 B2 | 2/2012 | West, Jr. | |
| 8,114,128 B2 | 2/2012 | Cauldwell et al. | |
| 8,118,835 B2 | 2/2012 | Weisel et al. | |
| 8,118,836 B2 | 2/2012 | Denham et al. | |
| 8,118,868 B2 | 2/2012 | May et al. | |
| 8,128,658 B2 | 3/2012 | Kaiser et al. | |
| 8,137,354 B2 | 3/2012 | Stone | |
| 8,137,382 B2 | 3/2012 | Denham et al. | |
| 8,162,997 B2 | 4/2012 | Struhl | |
| 8,167,906 B2 | 5/2012 | Cauldwell et al. | |
| 8,177,810 B2 | 5/2012 | Ferree | |
| 8,202,295 B2 | 6/2012 | Kaplan | |
| 8,202,318 B2 | 6/2012 | Willobee | |
| 8,221,454 B2 | 7/2012 | Schaffhausen | |
| 8,231,654 B2 | 7/2012 | Kaiser et al. | |
| 8,251,998 B2 | 8/2012 | Hoeppner et al. | |
| 8,252,022 B2 | 8/2012 | Holman et al. | |
| 8,273,106 B2 | 9/2012 | Stone et al. | |
| 8,292,921 B2 | 10/2012 | Stone et al. | |
| 8,298,262 B2 | 10/2012 | Stone et al. | |
| 8,298,284 B2 | 10/2012 | Cassani | |
| 8,303,604 B2 | 11/2012 | Stone et al. | |
| 8,317,825 B2 | 11/2012 | Stone | |
| 8,337,525 B2 | 12/2012 | Stone et al. | |
| 8,343,155 B2 | 1/2013 | Fisher et al. | |
| 8,343,227 B2 | 1/2013 | Metzger et al. | |
| 8,361,113 B2 | 1/2013 | Stone et al. | |

(56) References Cited

U.S. PATENT DOCUMENTS

| | | |
|---|---|---|
| 8,409,253 B2 | 4/2013 | Stone et al. |
| 8,486,114 B2 | 7/2013 | Gillard et al. |
| 8,500,818 B2 | 8/2013 | Metzger et al. |
| 8,506,597 B2 | 8/2013 | Kaiser et al. |
| 8,551,140 B2 | 10/2013 | Denham et al. |
| 8,562,645 B2 | 10/2013 | Stone et al. |
| 8,562,647 B2 | 10/2013 | Kaiser et al. |
| 8,574,235 B2 | 11/2013 | Stone |
| 8,579,944 B2 | 11/2013 | Holloway et al. |
| 8,597,327 B2 | 12/2013 | Stone et al. |
| 8,608,777 B2 | 12/2013 | Kaiser et al. |
| 8,632,566 B2 | 1/2014 | Olson |
| 8,632,569 B2 | 1/2014 | Stone et al. |
| 8,652,171 B2 | 2/2014 | Stone et al. |
| 8,652,172 B2 | 2/2014 | Denham et al. |
| 8,672,968 B2 | 3/2014 | Stone et al. |
| 8,672,969 B2 | 3/2014 | Stone et al. |
| 8,702,718 B2 | 4/2014 | Bhatnagar et al. |
| 8,721,650 B2 | 5/2014 | Fanton et al. |
| 8,721,684 B2 | 5/2014 | Denham et al. |
| 8,771,316 B2 | 7/2014 | Denham et al. |
| 8,771,352 B2 | 7/2014 | Conner et al. |
| 8,777,956 B2 | 7/2014 | Hoeppner et al. |
| 8,801,783 B2 | 8/2014 | Stone et al. |
| 8,808,374 B2 | 8/2014 | Eggli |
| 8,840,645 B2 | 9/2014 | Denham et al. |
| 8,900,314 B2 | 12/2014 | Metzger et al. |
| 8,926,613 B2 | 1/2015 | Kaiser et al. |
| 8,932,331 B2 | 1/2015 | Kaiser et al. |
| 8,936,621 B2 | 1/2015 | Denham et al. |
| 8,961,548 B2 | 2/2015 | Buser |
| 8,968,364 B2 | 3/2015 | Berelsman et al. |
| 8,998,949 B2 | 4/2015 | Stone et al. |
| 9,005,287 B2 | 4/2015 | Stone |
| 9,017,381 B2 | 4/2015 | Kaiser et al. |
| 9,023,058 B2 | 5/2015 | Jaramillo et al. |
| 9,078,644 B2 | 7/2015 | Stone |
| 9,149,267 B2 | 10/2015 | Norton et al. |
| 9,173,651 B2 | 11/2015 | Stone et al. |
| 9,198,673 B2 | 12/2015 | Stone |
| 9,216,078 B2 | 12/2015 | Conner et al. |
| 9,271,713 B2 | 3/2016 | Denham et al. |
| 9,271,826 B2 | 3/2016 | Eggli et al. |
| 9,289,285 B2 | 3/2016 | Eggli |
| 9,314,235 B2 | 4/2016 | Bojarski et al. |
| 9,314,241 B2 | 4/2016 | Stone et al. |
| 9,357,991 B2 | 6/2016 | Denham et al. |
| 9,357,992 B2 | 6/2016 | Stone et al. |
| 9,370,350 B2 | 6/2016 | Norton |
| 9,381,013 B2 | 7/2016 | Norton |
| 9,402,621 B2 | 8/2016 | Stone et al. |
| 9,408,599 B2 | 8/2016 | Kaiser et al. |
| 9,414,833 B2 | 8/2016 | Stone et al. |
| 9,414,925 B2 | 8/2016 | Metzger et al. |
| 9,468,433 B2 | 10/2016 | Denham et al. |
| 9,486,211 B2 | 11/2016 | Stone et al. |
| 9,492,158 B2 | 11/2016 | Stone et al. |
| 9,498,204 B2 | 11/2016 | Denham et al. |
| 9,504,460 B2 | 11/2016 | Stone et al. |
| 9,510,819 B2 | 12/2016 | Stone et al. |
| 9,510,821 B2 | 12/2016 | Denham et al. |
| 9,532,777 B2 | 1/2017 | Kaiser et al. |
| 9,538,998 B2 | 1/2017 | Stone et al. |
| 9,539,003 B2 | 1/2017 | Stone et al. |
| 9,561,025 B2 | 2/2017 | Stone et al. |
| 9,572,655 B2 | 2/2017 | Denham et al. |
| 9,603,591 B2 | 3/2017 | Denham et al. |
| 9,622,736 B2 | 4/2017 | Stone et al. |
| 9,642,661 B2 | 5/2017 | Stone et al. |
| 9,681,940 B2 | 6/2017 | Stone et al. |
| 9,724,090 B2 | 8/2017 | Kaiser et al. |
| 9,757,119 B2 | 9/2017 | Norton et al. |
| 9,763,656 B2 | 9/2017 | Stone et al. |
| 9,788,876 B2 | 10/2017 | Stone |
| 9,801,620 B2 | 10/2017 | Kaiser et al. |
| 9,801,708 B2 | 10/2017 | Denham et al. |
| 9,833,230 B2 | 12/2017 | Stone |
| 9,861,351 B2 | 1/2018 | Kaiser et al. |
| 2001/0002439 A1 | 5/2001 | Bonutti et al. |
| 2001/0010005 A1 | 7/2001 | Kammerer et al. |
| 2001/0014825 A1 | 8/2001 | Burke et al. |
| 2001/0019649 A1 | 9/2001 | Field et al. |
| 2001/0029387 A1 | 10/2001 | Wolf et al. |
| 2001/0037131 A1 | 11/2001 | Schmieding et al. |
| 2001/0037153 A1 | 11/2001 | Rockwood et al. |
| 2001/0041916 A1 | 11/2001 | Bonutti |
| 2001/0041937 A1 | 11/2001 | Rieser et al. |
| 2001/0041938 A1 | 11/2001 | Hein |
| 2001/0044627 A1 | 11/2001 | Justin |
| 2001/0044639 A1 | 11/2001 | Levinson |
| 2001/0047206 A1 | 11/2001 | Sklar et al. |
| 2001/0051815 A1 | 12/2001 | Esplin |
| 2001/0051816 A1 | 12/2001 | Enzerink et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013607 A1 | 1/2002 | Lemer |
| 2002/0013613 A1 | 1/2002 | ElAttrache et al. |
| 2002/0019649 A1 | 2/2002 | Sikora et al. |
| 2002/0029048 A1 | 3/2002 | Miller |
| 2002/0029066 A1 | 3/2002 | Foerster |
| 2002/0032465 A1 | 3/2002 | Lemer |
| 2002/0045902 A1 | 4/2002 | Bonutti |
| 2002/0052628 A1 | 5/2002 | Bowman |
| 2002/0055780 A1 | 5/2002 | Sklar |
| 2002/0058966 A1 | 5/2002 | Tormala et al. |
| 2002/0068254 A1 | 6/2002 | Campbell |
| 2002/0077659 A1 | 6/2002 | Johnson et al. |
| 2002/0091391 A1 | 7/2002 | Cole et al. |
| 2002/0099411 A1 | 7/2002 | Bartlett |
| 2002/0111653 A1 | 8/2002 | Foerster |
| 2002/0120270 A1 | 8/2002 | Trieu et al. |
| 2002/0120292 A1 | 8/2002 | Morgan |
| 2002/0123752 A1 | 9/2002 | Schultheiss et al. |
| 2002/0128654 A1 | 9/2002 | Steger et al. |
| 2002/0128684 A1 | 9/2002 | Foerster |
| 2002/0129820 A1 | 9/2002 | Ryan et al. |
| 2002/0143336 A1 | 10/2002 | Hearn |
| 2002/0147463 A1 | 10/2002 | Martinek |
| 2002/0156475 A1 | 10/2002 | Lerch et al. |
| 2002/0161401 A1 | 10/2002 | Steiner |
| 2002/0161439 A1 | 10/2002 | Strobel et al. |
| 2002/0165548 A1 | 11/2002 | Jutley |
| 2002/0165611 A1* | 11/2002 | Enzerink ............ A61F 2/08 623/13.11 |
| 2002/0169452 A1 | 11/2002 | Tormala et al. |
| 2002/0169477 A1 | 11/2002 | Demopulos et al. |
| 2002/0169478 A1 | 11/2002 | Schwartz et al. |
| 2002/0173788 A1 | 11/2002 | Bojarski et al. |
| 2002/0177853 A1 | 11/2002 | Chervitz et al. |
| 2002/0188298 A1 | 12/2002 | Chan |
| 2002/0193830 A1 | 12/2002 | Bonutti |
| 2003/0004545 A1 | 1/2003 | Burkhart et al. |
| 2003/0009235 A1 | 1/2003 | Manrique et al. |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0065391 A1 | 4/2003 | Re et al. |
| 2003/0065402 A1 | 4/2003 | Anderson et al. |
| 2003/0078585 A1 | 4/2003 | Johnson et al. |
| 2003/0078603 A1 | 4/2003 | Schaller et al. |
| 2003/0078617 A1 | 4/2003 | Schwartz et al. |
| 2003/0083662 A1 | 5/2003 | Middleton |
| 2003/0083694 A1 | 5/2003 | Miller |
| 2003/0088251 A1 | 5/2003 | Braun et al. |
| 2003/0088272 A1 | 5/2003 | Smith |
| 2003/0105477 A1 | 6/2003 | Schwartz et al. |
| 2003/0105489 A1 | 6/2003 | Eichhorn et al. |

(56) References Cited

U.S. PATENT DOCUMENTS

| | | |
|---|---|---|
| 2003/0114929 A1* | 6/2003 | Knudsen .............. A61F 2/08 623/13.19 |
| 2003/0120309 A1 | 6/2003 | Colleran et al. |
| 2003/0130670 A1 | 7/2003 | Anderson et al. |
| 2003/0130694 A1 | 7/2003 | Bojarski et al. |
| 2003/0130695 A1 | 7/2003 | McDevitt et al. |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0139752 A1 | 7/2003 | Pasricha et al. |
| 2003/0139775 A1 | 7/2003 | Grafton |
| 2003/0149448 A1 | 8/2003 | Foerster et al. |
| 2003/0152522 A1 | 8/2003 | Miller et al. |
| 2003/0153947 A1 | 8/2003 | Koseki |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0176920 A1 | 9/2003 | Sklar et al. |
| 2003/0181925 A1 | 9/2003 | Bain et al. |
| 2003/0195528 A1 | 10/2003 | Ritchart |
| 2003/0195564 A1 | 10/2003 | Tran et al. |
| 2003/0208209 A1 | 11/2003 | Gambale et al. |
| 2003/0208210 A1 | 11/2003 | Dreyfuss et al. |
| 2003/0212456 A1 | 11/2003 | Lipchitz et al. |
| 2003/0216809 A1 | 11/2003 | Ferguson |
| 2003/0220646 A1 | 11/2003 | Thelen et al. |
| 2003/0220660 A1 | 11/2003 | Kortenbach et al. |
| 2003/0225459 A1 | 12/2003 | Hammer et al. |
| 2003/0229361 A1 | 12/2003 | Jackson |
| 2003/0229396 A1* | 12/2003 | Andrews .............. A61F 2/08 623/13.13 |
| 2003/0236555 A1 | 12/2003 | Thornes |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Brown et al. |
| 2004/0024457 A1 | 2/2004 | Boyce et al. |
| 2004/0039389 A1 | 2/2004 | West et al. |
| 2004/0044351 A1 | 3/2004 | Searle |
| 2004/0044391 A1 | 3/2004 | Porter |
| 2004/0059357 A1 | 3/2004 | Koseki |
| 2004/0073176 A1 | 4/2004 | Utterberg |
| 2004/0087981 A1 | 5/2004 | Berube et al. |
| 2004/0092936 A1 | 5/2004 | Miller et al. |
| 2004/0093031 A1 | 5/2004 | Burkhart et al. |
| 2004/0093032 A1 | 5/2004 | Sinnott et al. |
| 2004/0098051 A1 | 5/2004 | Fallin et al. |
| 2004/0098053 A1 | 5/2004 | Tran |
| 2004/0111117 A1 | 6/2004 | Colleran et al. |
| 2004/0122431 A1 | 6/2004 | Biedermann et al. |
| 2004/0127907 A1 | 7/2004 | Dakin et al. |
| 2004/0133206 A1 | 7/2004 | Stevens et al. |
| 2004/0133211 A1 | 7/2004 | Raskin et al. |
| 2004/0133238 A1 | 7/2004 | Cerier |
| 2004/0138664 A1 | 7/2004 | Bowman |
| 2004/0138683 A1 | 7/2004 | Shelton et al. |
| 2004/0138704 A1 | 7/2004 | Gambale et al. |
| 2004/0138706 A1 | 7/2004 | Abrams et al. |
| 2004/0138747 A1 | 7/2004 | Kaladelfos |
| 2004/0143344 A1 | 7/2004 | Malaviya et al. |
| 2004/0147932 A1 | 7/2004 | Burkinshaw et al. |
| 2004/0147958 A1 | 7/2004 | Lam et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0181234 A1 | 9/2004 | McDevitt et al. |
| 2004/0182968 A1 | 9/2004 | Gentry |
| 2004/0187314 A1 | 9/2004 | Johnson |
| 2004/0193185 A1 | 9/2004 | McBrayer |
| 2004/0199169 A1 | 10/2004 | Koons et al. |
| 2004/0204722 A1 | 10/2004 | Sikora et al. |
| 2004/0220574 A1 | 11/2004 | Pelo et al. |
| 2004/0225183 A1 | 11/2004 | Michlitsch et al. |
| 2004/0225292 A1 | 11/2004 | Sasso et al. |
| 2004/0225305 A1 | 11/2004 | Ewers et al. |
| 2004/0236353 A1 | 11/2004 | Bain et al. |
| 2004/0236373 A1 | 11/2004 | Anspach |
| 2004/0243139 A1 | 12/2004 | Lewis et al. |
| 2004/0243178 A1 | 12/2004 | Haut et al. |
| 2004/0243180 A1 | 12/2004 | Donnelly et al. |
| 2004/0243235 A1 | 12/2004 | Goh et al. |
| 2004/0249394 A1 | 12/2004 | Morris et al. |
| 2004/0260296 A1 | 12/2004 | Kaiser et al. |
| 2004/0260298 A1 | 12/2004 | Kaiser et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267286 A1 | 12/2004 | Gao et al. |
| 2004/0267304 A1 | 12/2004 | Zannis et al. |
| 2004/0267309 A1 | 12/2004 | Garvin |
| 2004/0267317 A1 | 12/2004 | Higgins et al. |
| 2004/0267361 A1 | 12/2004 | Donnelly et al. |
| 2004/0267362 A1* | 12/2004 | Hwang .............. A61F 2/08 623/13.15 |
| 2005/0004670 A1 | 1/2005 | Gebhardt et al. |
| 2005/0021087 A1 | 1/2005 | Koseki |
| 2005/0027307 A1 | 2/2005 | Schwartz et al. |
| 2005/0033362 A1 | 2/2005 | Grafton |
| 2005/0033363 A1 | 2/2005 | Bojarski et al. |
| 2005/0038426 A1 | 2/2005 | Chan |
| 2005/0049598 A1 | 3/2005 | West, Jr. et al. |
| 2005/0055027 A1 | 3/2005 | Yeung et al. |
| 2005/0055037 A1 | 3/2005 | Fathauer |
| 2005/0064042 A1 | 3/2005 | Vunjak-Novakovic et al. |
| 2005/0065521 A1 | 3/2005 | Steger et al. |
| 2005/0065526 A1 | 3/2005 | Drew et al. |
| 2005/0070906 A1 | 3/2005 | Clark et al. |
| 2005/0070928 A1 | 3/2005 | Heino et al. |
| 2005/0074495 A1 | 4/2005 | Schwartz et al. |
| 2005/0076478 A1 | 4/2005 | Miyazaki et al. |
| 2005/0085819 A1 | 4/2005 | Ellis et al. |
| 2005/0090827 A1 | 4/2005 | Gedebou |
| 2005/0090828 A1 | 4/2005 | Alford |
| 2005/0090862 A1 | 4/2005 | McDevitt et al. |
| 2005/0096696 A1 | 5/2005 | Forsberg |
| 2005/0096697 A1 | 5/2005 | Forsberg et al. |
| 2005/0096743 A1 | 5/2005 | Schmieding et al. |
| 2005/0101957 A1 | 5/2005 | Buskirk et al. |
| 2005/0107795 A1 | 5/2005 | Morris et al. |
| 2005/0107828 A1 | 5/2005 | Reese |
| 2005/0119531 A1 | 6/2005 | Sharratt |
| 2005/0119696 A1 | 6/2005 | Walters et al. |
| 2005/0124996 A1 | 6/2005 | Hearn |
| 2005/0125031 A1 | 6/2005 | Pipenhagen et al. |
| 2005/0125036 A1 | 6/2005 | Roby |
| 2005/0125073 A1 | 6/2005 | Orban et al. |
| 2005/0131413 A1 | 6/2005 | O'Driscoll et al. |
| 2005/0137600 A1 | 6/2005 | Jacobs et al. |
| 2005/0137624 A1 | 6/2005 | Fallman |
| 2005/0149033 A1 | 7/2005 | McGuire et al. |
| 2005/0149118 A1 | 7/2005 | Koyfman et al. |
| 2005/0149122 A1 | 7/2005 | McDevitt et al. |
| 2005/0149187 A1 | 7/2005 | Clark et al. |
| 2005/0159812 A1 | 7/2005 | Dinger et al. |
| 2005/0165416 A1 | 7/2005 | Bojarski et al. |
| 2005/0165482 A1 | 7/2005 | Goldhahn et al. |
| 2005/0171547 A1 | 8/2005 | Aram |
| 2005/0171603 A1 | 8/2005 | Justin et al. |
| 2005/0187565 A1 | 8/2005 | Baker et al. |
| 2005/0187577 A1 | 8/2005 | Selvitelli et al. |
| 2005/0187635 A1 | 8/2005 | Metzger |
| 2005/0192632 A1 | 9/2005 | Geissler et al. |
| 2005/0203620 A1 | 9/2005 | Steiner et al. |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0240198 A1 | 10/2005 | Albertson et al. |

(56) References Cited

U.S. PATENT DOCUMENTS

| | | |
|---|---|---|
| 2005/0251153 A1 | 11/2005 | Sakamoto et al. |
| 2005/0251159 A1 | 11/2005 | Ewers et al. |
| 2005/0251177 A1 | 11/2005 | Saadat et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0267479 A1 | 12/2005 | Morgan et al. |
| 2005/0267533 A1 | 12/2005 | Gertner |
| 2005/0277939 A1 | 12/2005 | Miller |
| 2005/0277961 A1 | 12/2005 | Stone et al. |
| 2005/0283040 A1 | 12/2005 | Greenhalgh |
| 2005/0283156 A1 | 12/2005 | Schmieding et al. |
| 2005/0283158 A1 | 12/2005 | West |
| 2005/0283192 A1 | 12/2005 | Torrie et al. |
| 2006/0004364 A1 | 1/2006 | Green et al. |
| 2006/0004410 A1 | 1/2006 | Nobis et al. |
| 2006/0015103 A1 | 1/2006 | Burke |
| 2006/0015106 A1 | 1/2006 | Lerch et al. |
| 2006/0015107 A1 | 1/2006 | Sklar |
| 2006/0030884 A1 | 2/2006 | Yeung et al. |
| 2006/0030948 A1 | 2/2006 | Manrique et al. |
| 2006/0036265 A1 | 2/2006 | Dant |
| 2006/0052787 A1 | 3/2006 | Re et al. |
| 2006/0052818 A1 | 3/2006 | Drake et al. |
| 2006/0064125 A1 | 3/2006 | Henderson et al. |
| 2006/0064126 A1 | 3/2006 | Fallin et al. |
| 2006/0069334 A1 | 3/2006 | Moskowitz |
| 2006/0079904 A1 | 4/2006 | Thal |
| 2006/0084943 A1 | 4/2006 | Rosenman et al. |
| 2006/0085000 A1 | 4/2006 | Mohr et al. |
| 2006/0089672 A1 | 4/2006 | Martinek |
| 2006/0095130 A1 | 5/2006 | Caborn et al. |
| 2006/0095131 A1 | 5/2006 | Justin et al. |
| 2006/0100627 A1 | 5/2006 | Stone et al. |
| 2006/0100637 A1 | 5/2006 | Rathbun et al. |
| 2006/0106423 A1 | 5/2006 | Weisel et al. |
| 2006/0111721 A1 | 5/2006 | Puricelli et al. |
| 2006/0116685 A1 | 6/2006 | Urbanski et al. |
| 2006/0121084 A1 | 6/2006 | Borden et al. |
| 2006/0122608 A1 | 6/2006 | Fallin et al. |
| 2006/0122611 A1 | 6/2006 | Morales et al. |
| 2006/0135958 A1 | 6/2006 | Marissen et al. |
| 2006/0149258 A1 | 7/2006 | Sousa |
| 2006/0149266 A1 | 7/2006 | Cordasco |
| 2006/0155287 A1 | 7/2006 | Montgomery et al. |
| 2006/0155328 A1 | 7/2006 | Foerster |
| 2006/0161161 A1 | 7/2006 | Shifrin et al. |
| 2006/0167458 A1 | 7/2006 | Gabele |
| 2006/0167481 A1 | 7/2006 | Baker et al. |
| 2006/0167482 A1 | 7/2006 | Swain et al. |
| 2006/0173492 A1 | 8/2006 | Akerfeldt et al. |
| 2006/0178680 A1 | 8/2006 | Nelson et al. |
| 2006/0189993 A1 | 8/2006 | Stone |
| 2006/0190042 A1 | 8/2006 | Stone et al. |
| 2006/0195101 A1 | 8/2006 | Stevens |
| 2006/0195106 A1 | 8/2006 | Jones et al. |
| 2006/0200235 A1 | 9/2006 | Bianchi et al. |
| 2006/0212055 A1 | 9/2006 | Karabey et al. |
| 2006/0229623 A1 | 10/2006 | Bonutti et al. |
| 2006/0229671 A1 | 10/2006 | Steiner et al. |
| 2006/0229676 A1 | 10/2006 | Doll et al. |
| 2006/0235407 A1 | 10/2006 | Wang et al. |
| 2006/0235413 A1 | 10/2006 | Denham et al. |
| 2006/0241624 A1 | 10/2006 | Kizuka et al. |
| 2006/0247642 A1 | 11/2006 | Stone et al. |
| 2006/0253130 A1 | 11/2006 | Wolniewicz |
| 2006/0259048 A1 | 11/2006 | Koseki |
| 2006/0259076 A1 | 11/2006 | Burkhart |
| 2006/0264944 A1 | 11/2006 | Cole |
| 2006/0271192 A1 | 11/2006 | Olsen et al. |
| 2006/0276793 A1 | 12/2006 | Berry |
| 2006/0276809 A1 | 12/2006 | Oliveira |
| 2006/0276818 A1 | 12/2006 | Buser et al. |
| 2006/0276841 A1 | 12/2006 | Barbieri et al. |
| 2006/0276896 A1 | 12/2006 | Fallin et al. |
| 2006/0280768 A1 | 12/2006 | Hwang et al. |
| 2006/0282082 A1 | 12/2006 | Fanton et al. |
| 2006/0282083 A1 | 12/2006 | Fanton et al. |
| 2006/0282085 A1 | 12/2006 | Stone et al. |
| 2006/0293709 A1 | 12/2006 | Bojarski et al. |
| 2007/0005068 A1 | 1/2007 | Sklar |
| 2007/0005080 A1 | 1/2007 | Wolniewicz et al. |
| 2007/0010857 A1 | 1/2007 | Sugimoto et al. |
| 2007/0016305 A1 | 1/2007 | Chudik |
| 2007/0021779 A1 | 1/2007 | Garvin et al. |
| 2007/0027476 A1 | 2/2007 | Harris et al. |
| 2007/0032800 A1 | 2/2007 | Ortiz et al. |
| 2007/0032823 A1 | 2/2007 | Tegg |
| 2007/0038218 A1 | 2/2007 | Grevious |
| 2007/0043371 A1 | 2/2007 | Teague et al. |
| 2007/0055249 A1 | 3/2007 | Jensen et al. |
| 2007/0055251 A1 | 3/2007 | Huebner et al. |
| 2007/0055255 A1 | 3/2007 | Siegel |
| 2007/0060922 A1 | 3/2007 | Dreyfuss |
| 2007/0067025 A1 | 3/2007 | Schwartz |
| 2007/0071568 A1 | 3/2007 | Dorstewitz |
| 2007/0073307 A1 | 3/2007 | Scribner et al. |
| 2007/0073319 A1 | 3/2007 | Mikkaichi et al. |
| 2007/0073322 A1 | 3/2007 | Mikkaichi et al. |
| 2007/0078435 A1 | 4/2007 | Stone et al. |
| 2007/0083236 A1* | 4/2007 | Sikora .............. A61B 17/0401 606/232 |
| 2007/0088362 A1 | 4/2007 | Bonutti et al. |
| 2007/0093847 A1 | 4/2007 | Scribner et al. |
| 2007/0100350 A1 | 5/2007 | Deffenbaugh et al. |
| 2007/0112384 A1 | 5/2007 | Conlon et al. |
| 2007/0118217 A1 | 5/2007 | Brulez et al. |
| 2007/0123883 A1 | 5/2007 | Ellis et al. |
| 2007/0123984 A1 | 5/2007 | Hodorek |
| 2007/0142838 A1 | 6/2007 | Jordan |
| 2007/0156174 A1 | 7/2007 | Kaiser et al. |
| 2007/0162018 A1 | 7/2007 | Jensen et al. |
| 2007/0167950 A1 | 7/2007 | Tauro et al. |
| 2007/0185488 A1 | 8/2007 | Pohjonen et al. |
| 2007/0185532 A1 | 8/2007 | Stone et al. |
| 2007/0185568 A1 | 8/2007 | Schwartz |
| 2007/0191849 A1 | 8/2007 | ElAttrache et al. |
| 2007/0191853 A1 | 8/2007 | Stone |
| 2007/0198036 A1 | 8/2007 | Sklar et al. |
| 2007/0219558 A1 | 9/2007 | Deutsch |
| 2007/0225715 A1 | 9/2007 | Deffenbaugh et al. |
| 2007/0225719 A1 | 9/2007 | Stone et al. |
| 2007/0225763 A1 | 9/2007 | Zwolinski et al. |
| 2007/0225805 A1 | 9/2007 | Schmieding |
| 2007/0233241 A1 | 10/2007 | Graf et al. |
| 2007/0239209 A1 | 10/2007 | Fallman |
| 2007/0239275 A1 | 10/2007 | Willobee |
| 2007/0250059 A1 | 10/2007 | Weisshaupt et al. |
| 2007/0250163 A1 | 10/2007 | Cassani |
| 2007/0255282 A1 | 11/2007 | Simonton et al. |
| 2007/0260251 A1 | 11/2007 | Weier et al. |
| 2007/0260279 A1 | 11/2007 | Hotter et al. |
| 2007/0265704 A1 | 11/2007 | Mayer et al. |
| 2007/0270856 A1 | 11/2007 | Morales et al. |
| 2007/0270878 A1 | 11/2007 | Leisinger |
| 2007/0276387 A1 | 11/2007 | Morales et al. |
| 2007/0288023 A1 | 12/2007 | Pellegrino et al. |
| 2008/0009904 A1 | 1/2008 | Bourque et al. |
| 2008/0027430 A1 | 1/2008 | Montgomery et al. |
| 2008/0027440 A1 | 1/2008 | Marissen et al. |
| 2008/0027446 A1 | 1/2008 | Stone et al. |
| 2008/0033549 A1 | 2/2008 | Marshall et al. |
| 2008/0046009 A1 | 2/2008 | Albertorio et al. |
| 2008/0051836 A1 | 2/2008 | Foerster et al. |
| 2008/0065114 A1 | 3/2008 | Stone et al. |
| 2008/0071299 A1 | 3/2008 | Allinniemi et al. |
| 2008/0082101 A1 | 4/2008 | Reisberg |
| 2008/0082127 A1 | 4/2008 | Stone et al. |
| 2008/0082128 A1 | 4/2008 | Stone |
| 2008/0086138 A1 | 4/2008 | Stone et al. |
| 2008/0097430 A1 | 4/2008 | Bernstein et al. |
| 2008/0114460 A1 | 5/2008 | Willobee |
| 2008/0119892 A1 | 5/2008 | Brailovski et al. |
| 2008/0132753 A1 | 6/2008 | Goddard |

(56) References Cited

U.S. PATENT DOCUMENTS

| | | |
|---|---|---|
| 2008/0132932 A1 | 6/2008 | Hoeppner et al. |
| 2008/0132948 A1 | 6/2008 | Surti et al. |
| 2008/0133007 A1 | 6/2008 | Donnelly et al. |
| 2008/0137624 A1* | 6/2008 | Silverstrim ............ G08B 21/12 370/338 |
| 2008/0140092 A1 | 6/2008 | Stone et al. |
| 2008/0140093 A1 | 6/2008 | Stone et al. |
| 2008/0140128 A1 | 6/2008 | Smisson et al. |
| 2008/0154260 A1 | 6/2008 | Hoof |
| 2008/0154314 A1 | 6/2008 | McDevitt |
| 2008/0161806 A1 | 7/2008 | Donnelly et al. |
| 2008/0161852 A1 | 7/2008 | Kaiser et al. |
| 2008/0161861 A1 | 7/2008 | Huebner |
| 2008/0161864 A1 | 7/2008 | Beck et al. |
| 2008/0172097 A1 | 7/2008 | Lerch et al. |
| 2008/0177302 A1 | 7/2008 | Shurnas |
| 2008/0183290 A1 | 7/2008 | Baird et al. |
| 2008/0188933 A1* | 8/2008 | Koob ...................... A61L 27/24 623/13.12 |
| 2008/0188935 A1* | 8/2008 | Saylor ................ A61B 17/0401 623/13.14 |
| 2008/0188936 A1 | 8/2008 | Ball et al. |
| 2008/0208252 A1 | 8/2008 | Holmes |
| 2008/0221527 A1 | 9/2008 | Bradley et al. |
| 2008/0221578 A1 | 9/2008 | Zeitani |
| 2008/0228186 A1 | 9/2008 | Gall et al. |
| 2008/0228271 A1* | 9/2008 | Stone ........................ A61F 2/08 623/13.12 |
| 2008/0234730 A1 | 9/2008 | Cotton et al. |
| 2008/0255613 A1 | 10/2008 | Kaiser et al. |
| 2008/0257363 A1 | 10/2008 | Schoenefeld et al. |
| 2008/0262544 A1 | 10/2008 | Burkhart |
| 2008/0268064 A1 | 10/2008 | Woodell-May |
| 2008/0269674 A1 | 10/2008 | Stone |
| 2008/0275469 A1 | 11/2008 | Fanton et al. |
| 2008/0275477 A1 | 11/2008 | Sterrett et al. |
| 2008/0281428 A1 | 11/2008 | Meyers et al. |
| 2008/0288070 A1 | 11/2008 | Lo |
| 2008/0300611 A1 | 12/2008 | Houser et al. |
| 2008/0312689 A1 | 12/2008 | Denham et al. |
| 2008/0319478 A1 | 12/2008 | Foerster et al. |
| 2009/0018589 A1 | 1/2009 | Smisson, III et al. |
| 2009/0018654 A1* | 1/2009 | Schmieding ....... A61B 17/1615 623/13.14 |
| 2009/0018655 A1 | 1/2009 | Brunelle et al. |
| 2009/0043342 A1 | 2/2009 | Freedland |
| 2009/0054928 A1 | 2/2009 | Denham et al. |
| 2009/0062847 A1 | 3/2009 | Ken |
| 2009/0062854 A1 | 3/2009 | Kaiser et al. |
| 2009/0082790 A1 | 3/2009 | Shad et al. |
| 2009/0082805 A1 | 3/2009 | Kaiser et al. |
| 2009/0099598 A1 | 4/2009 | McDevitt et al. |
| 2009/0105717 A1 | 4/2009 | Bluechel |
| 2009/0105754 A1 | 4/2009 | Sethi |
| 2009/0118774 A1 | 5/2009 | Miller, III |
| 2009/0118775 A1 | 5/2009 | Burke |
| 2009/0125073 A1 | 5/2009 | Rehm |
| 2009/0138002 A1 | 5/2009 | Fenton |
| 2009/0138054 A1 | 5/2009 | Teague et al. |
| 2009/0156997 A1 | 6/2009 | Trenhaile |
| 2009/0163949 A1 | 6/2009 | Rolnick et al. |
| 2009/0177233 A1 | 7/2009 | Malek |
| 2009/0182335 A1* | 7/2009 | Struhl ................ A61B 17/0401 606/60 |
| 2009/0192468 A1 | 7/2009 | Stone |
| 2009/0198277 A1 | 8/2009 | Gordon et al. |
| 2009/0204146 A1 | 8/2009 | Kaiser et al. |
| 2009/0228015 A1* | 9/2009 | Ellis ................... A61B 17/8897 606/87 |
| 2009/0228042 A1 | 9/2009 | Koogle, Jr. et al. |
| 2009/0234357 A1 | 9/2009 | Morales et al. |
| 2009/0234358 A1 | 9/2009 | Morales et al. |
| 2009/0234451 A1 | 9/2009 | Manderson |
| 2009/0240251 A1 | 9/2009 | Gabele |
| 2009/0240335 A1 | 9/2009 | Arcenio et al. |
| 2009/0248091 A1 | 10/2009 | Teague et al. |
| 2009/0265014 A1 | 10/2009 | May et al. |
| 2009/0265015 A1 | 10/2009 | May et al. |
| 2009/0287215 A1 | 11/2009 | Fisher et al. |
| 2009/0299409 A1 | 12/2009 | Coe et al. |
| 2009/0306711 A1 | 12/2009 | Stone et al. |
| 2009/0312776 A1 | 12/2009 | Kaiser et al. |
| 2009/0312793 A1 | 12/2009 | Huxel et al. |
| 2009/0318960 A1 | 12/2009 | Burkhart |
| 2009/0318961 A1 | 12/2009 | Stone et al. |
| 2010/0016899 A1 | 1/2010 | Gelfand |
| 2010/0042114 A1 | 2/2010 | Schaffhausen |
| 2010/0063541 A1 | 3/2010 | Brunelle et al. |
| 2010/0087857 A1 | 4/2010 | Stone et al. |
| 2010/0094355 A1 | 4/2010 | Trenhaile |
| 2010/0106254 A1 | 4/2010 | Delsignore |
| 2010/0121348 A1 | 5/2010 | Van Der Burg et al. |
| 2010/0145384 A1 | 6/2010 | Stone et al. |
| 2010/0152752 A1 | 6/2010 | Denove et al. |
| 2010/0191342 A1 | 7/2010 | Byrd et al. |
| 2010/0211071 A1 | 8/2010 | Lettmann et al. |
| 2010/0211075 A1 | 8/2010 | Stone |
| 2010/0256677 A1 | 10/2010 | Albertorio et al. |
| 2010/0268273 A1 | 10/2010 | Albertorio et al. |
| 2010/0268275 A1 | 10/2010 | Stone et al. |
| 2010/0270306 A1 | 10/2010 | Shiffer |
| 2010/0274282 A1 | 10/2010 | Olson |
| 2010/0292792 A1 | 11/2010 | Stone et al. |
| 2010/0305698 A1 | 12/2010 | Metzger et al. |
| 2010/0305709 A1 | 12/2010 | Metzger et al. |
| 2010/0312341 A1 | 12/2010 | Kaiser et al. |
| 2010/0324676 A1* | 12/2010 | Albertorio ......... A61B 17/0401 623/13.14 |
| 2010/0331881 A1 | 12/2010 | Hart |
| 2011/0009885 A1 | 1/2011 | Graf et al. |
| 2011/0022083 A1 | 1/2011 | DiMatteo et al. |
| 2011/0026141 A1 | 2/2011 | Barrows |
| 2011/0046733 A1 | 2/2011 | Eggli |
| 2011/0087225 A1 | 4/2011 | Fritzinger |
| 2011/0087280 A1* | 4/2011 | Albertorio ......... A61B 17/0401 606/232 |
| 2011/0087284 A1 | 4/2011 | Stone et al. |
| 2011/0098727 A1 | 4/2011 | Kaiser et al. |
| 2011/0106153 A1 | 5/2011 | Stone et al. |
| 2011/0112537 A1 | 5/2011 | Bernstein et al. |
| 2011/0112538 A1 | 5/2011 | Dell'Oca |
| 2011/0160767 A1 | 6/2011 | Stone et al. |
| 2011/0160768 A1 | 6/2011 | Stone et al. |
| 2011/0184227 A1* | 7/2011 | Altman ..................... A61F 2/08 600/37 |
| 2011/0208239 A1 | 8/2011 | Stone et al. |
| 2011/0208240 A1 | 8/2011 | Stone et al. |
| 2011/0213416 A1 | 9/2011 | Kaiser |
| 2011/0218625 A1 | 9/2011 | Berelsman et al. |
| 2011/0224799 A1 | 9/2011 | Stone |
| 2011/0245868 A1 | 10/2011 | Teeslink et al. |
| 2011/0264141 A1 | 10/2011 | Denham et al. |
| 2011/0270278 A1 | 11/2011 | Overes et al. |
| 2011/0270306 A1 | 11/2011 | Denham et al. |
| 2011/0295284 A1* | 12/2011 | Purdue ..................... A61F 2/08 606/151 |
| 2011/0319932 A1 | 12/2011 | Avelar et al. |
| 2012/0004669 A1 | 1/2012 | Overes et al. |
| 2012/0041485 A1 | 2/2012 | Kaiser et al. |
| 2012/0041486 A1 | 2/2012 | Stone et al. |
| 2012/0041496 A1 | 2/2012 | Walker |
| 2012/0046693 A1 | 2/2012 | Denham et al. |
| 2012/0053630 A1 | 3/2012 | Denham et al. |
| 2012/0059417 A1 | 3/2012 | Norton et al. |
| 2012/0059418 A1 | 3/2012 | Denham et al. |
| 2012/0059468 A1 | 3/2012 | Mattern et al. |
| 2012/0089193 A1 | 4/2012 | Stone et al. |
| 2012/0095470 A1 | 4/2012 | Kaiser et al. |
| 2012/0109156 A1 | 5/2012 | Overes et al. |
| 2012/0116409 A1 | 5/2012 | Stone |
| 2012/0116450 A1 | 5/2012 | McDevitt et al. |
| 2012/0116452 A1 | 5/2012 | Stone et al. |
| 2012/0123447 A1 | 5/2012 | Corrao et al. |

(56) References Cited

U.S. PATENT DOCUMENTS

| | | |
|---|---|---|
| 2012/0123474 A1 | 5/2012 | Zajac et al. |
| 2012/0123541 A1 | 5/2012 | Albertorio et al. |
| 2012/0130492 A1 | 5/2012 | Eggli et al. |
| 2012/0143215 A1 | 6/2012 | Corrao et al. |
| 2012/0150223 A1 | 6/2012 | Manos et al. |
| 2012/0150297 A1 | 6/2012 | Denham et al. |
| 2012/0165866 A1 | 6/2012 | Kaiser et al. |
| 2012/0165867 A1 | 6/2012 | Denham et al. |
| 2012/0165938 A1 | 6/2012 | Denham et al. |
| 2012/0197271 A1 | 8/2012 | Astorino et al. |
| 2012/0215257 A1 | 8/2012 | McDevitt et al. |
| 2012/0245585 A1 | 9/2012 | Kaiser et al. |
| 2012/0265219 A1 | 10/2012 | Rushdy et al. |
| 2012/0290003 A1 | 11/2012 | Dreyfuss |
| 2012/0290004 A1 | 11/2012 | Lombardo et al. |
| 2012/0296427 A1 | 11/2012 | Conner et al. |
| 2012/0310245 A1 | 12/2012 | Hoeppner et al. |
| 2013/0018375 A1 | 1/2013 | Dell'Oca |
| 2013/0018416 A1 | 1/2013 | Lombardo et al. |
| 2013/0023928 A1 | 1/2013 | Dreyfuss |
| 2013/0023929 A1 | 1/2013 | Sullivan et al. |
| 2013/0023930 A1 | 1/2013 | Stone et al. |
| 2013/0035698 A1 | 2/2013 | Stone et al. |
| 2013/0035722 A1 | 2/2013 | McDevitt et al. |
| 2013/0046341 A1 | 2/2013 | Stone et al. |
| 2013/0090731 A1 | 4/2013 | Walker |
| 2013/0103082 A1 | 4/2013 | Kaiser et al. |
| 2013/0110165 A1 | 5/2013 | Burkhart et al. |
| 2013/0110251 A1 | 5/2013 | Metzger et al. |
| 2013/0116730 A1 | 5/2013 | Denham et al. |
| 2013/0123810 A1 | 5/2013 | Brown et al. |
| 2013/0123813 A1 | 5/2013 | Stone et al. |
| 2013/0131722 A1 | 5/2013 | Marchand et al. |
| 2013/0138123 A1 | 5/2013 | Stone et al. |
| 2013/0144337 A1 | 6/2013 | Stone et al. |
| 2013/0144338 A1 | 6/2013 | Stone et al. |
| 2013/0158601 A1 | 6/2013 | Stone et al. |
| 2013/0190818 A1 | 7/2013 | Norton |
| 2013/0190819 A1 | 7/2013 | Norton |
| 2013/0204276 A1 | 8/2013 | Stone et al. |
| 2013/0211452 A1 | 8/2013 | Stone et al. |
| 2013/0237997 A1 | 9/2013 | Arai et al. |
| 2013/0245761 A1 | 9/2013 | Conner et al. |
| 2013/0274812 A1 | 10/2013 | Dell'Oca |
| 2013/0289564 A1 | 10/2013 | Bernstein et al. |
| 2013/0317621 A1 | 11/2013 | Metzger et al. |
| 2013/0331848 A1 | 12/2013 | Kaiser et al. |
| 2014/0046367 A1 | 2/2014 | Stone et al. |
| 2014/0046368 A1 | 2/2014 | Kaiser et al. |
| 2014/0067081 A1 | 3/2014 | Stone |
| 2014/0088655 A1 | 3/2014 | Stone et al. |
| 2014/0094913 A1 | 4/2014 | Berelsman et al. |
| 2014/0135835 A1 | 5/2014 | Stone et al. |
| 2014/0163613 A1 | 6/2014 | Stone et al. |
| 2014/0163614 A1 | 6/2014 | Denham et al. |
| 2014/0194927 A1 | 7/2014 | Kaiser et al. |
| 2014/0200583 A1 | 7/2014 | Stone et al. |
| 2014/0257378 A1 | 9/2014 | Norton et al. |
| 2014/0276992 A1 | 9/2014 | Stone et al. |
| 2014/0277447 A1 | 9/2014 | Berelsman et al. |
| 2014/0324101 A1 | 10/2014 | Denham et al. |
| 2014/0330311 A1 | 11/2014 | Denham et al. |
| 2014/0336760 A1 | 11/2014 | Eggli |
| 2014/0350674 A1 | 11/2014 | Stone et al. |
| 2015/0012094 A1 | 1/2015 | Denham et al. |
| 2015/0057757 A1 | 2/2015 | Metzger et al. |
| 2015/0119890 A1 | 4/2015 | Kaiser et al. |
| 2015/0127051 A1 | 5/2015 | Kaiser et al. |
| 2015/0134000 A1 | 5/2015 | Denham et al. |
| 2015/0173887 A1 | 6/2015 | Berelsman et al. |
| 2015/0257750 A1 | 9/2015 | Kaiser et al. |
| 2016/0000483 A1 | 1/2016 | Stone |
| 2016/0022261 A1 | 1/2016 | Stone et al. |
| 2016/0058436 A1 | 3/2016 | Stone et al. |
| 2016/0081789 A1 | 3/2016 | Denham et al. |
| 2016/0106414 A1 | 4/2016 | Stone et al. |
| 2016/0128684 A1 | 5/2016 | Stone et al. |
| 2016/0183935 A1 | 6/2016 | Stone |
| 2016/0199053 A1 | 7/2016 | Norton et al. |
| 2016/0213369 A1 | 7/2016 | Stone et al. |
| 2016/0242760 A1 | 8/2016 | Kaiser et al. |
| 2017/0014225 A1 | 1/2017 | Denham et al. |
| 2017/0020507 A1 | 1/2017 | Denham et al. |
| 2017/0035411 A1 | 2/2017 | Kaiser et al. |
| 2017/0049557 A1 | 2/2017 | Denham et al. |
| 2017/0065278 A1 | 3/2017 | Stone |
| 2017/0071593 A1 | 3/2017 | Stone |
| 2017/0071595 A1 | 3/2017 | Stone et al. |
| 2017/0086816 A1 | 3/2017 | Norton |
| 2017/0119382 A1 | 5/2017 | Denham et al. |
| 2017/0128061 A1 | 5/2017 | Stone et al. |
| 2017/0181746 A1 | 6/2017 | Denham et al. |
| 2017/0189011 A1 | 7/2017 | Stone et al. |
| 2017/0202587 A1 | 7/2017 | Stone et al. |
| 2017/0273686 A1 | 9/2017 | Denham et al. |
| 2017/0311947 A1 | 11/2017 | Kaiser et al. |
| 2017/0319195 A1 | 11/2017 | Denham et al. |
| 2017/0325808 A1 | 11/2017 | Stone et al. |
| 2017/0333176 A1 | 11/2017 | Stone et al. |
| 2017/0360425 A1 | 12/2017 | Stone et al. |
| 2018/0000477 A1 | 1/2018 | Kaiser et al. |
| 2018/0014864 A1 | 1/2018 | Stone et al. |
| 2018/0021036 A1 | 1/2018 | Kaiser et al. |
| 2018/0021125 A1 | 1/2018 | Berelsman et al. |

FOREIGN PATENT DOCUMENTS

| | | |
|---|---|---|
| AU | 5850469 | 1/1971 |
| AU | 5963869 | 2/1971 |
| AU | 1505470 | 11/1971 |
| AU | 2223767 | 5/1973 |
| AU | 3615171 | 5/1973 |
| AU | 5028569 | 9/1973 |
| AU | 7110887 | 10/1987 |
| AU | 639410 | 11/1989 |
| AU | 651929 | 8/1994 |
| BE | 1010569 A6 | 10/1998 |
| CN | 1720872 A | 1/2006 |
| CN | 1777450 A | 5/2006 |
| CN | 101083954 A | 12/2007 |
| CN | 101584592 A | 11/2009 |
| CN | 105208970 A | 12/2015 |
| DE | 2529669 | 3/1976 |
| DE | 2747312 | 4/1979 |
| DE | 2818254 | 10/1979 |
| DE | 2919009 | 11/1979 |
| DE | 3027138 | 12/1981 |
| DE | 3225620 | 2/1983 |
| DE | 3136083 | 3/1983 |
| DE | 233303 C | 2/1986 |
| DE | 4127550 | 2/1993 |
| DE | 4302397 | 7/1993 |
| DE | 29621340 | 5/1998 |
| DE | 19841252 | 3/2000 |
| DE | 20207781 U1 | 8/2002 |
| EP | 19062 A1 | 11/1980 |
| EP | 0108912 | 5/1984 |
| EP | 0129422 | 12/1984 |
| EP | 0129442 | 12/1984 |
| EP | 0172130 | 2/1986 |
| EP | 0241240 | 10/1987 |
| EP | 0241792 | 10/1987 |
| EP | 0260970 | 3/1988 |
| EP | 0270704 | 6/1988 |
| EP | 0282789 | 9/1988 |
| EP | 0315371 | 5/1989 |
| EP | 0317406 | 5/1989 |
| EP | 0340159 | 11/1989 |
| EP | 0346183 | 12/1989 |
| EP | 0349173 | 1/1990 |
| EP | 0374088 | 6/1990 |
| EP | 0409364 | 1/1991 |
| EP | 0415915 | 3/1991 |
| EP | 0440991 | 8/1991 |

(56) References Cited

FOREIGN PATENT DOCUMENTS

| | | |
|---|---|---|
| EP | 440991 A1 | 8/1991 |
| EP | 0441065 | 8/1991 |
| EP | 0451932 | 10/1991 |
| EP | 0464480 | 1/1992 |
| EP | 0490417 | 6/1992 |
| EP | 0497079 | 8/1992 |
| EP | 0502509 | 9/1992 |
| EP | 0502698 | 9/1992 |
| EP | 520177 | 12/1992 |
| EP | 520177 A1 | 12/1992 |
| EP | 0546726 | 6/1993 |
| EP | 0574707 | 12/1993 |
| EP | 0574707 A1 | 12/1993 |
| EP | 0582514 | 2/1994 |
| EP | 0591991 | 4/1994 |
| EP | 0598219 | 5/1994 |
| EP | 0611551 A1 | 8/1994 |
| EP | 0627203 | 12/1994 |
| EP | 0651979 | 5/1995 |
| EP | 0669110 | 8/1995 |
| EP | 0686373 | 12/1995 |
| EP | 0702933 | 3/1996 |
| EP | 0775473 | 5/1997 |
| EP | 0913123 | 5/1999 |
| EP | 0913131 | 5/1999 |
| EP | 99121106 | 10/1999 |
| EP | 991210527 | 10/1999 |
| EP | 0995409 | 4/2000 |
| EP | 1013229 | 6/2000 |
| EP | 1093773 | 4/2001 |
| EP | 1093774 | 4/2001 |
| EP | 1555945 | 7/2005 |
| EP | 2238944 A2 | 10/2010 |
| EP | 2544607 A1 | 1/2013 |
| EP | 2709557 A1 | 3/2014 |
| EP | 2934379 A1 | 10/2015 |
| EP | 2434987 B1 | 6/2016 |
| EP | 2775935 B1 | 5/2017 |
| FR | 2622790 | 5/1989 |
| FR | 2655840 | 6/1991 |
| FR | 2682867 | 4/1993 |
| FR | 2687911 | 9/1993 |
| FR | 2688689 | 9/1993 |
| FR | 2704140 | 10/1994 |
| FR | 2717070 | 9/1995 |
| FR | 2723528 | 2/1996 |
| FR | 2744010 | 8/1997 |
| FR | 2745999 | 9/1997 |
| FR | 2770764 | 5/1999 |
| GB | 401677 | 11/1933 |
| GB | 1413477 | 11/1975 |
| GB | 1485681 | 9/1977 |
| GB | 2083751 | 3/1982 |
| GB | 2118474 | 11/1983 |
| GB | 2227175 | 7/1990 |
| GB | 2253147 A | 9/1992 |
| GB | 2312376 | 10/1997 |
| GB | 2403416 A | 1/2005 |
| GB | 2454251 A | 5/2009 |
| JP | 5362911 | 5/1978 |
| JP | 5362912 | 5/1978 |
| JP | 5374942 | 6/1978 |
| JP | 5378230 | 6/1978 |
| JP | 62159647 | 7/1987 |
| JP | 62295657 | 12/1987 |
| JP | 5269160 | 10/1993 |
| JP | 5300917 | 11/1993 |
| JP | 751292 | 2/1995 |
| JP | 10211213 | 8/1998 |
| JP | 5362911 B2 | 12/2013 |
| WO | WO-8300615 | 3/1983 |
| WO | WO-8603666 | 7/1986 |
| WO | WO-8701270 | 3/1987 |
| WO | WO-8901767 | 3/1989 |
| WO | WO-8909030 | 10/1989 |
| WO | WO-8910096 | 11/1989 |
| WO | WO-9008510 | 8/1990 |
| WO | WO-9203980 | 3/1992 |
| WO | WO-9314705 | 8/1993 |
| WO | WO-9315694 | 8/1993 |
| WO | WO-9502373 | 1/1995 |
| WO | WO-9503003 | 2/1995 |
| WO | WO-9529637 | 11/1995 |
| WO | WO-9532670 | 12/1995 |
| WO | WO-9609797 A1 | 4/1996 |
| WO | WO-9629029 | 9/1996 |
| WO | WO-9737603 | 10/1997 |
| WO | WO-9812991 | 4/1998 |
| WO | WO-9812992 | 4/1998 |
| WO | WO-9822047 | 5/1998 |
| WO | WO-9822048 | 5/1998 |
| WO | WO-9901084 | 1/1999 |
| WO | WO-9912480 | 3/1999 |
| WO | WO-9937219 A1 | 7/1999 |
| WO | WO-9944544 | 9/1999 |
| WO | WO-9952472 A1 | 10/1999 |
| WO | WO-0040159 | 7/2000 |
| WO | WO-0139671 | 6/2001 |
| WO | WO-0236020 | 5/2002 |
| WO | WO-03005914 A1 | 1/2003 |
| WO | WO-03071962 | 9/2003 |
| WO | WO-03077772 | 9/2003 |
| WO | WO-03092551 A1 | 11/2003 |
| WO | WO-2004091412 A1 | 10/2004 |
| WO | WO-2005104992 A1 | 11/2005 |
| WO | WO-2005122954 A1 | 12/2005 |
| WO | WO-2006011786 A1 | 2/2006 |
| WO | WO-2006023661 A2 | 3/2006 |
| WO | WO-2006055823 A2 | 5/2006 |
| WO | WO-2007045460 A2 | 4/2007 |
| WO | WO-2007103562 A2 | 9/2007 |
| WO | WO-2007109280 A2 | 9/2007 |
| WO | WO-2007119057 A1 | 10/2007 |
| WO | WO-2008002550 A2 | 1/2008 |
| WO | WO-2008015171 A1 | 2/2008 |
| WO | WO-2008073588 A2 | 6/2008 |
| WO | WO-2009012021 A1 | 1/2009 |
| WO | WO-2009083047 A1 | 7/2009 |
| WO | WO-2009131820 A1 | 10/2009 |
| WO | WO-2010138832 A1 | 12/2010 |
| WO | WO-2011112371 A1 | 9/2011 |
| WO | WO-2011150238 A1 | 12/2011 |
| WO | WO-2012134999 A1 | 10/2012 |
| WO | WO-2012158583 A1 | 11/2012 |
| WO | WO-2013066974 A1 | 5/2013 |
| WO | WO-2013074525 A1 | 5/2013 |
| WO | WO-2014/100109 A1 | 6/2014 |
| WO | WO-2014151766 A1 | 9/2014 |

OTHER PUBLICATIONS

"JuggerKnot™ Soft Anchor: Arthroscopic and Mini-Open Rotator Cuff Repair Using JuggerKnot™ Soft Anchor—2.9mm with ALLthread™ Knotless Anchor Surgical Technique" brochure, Biomet® Sports Medicine. (2013) 16 pages.

"ToggleLoc™ Fixation Device with ZipLoop™ Technology: ACL Reconstruction Bone-Tendon-Bone," by James R. Andrews, M.D., of Biomet Sports Medicine, a Biomet Company Brochure (2013), pp. 1-20.

International Preliminary Report on Patentability and Written Opinion mailed May 30, 2014 for PCT/US2012/064832 which claims benefit of U.S. Appl. No. 13/295,126, filed Nov. 14, 2011.

International Search Report and Written Opinion mailed Jun. 6, 2014 for PCT/US2014/026413 which claims benefit of U.S. Appl. No. 14/095,614, filed Dec. 3, 2013 and U.S. Appl. No. 14/095,639, filed Dec. 3, 2013.

ToggleLoc Fixation Device with ZipLoop Technology: Biceps Tendon Reattachment by Mark J. Albritton, M.D. and Daniel Worrel, M.D. of Biomet Sports Medicine, a Biomet Company Brochure (2099, 2011), pp. 1-12.

International Search Report and Written Opinion mailed Mar. 6, 2014 for PCT/US2013/075989 which claims benefit of U.S. Appl. No. 13/720,648, filed Dec. 19, 2012.

(56) References Cited

OTHER PUBLICATIONS

"AperFix® System Surgical Technique Guide. Single Tunnel Double Bundle.™" Cayenne Medical brochure. (Aug. 2008) 8 sheets.
"Arthroscopic Meniscal Repair using the Meniscal Cinch™", Surgical Technique brochure. (2008) Arthrex® 6 sheets.
"Bio-lntrafix (TCP/PLA & Intrafix, Tibial Soft Tissue Fasteners," by DePuy Mitek, 6 sheets, (date unknown).
"Bio-Intrafix Tibial Soft Tissue Fasteners, Building on the Legacy of IntraFix," brochure. DePuy Mitek,(Feb. 2007) 6 sheets.
"Biomechanical Evaluation of the Biomet Sports Medicine JurggerKnot™ Soft Anchor in Porcine Bone," Study completed Jan. 2010. Biomet Sports Medicine Research and Development, Warsaw, Indiana. 2 pages.
"Do your next distal tendon repair with . . . The Lubbers Technique", Teno Fix® brochure, 2003 (2 pages) Ortheon® Medical.
"EZ Loc Femoral Fixation Device," copyright 2005 Arthrotek, Inc. (8 sheets).
"JuggerKnot™ Soft Anchor Midfoot Repair," brochure. Biomet Sports Medicine (Jul. 2011) 12 sheets.
"JuggerKnot™ Soft Anchor. It's Small. It's strong. And its all suture . . ." Ordering Information brochure. Biomet Sports Medicine (Jun. 2011) 2 sheets.
"JuggerKnot™ Soft Anchor. Labral Repair," brochure. Biomet Sports Medicine (Apr. 2011) 12 sheets.
"Make your next tendon repair an open-and-shut case. The Teno Fix® Tendon Repair System", Teno Fix® brochure, 2003 (2 pages) Ortheon® Medical.
"PANALOK Anchor with PDS II and ETHIBOND Suture", Mitek Products ETHICON, 1997.
"SE Graft Tensioning System Surgical Technique," Linvatec Corporation copyright 2003, 2004.
"Suture Tensioner w/Tensiometer," Arthrex®, Inc. catalog "Next Generation in Knee Ligament Reconstruction & Repair Technology," 2009.
"Technique for ACL Reconstruction with Acufex Director Drill Guide and Endobutton CL," by Thomas D. Roseberg, copyright 1999 Smith & Nephew.
"TriTis™ Tibial Fixation System and Implant" brochure. Scandius Biomedical (2006).
A. Weiler, et al; Biodegradierbare Interferenzschrauben in der Kreuzbandchirurgie; OP-Journal 14 pp. 278-284; (Mar. 1998).
Arthrotek, A Biomet Company; Knees; Sure fire Hybrid Meniscal Device. (2005).
Arthrotek, A Biomet Company; Sure fire Hybrid Meniscal Device; Launch Date: Fall AANA 2004.
F. Alan Barber, M.D., "Uses and Abuses of Sutures and Anchors," Shoulder Scope, San Diego Shoulder Arthroscopy Library. http://www.shoulder.com/bass_barber.html Printed May 19, 2005.
F. Alan Barber, M.D., "Using Sutures and Anchors," San Diego Shoulder Arthroscopy Course, 17th Annual Meeting. (Jun. 14, 2000).
Flavia Namie Azato, et al. "Traction endurance biomechanical study of metallic suture anchors at different insertion angles," Acta ortop. bras., vol. 11, No. 1, Sao Paulo, Jan./Mar. 2003.
Hecker AT, et al., "Pull-out strength of suture anchors for rotator cuff and Bankart lesion repairs," Am J Sports Med. 1993.
International Preliminary Report on Patentability and Written Opinion mailed Nov. 28, 2013 for PCT/US2012/037703, which claims benefit of U.S. Appl. No. 13/109,672, filed May 17, 2011,and U.S. Appl. No. 13/109,667, filed May 17, 2011.
International Preliminary Report on Patentability mailed Dec. 6, 2012 for PCT/US2011/038188 claiming benefit of U.S. Appl. No. 12/788,966, filed May 27, 2010.
International Preliminary Report on Patentability mailed Sep. 20, 2012 for PCT/US2011/026349 which claims benefit of U.S. Appl. No. 12/719,337, filed Mar. 8, 2010.
International Search Report and Written Opinion mailed Feb. 6, 2013 for PCT/US2012/064832 which claims benefit of U.S. Appl. No. 13/295,126, filed Nov. 14, 2011.
International Search Report and Written Opinion mailed Jul. 28, 2011 for PCT/US2011/026349 claiming benefit of U.S. Appl. No. 12/938,902, filed Nov. 3, 2010; and U.S. Appl. No. 12/719,337, filed Mar. 8, 2010.
International Search Report and Written Opinion mailed Mar. 6, 2013 for PCT/US2012/062738 which claims benefit of U.S. Appl. No. 13/288,459, filed Nov. 3, 2011.
International Search Report and Written Opinion mailed Oct. 14, 2011 for PCT/US2011/038188 filed May 26, 2011 claiming benefit of U.S. Appl. No. 12/788,973, filed May 27, 2010 and U.S. Appl. No. 12/788,966, filed May 27, 2010.
International Search Report and Written Opinion mailed Sep. 21, 2012 for PCT/US2012/037703 filed May 14, 2012 claiming benefit of U.S. Appl. No. 13/109,667, filed May 17, 2011 and U.S. Appl. No. 13/109,672, filed May 17, 2011.
Invitation to Pay Additional Fees mailed Aug. 5, 2011 for PCT/US2011/038188 claiming benefit of U.S. Appl. No. 12/788,973, filed May 27, 2010 and U.S. Appl. No. 12/788,966, filed May 27, 2010.
Invitation to Pay Additional Fees mailed Jul. 19, 2012, for PCT/US2012/037703 claiming benefit of U.S. Appl. No. 13/109,667, filed May 7, 2011.
Invitation to Pay Additional Fees mailed Jun. 9, 2011 for PCT/US2011/026349 claiming benefit of U.S. Appl. No. 12/938,902, filed Nov. 3, 2010; and U.S. Appl. No. 12/719,337, filed Mar. 8, 2010.
Lawhorn, M.D., Keith, MaxFire™ Meniscal Repair Device with Zip Loop™ Technology, Biomet Sports Medicine, Feb. 29, 2008.
Mark D. Miller et al.; "Pitfalls Associated with FasT-Fix Meniscal Repair," Arthroscopy: The Journal of Arthroscopic and Related Surgery, vol. 18, No. 8 (October), 2002: pp. 939-943.
Opus Medical; The AutoCuff System; www.opusmedical.com; 2003.
Patrick Hunt, et al.; Development of a Perforated Biodegradable Interference Screw; Arthroscopy: The Journal of Arthroscopic and Related Surgery, vol. 21, No. 3; pp. 258-265; Mar. 2005.
Pioneer® Sternal Cable System (2010).
Rapid Sternal Closure (2006) KLS Martin L.P. http://www.rapidsternalclosure.com/medical/demo.php Web accessed Sep. 8, 2008.
Roy Alan Majors, M.D.; "Meniscal repairs: proven techniques and current trends," Lippincott Williams & Wilkins, Inc.; 2002.
Saxena, Pankaj, MCh, DNB et al., "Use of Double Wires in Sternal Closure, A Useful Technique," Texas Heart® Institute. Journal List>Tex Heart Inst J > v.33(4); (2006).
Shoulder Arthroscopy; pp. H-2-H-22. (date unknown).
Smith & Nephew Endoscopy, "Endoscopic Meniscal Repair Using the T-Fix;" 1996.
Smith & Nephew, "Fast-Fix," Meniscal Repair System; 2001.
Stuart E. Fromm, M.D., RapidLoc, Meniscal Repair System, Mitek Products, Ethicon, 2001.
ToggleLoc™ Femoral Fixation Device, Arthrotek, Mar. 31, 2006.
Zeitani, Jacob, M.D., "A New Sternal Reinforcement Device to Prevent and Treat Sternal Dehiscence," CTSNet.org (Jun. 30, 2008).
"U.S. Appl. No. 11/504,882, Supplemental Notice of Allowability mailed Mar. 12, 2015", 5 pgs.
"U.S. Appl. No. 12/719,337, Notice of Allowance mailed Mar. 11, 2015", 10 pgs.
"U.S. Appl. No. 13/098,927, Response filed Jul. 22, 2015 to Final Office Action mailed May 22, 2013", 17 pgs.
"U.S. Appl. No. 13/109,672, 312 Amendment filed Jan. 15, 2015", 3 pgs.
"U.S. Appl. No. 13/109,672, Notice of Allowance mailed Feb. 3, 2015", 2 pgs.
"U.S. Appl. No. 13/109,672, PTO Response to Rule 312 Communication mailed Jan. 27, 2015", 2 pgs.
"U.S. Appl. No. 13/281,009, Non Final Office Action mailed Jun. 2, 2015", 9 pgs.
"U.S. Appl. No. 13/281,009, Notice of Allowance mailed Feb. 24, 2016", 9 pgs.
"U.S. Appl. No. 13/281,009, Notice of Allowance mailed Jun. 23, 2016", 9 pgs.

(56) References Cited

OTHER PUBLICATIONS

"U.S. Appl. No. 13/281,009, Notice of Allowance mailed Oct. 29, 2015", 8 pgs.
"U.S. Appl. No. 13/281,009, Response filed Sep. 2, 2015 to Non Final Office Action mailed Jun. 2, 2015", 13 pgs.
"U.S. Appl. No. 13/281,009, Restriction Requirement mailed Feb. 11, 2015", 6 pgs.
"U.S. Appl. No. 13/288,459, Corrected Notice of Allowance mailed Aug. 3, 2016", 4 pgs.
"U.S. Appl. No. 13/288,459, Corrected Notice of Allowance mailed Sep. 9, 2016", 4 pgs.
"U.S. Appl. No. 13/288,459, Examiner Interview Summary mailed Feb. 6, 2015", 3 pgs.
"U.S. Appl. No. 13/288,459, Non Final Office Action mailed Jun. 24, 2015", 10 pgs.
"U.S. Appl. No. 13/288,459, Notice of Allowance mailed Jan. 11, 2016", 13 pgs.
"U.S. Appl. No. 13/288,459, Notice of Allowance mailed May 10, 2016", 7 pgs.
"U.S. Appl. No. 13/288,459, Response filed Mar. 3, 2015 to Non Final Office Action mailed Nov. 4, 2014", 16 pgs.
"U.S. Appl. No. 13/288,459, Response filed Oct. 23, 2015 to Non Final Office Action mailed Jun. 24, 2015", 14 pgs.
"U.S. Appl. No. 13/293,825, Notice of Allowability mailed Jun. 22, 2015", 7 pgs.
"U.S. Appl. No. 13/293,825, Notice of Allowance mailed May 19, 2015", 9 pgs.
"U.S. Appl. No. 13/293,825, Response filed Apr. 15, 2015 to Restriction Requirement mailed Feb. 12, 2015", 17 pgs.
"U.S. Appl. No. 13/293,825, Restriction Requirement mailed Feb. 12, 2015", 9 pgs.
"U.S. Appl. No. 13/295,126, Non Final Office Action mailed May 19, 2015", 9 pgs.
"U.S. Appl. No. 13/295,126, Notice of Allowance mailed Oct. 22, 2015", 9 pgs.
"U.S. Appl. No. 13/295,126, Response filed Apr. 13, 2015 to Restriction Requirement mailed Feb. 12, 2015", 1 pgs.
"U.S. Appl. No. 13/295,126, Response filed Aug. 17, 2015 to Non Final Office Action mailed May 19, 2015", 21 pgs.
"U.S. Appl. No. 13/295,126, Restriction Requirement mailed Feb. 12, 2015", 9 pgs.
"U.S. Appl. No. 13/311,936, Examiner Interview Summary mailed Feb. 12, 2015", 2 pgs.
"U.S. Appl. No. 13/311,936, Non Final Office Action mailed Feb. 9, 2015", 13 pgs.
"U.S. Appl. No. 13/311,936, Non Final Office Action mailed Oct. 19, 2015", 8 pgs.
"U.S. Appl. No. 13/311,936, Notice of Allowance mailed Mar. 29, 2016", 8 pgs.
"U.S. Appl. No. 13/311,936, Response filed Jan. 18, 2016 to Non Final Office Action mailed Oct. 19, 2015", 8 pgs.
"U.S. Appl. No. 13/311,936, Response filed Jun. 9, 2015 to Non Final Office Action mailed Feb. 9, 2015", 12 pgs.
"U.S. Appl. No. 13/350,985, Final Office Action mailed Apr. 16, 2015", 8 pgs.
"U.S. Appl. No. 13/350,985, Notice of Allowance mailed Jul. 27, 2015", 5 pgs.
"U.S. Appl. No. 13/350,985, Response filed Mar. 13, 2015 to Non Final Office Action mailed Dec. 15, 2014", 10 pgs.
"U.S. Appl. No. 13/350,985, Response filed Jul. 9, 2015 to Final Office Action mailed Apr. 16, 2015", 8 pgs.
"U.S. Appl. No. 13/625,413, Final Office Action mailed Oct. 30, 2015", 8 pgs.
"U.S. Appl. No. 13/625,413, Non Final Office Action mailed Jun. 8, 2015", 11 pgs.
"U.S. Appl. No. 13/625,413, Notice of Allowance mailed Apr. 1, 2016", 8 pgs.
"U.S. Appl. No. 13/625,413, Notice of Allowance mailed Dec. 11, 2015", 9 pgs.
"U.S. Appl. No. 13/625,413, Response filed May 11, 2015 to Restriction Requirement mailed Mar. 10, 2015", 1 pg.
"U.S. Appl. No. 13/625,413, Response filed Sep. 8, 2015 to Non Final Office Action mailed Jun. 8, 2015", 16 pgs.
"U.S. Appl. No. 13/625,413, Response filed Dec. 1, 2015 to Final Office Action mailed Oct. 30, 2015", 9 pgs.
"U.S. Appl. No. 13/625,413, Restriction Requirement mailed Mar. 10, 2015", 7 pgs.
"U.S. Appl. No. 13/645,964, Advisory Action mailed Feb. 4, 2016", 2 pgs.
"U.S. Appl. No. 13/645,964, Final Office Action mailed Oct. 6, 2015", 17 pgs.
"U.S. Appl. No. 13/645,964, Non Final Office Action mailed Mar. 15, 2016", 15 pgs.
"U.S. Appl. No. 13/645,964, Non Final Office Action mailed Mar. 17, 2015", 15 pgs.
"U.S. Appl. No. 13/645,964, Notice of Allowance mailed Jul. 21, 2016", 9 pgs.
"U.S. Appl. No. 13/645,964, Response filed Jun. 13, 2016 to Non Final Office Action mailed Mar. 15, 2016", 11 pgs.
"U.S. Appl. No. 13/645,964, Response filed Jul. 17, 2015 to Non Final Office Action mailed Mar. 17, 2015", 17 pgs.
"U.S. Appl. No. 13/645,964, Response filed Dec. 4, 2015 to Final Office Action mailed Oct. 6, 2015", 14 pgs.
"U.S. Appl. No. 13/656,821, Notice of Allowance mailed Jun. 18, 2015", 11 pgs.
"U.S. Appl. No. 13/656,821, Response filed May 11, 2015 to Restriction Requirement mailed Mar. 10, 2015", 1 pg.
"U.S. Appl. No. 13/656,821, Restriction Requirement mailed Mar. 10, 2015", 6 pgs.
"U.S. Appl. No. 13/720,648, Final Office Action mailed Nov. 16, 2015", 7 pgs.
"U.S. Appl. No. 13/720,648, Non Final Office Action mailed Jun. 10, 2015", 11 pgs.
"U.S. Appl. No. 13/720,648, Notice of Allowance mailed Feb. 5, 2016", 11 pgs.
"U.S. Appl. No. 13/720,648, Response filed Jan. 13, 2016 to Final Office Action mailed Nov. 16, 2015", 9 pgs.
"U.S. Appl. No. 13/720,648, Response filed May 11, 2015 to Restriction Requirement mailed Mar. 10, 2015", 8 pgs.
"U.S. Appl. No. 13/720,648, Response filed Oct. 9, 2015 to Non Final Office Action mailed Jun. 10, 2015", 12 pgs.
"U.S. Appl. No. 13/720,648, Restriction Requirement mailed Mar. 10, 2015", 8 pgs.
"U.S. Appl. No. 13/751,846, Final Office Action mailed Nov. 17, 2015", 9 pgs.
"U.S. Appl. No. 13/751,846, Non Final Office Action mailed Jun. 15, 2015", 10 pgs.
"U.S. Appl. No. 13/751,846, Notice of Allowance mailed Mar. 16, 2016", 11 pgs.
"U.S. Appl. No. 13/751,846, Notice of Allowance mailed Jul. 6, 2016", 9 pgs.
"U.S. Appl. No. 13/751,846, Response filed Feb. 5, 2016 to Final Office Action mailed Nov. 17, 2015", 14 pgs.
"U.S. Appl. No. 13/751,846, Response filed May 11, 2015 to Restriction Requirement mailed Mar. 10, 2015", 15 pgs.
"U.S. Appl. No. 13/751,846, Response filed Oct. 9, 2015 to Non Final Office Action mailed Jun. 15, 2015", 20 pgs.
"U.S. Appl. No. 13/751,846, Restriction Requirement mailed Mar. 10, 2015", 7 pgs.
"U.S. Appl. No. 13/757,003, Non Final Office Action mailed Jun. 25, 2015", 8 pgs.
"U.S. Appl. No. 13/757,003, Notice of Allowance mailed Feb. 8, 2016", 10 pgs.
"U.S. Appl. No. 13/757,003, Response filed May 12, 2015 to Restriction Requirement mailed Mar. 12, 2015", 9 pgs.
"U.S. Appl. No. 13/757,003, Response filed Oct. 26, 2015 to Non Final Office Action mailed Jul. 25, 2015", 8 pgs.
"U.S. Appl. No. 13/757,003, Restriction Requirement mailed Mar. 12, 2015", 6 pgs.
"U.S. Appl. No. 13/757,019, Non Final Office Action mailed Jun. 25, 2015", 11 pgs.

(56) References Cited

OTHER PUBLICATIONS

"U.S. Appl. No. 13/757,019, Notice of Allowance mailed Dec. 10, 2015", 10 pgs.
"U.S. Appl. No. 13/757,019, Response filed May 11, 2015 to Restriction Requirement mailed Mar. 11, 2015", 9 pgs.
"U.S. Appl. No. 13/757,019, Response filed Oct. 26, 2015 to Non Final Office Action mailed Jun. 25, 2015", 9 pgs.
"U.S. Appl. No. 13/757,019, Restriction Requirement mailed Mar. 11, 2015", 10 pgs.
"U.S. Appl. No. 13/767,401, Non Final Office Action mailed Aug. 26, 2015", 9 pgs.
"U.S. Appl. No. 13/767,401, Notice of Allowance mailed Apr. 8, 2016", 9 pgs.
"U.S. Appl. No. 13/767,401, Notice of Allowance mailed Dec. 30, 2015", 9 pgs.
"U.S. Appl. No. 13/767,401, Response filed May 18, 2015 to Restriction Requirement mailed Mar. 17, 2015", 15 pgs.
"U.S. Appl. No. 13/767,401, Response filed Nov. 6, 2015 to Non Final Office Action mailed Aug. 26, 2015", 12 pgs.
"U.S. Appl. No. 13/767,401, Restriction Requirement mailed Mar. 17, 2015", 8 pgs.
"U.S. Appl. No. 13/790,982, Examiner Interview Summary mailed Jun. 9, 2015", 3 pgs.
"U.S. Appl. No. 13/790,982, Non Final Office Action mailed Sep. 16, 2015", 11 pgs.
"U.S. Appl. No. 13/790,982, Notice of Allowance mailed Feb. 24, 2016", 10 pgs.
"U.S. Appl. No. 13/790,982, Response filed Jun. 2, 2015 to Restriction Requirement mailed Apr. 2, 2015", 11 pgs.
"U.S. Appl. No. 13/790,982, Response filed Dec. 16, 2015 to Non Final Office Action mailed Sep. 16, 2015", 10 pgs.
"U.S. Appl. No. 13/790,982, Restriction Requirement mailed Apr. 2, 2015", 10 pgs.
"U.S. Appl. No. 13/790,997, Examiner Interview Summary mailed Jun. 8, 2015", 3 pgs.
"U.S. Appl. No. 13/790,997, Non Final Office Action mailed Sep. 21, 2015", 8 pgs.
"U.S. Appl. No. 13/790,997, Notice of Allowance mailed Mar. 2, 2016", 9 pgs.
"U.S. Appl. No. 13/790,997, Response filed Jun. 2, 2015 to Restriction Requirement mailed Apr. 2, 2015", 12 pgs.
"U.S. Appl. No. 13/790,997, Response filed Dec. 18, 2015 to Non Final Office Action mailed Sep. 21, 2015", 9 pgs.
"U.S. Appl. No. 13/790,997, Restriction Requirement mailed Apr. 2, 2015", 8 pgs.
"U.S. Appl. No. 13/833,567, Advisory Action mailed Apr. 28, 2016", 3 pgs.
"U.S. Appl. No. 13/833,567, Final Office Action mailed Mar. 9, 2016", 9 pgs.
"U.S. Appl. No. 13/833,567, Non Final Office Action mailed May 27, 2016", 9 pgs.
"U.S. Appl. No. 13/833,567, Non Final Office Action mailed Oct. 23, 2015", 10 pgs.
"U.S. Appl. No. 13/833,567, Response filed Jan. 22, 2016 to Non Final Office Action mailed Oct. 23, 2015", 11 pgs.
"U.S. Appl. No. 13/833,567, Response filed Jun. 25, 2015 to Restriction Requirement mailed Apr. 3, 2015", 10 pgs.
"U.S. Appl. No. 13/833,567, Response filed Aug. 4, 2016 to Non Final Office Action mailed May 27, 2016", 11 pgs.
"U.S. Appl. No. 13/833,567, Restriction Requirement mailed Apr. 3, 2015", 6 pgs.
"U.S. Appl. No. 13/838,755, Final Office Action mailed Feb. 22, 2016", 9 pgs.
"U.S. Appl. No. 13/838,755, Non Final Office Action mailed Sep. 17, 2015", 11 pgs.
"U.S. Appl. No. 13/838,755, Notice of Allowance mailed Apr. 27, 2016", 7 pgs.
"U.S. Appl. No. 13/838,755, Notice of Allowance mailed Aug. 3, 2016", 8 pgs.
"U.S. Appl. No. 13/838,755, Response filed Apr. 15, 2016 to Final Office Action mailed Feb. 22, 2016", 11 pgs.
"U.S. Appl. No. 13/838,755, Response filed Jun. 8, 2015 to Restriction Requirement mailed Apr. 6, 2015", 1 pg.
"U.S. Appl. No. 13/838,755, Response filed Dec. 1, 2015 to Non Final Office Action mailed Sep. 17, 2015", 13 pgs.
"U.S. Appl. No. 13/838,755, Restriction Requirement mailed Apr. 6, 2015", 6 pgs.
"U.S. Appl. No. 13/889,851, Non Final Office Action mailed Apr. 6, 2015", 10 pgs.
"U.S. Appl. No. 13/889,851, Notice of Allowance mailed Aug. 12, 2015", 8 pgs.
"U.S. Appl. No. 13/889,851, Response filed Feb. 26, 2015 to Restriction Requirement mailed Jan. 21, 2015", 12 pgs.
"U.S. Appl. No. 13/889,851, Response filed Jul. 6, 2015 to Non Final Office Action mailed Apr. 6, 2015", 14 pgs.
"U.S. Appl. No. 13/889,851, Restriction Requirement mailed Jan. 21, 2015", 6 pgs.
"U.S. Appl. No. 13/889,851, Supplemental Amendment and Response filed Jul. 6, 2015 to Non Final Office Action mailed Apr. 6, 2015", 8 pgs.
"U.S. Appl. No. 13/959,145, Examiner Interview Summary mailed Sep. 16, 2015", 3 pgs.
"U.S. Appl. No. 13/959,145, Final Office Action mailed Jan. 29, 2016", 16 pgs.
"U.S. Appl. No. 13/959,145, Final Office Action mailed Feb. 5, 2015", 22 pgs.
"U.S. Appl. No. 13/959,145, Non Final Office Action mailed Jul. 31, 2015", 21 pgs.
"U.S. Appl. No. 13/959,145, Notice of Allowability mailed Jun. 14, 2016", 2 pgs.
"U.S. Appl. No. 13/959,145, Notice of Allowance mailed Apr. 13, 2016", 5 pgs.
"U.S. Appl. No. 13/959,145, Response filed Mar 28, 2016 to Final Office Action mailed Jan. 29, 2016", 10 pgs.
"U.S. Appl. No. 13/959,145, Response filed Jul. 6, 2015 to Final Office Action mailed Feb. 5, 2015", 18 pgs.
"U.S. Appl. No. 13/959,145, Response filed Oct. 30, 2015 to Non Final Office Action mailed Jul. 31, 2015", 14 pgs.
"U.S. Appl. No. 14/055,172, Non Final Office Action mailed Jul. 14, 2016", 12 pgs.
"U.S. Appl. No. 14/055,172, Response filed May 4, 2016 to Restriction Requirement mailed Mar. 4, 2016", 8 pgs.
"U.S. Appl. No. 14/055,172, Restriction Requirement mailed Mar. 4, 2016", 6 pgs.
"U.S. Appl. No. 14/055,191, Non Final Office Action mailed May 16, 2016", 8 pgs.
"U.S. Appl. No. 14/055,191, Notice of Allowability mailed Sep. 8, 2016", 7 pgs.
"U.S. Appl. No. 14/055,191, Notice of Allowance mailed Aug. 31, 2016", 13 pgs.
"U.S. Appl. No. 14/055,191, Response filed Apr. 29, 2016 to Restriction Requirement mailed Mar. 7, 2016", 8 pgs.
"U.S. Appl. No. 14/055,191, Response filed Aug. 3, 2016 to Non Final Office Action mailed May 16, 2016", 11 pgs.
"U.S. Appl. No. 14/055,191, Restriction Requirement mailed Mar. 7, 2016", 6 pgs.
"U.S. Appl. No. 14/071,295, Supplemental Notice of Allowability mailed Jan. 26, 2015", 2 pgs.
"U.S. Appl. No. 14/094,311, Notice of Allowance mailed Aug. 16, 2016", 12 pgs.
"U.S. Appl. No. 14/094,311, Response filed Jul. 26, 2016 to Restriction Requirement mailed Jun. 22, 2016", 10 pgs.
"U.S. Appl. No. 14/094,311, Restriction Requirement mailed Jun. 22, 2016", 6 pgs.
"U.S. Appl. No. 14/095,639, Response filed Sep. 12, 2016 to Restriction Requirement mailed Jul. 19, 2016", 7 pgs.
"U.S. Appl. No. 14/095,639, Restriction Requirement mailed Jul. 19, 2016", 8 pgs.
"U.S. Appl. No. 14/107,350, Notice of Allowance mailed Feb. 26, 2016", 11 pgs.
"U.S. Appl. No. 14/107,350, Notice of Allowance mailed Jul. 27, 2016", 7 pgs.

(56) References Cited

OTHER PUBLICATIONS

"U.S. Appl. No. 14/159,094, Non Final Office Action mailed Jun. 29, 2016", 15 pgs.
"U.S. Appl. No. 14/159,094, Response filed Jun. 3, 2016 to Restriction Requirement mailed Apr. 20, 2016", 9 pgs.
"U.S. Appl. No. 14/159,094, Restriction Requirement mailed Apr. 20, 2016", 6 pgs.
"U.S. Appl. No. 14/182,038, Non Final Office Action mailed Jul. 19, 2016", 10 pgs.
"U.S. Appl. No. 14/182,038, Response filed Jun. 27, 2016 to Restriction Requirement mailed Apr. 26, 2016", 8 pgs.
"U.S. Appl. No. 14/182,038, Restriction Requirement mailed Apr. 26, 2016", 7 pgs.
"U.S. Appl. No. 14/182,046, Non Final Office Action mailed Jul. 15, 2016", 9 pgs.
"U.S. Appl. No. 14/182,046, Response filed Jun. 27, 2016 to Restriction Requirement mailed Apr. 26, 2016", 7 pgs.
"U.S. Appl. No. 14/182,046, Restriction Requirement mailed Apr. 26, 2016", 6 pgs.
"U.S. Appl. No. 14/211,977, Notice of Allowance mailed Jul. 12, 2016", 9 pgs.
"U.S. Appl. No. 14/211,977, Preliminary Amendment filed Mar. 2, 2016", 7 pgs.
"U.S. Appl. No. 14/211,977, Response filed Apr. 29, 2016 to Restriction Requirement mailed Mar. 11, 2016", 8 pgs.
"U.S. Appl. No. 14/211,977, Restriction Requirement mailed Mar. 11, 2016", 6 pgs.
"U.S. Appl. No. 14/215,550, Non Final Office Action mailed Jul. 19, 2016", 12 pgs.
"U.S. Appl. No. 14/215,550, Response filed Jun. 22, 2016 to Restriction Requirement mailed Apr. 28, 2016", 7 pgs.
"U.S. Appl. No. 14/215,550, Restriction Requirement mailed Apr. 28, 2016", 6 pgs.
"U.S. Appl. No. 14/275,548, Examiner Interview Summary mailed May 25, 2016", 3 pgs.
"U.S. Appl. No. 14/275,548, Non Final Office Action mailed Feb. 19, 2016", 14 pgs.
"U.S. Appl. No. 14/275,548, Notice of Allowance mailed Jul. 27, 2016", 7 pgs.
"U.S. Appl. No. 14/275,548, Response filed May 19, 2016 to Non Final Office Action mailed Feb. 19, 2016", 19 pgs.
"U.S. Appl. No. 14/324,688, Non Final Office Action mailed Jan. 8, 2016", 18 pgs.
"U.S. Appl. No. 14/324,688, Notice of Allowance mailed Jun. 9, 2016", 7 pgs.
"U.S. Appl. No. 14/324,688, Response filed Apr. 8, 2016 to Non Final Office Action mailed Jan. 8, 2016", 15 pgs.
"U.S. Appl. No. 14/456,286, Advisory Action mailed Jun. 21, 2016", 3 pgs.
"U.S. Appl. No. 14/456,286, Final Office Action mailed May 27, 2016", 15 pgs.
"U.S. Appl. No. 14/456,286, Non Final Office Action mailed Dec. 30, 2015", 16 pgs.
"U.S. Appl. No. 14/456,286, Response filed Mar. 30, 2016 to Non Final Office Action mailed Dec. 30, 2015", 15 pgs.
"U.S. Appl. No. 14/456,286, Response filed Jun. 13, 2016 to Final Office Action mailed May 27, 2016", 10 pgs.
"U.S. Appl. No. 14/456,286, Response filed Dec. 11, 2015 to Restriction Requirement mailed Oct. 29, 2015", 6 pgs.
"U.S. Appl. No. 14/456,286, Restriction Requirement mailed Oct. 29, 2015", 9 pgs.
"U.S. Appl. No. 14/492,590, Response filed Sep. 15, 2016 to Restriction Requirement mailed Jul. 25, 2015", 7 pgs.
"U.S. Appl. No. 14/492,590, Restriction Requirement mailed Jul. 25, 2016", 6 pgs.
"U.S. Appl. No. 14/589,101, Final Office Action mailed Oct. 2, 2015", 10 pgs.
"U.S. Appl. No. 14/589,101, Non Final Office Action mailed Feb. 12, 2015", 10 pgs.
"U.S. Appl. No. 14/589,101, Non Final Office Action mailed May 5, 2016", 14 pgs.
"U.S. Appl. No. 14/589,101, Response filed Jun. 12, 2015 to Non Final Office Action mailed Feb. 12, 2015", 11 pgs.
"U.S. Appl. No. 14/589,101, Response filed Dec. 29, 2015 to Final Office Action mailed Oct. 2, 2015", 15 pgs.
"U.S. Appl. No. 14/589,191, Response filed Aug. 5, 2016 to Non Final Office Action mailed May 5, 2016", 16 pgs.
"U.S. Appl. No. 14/697,140, Non Final Office Action mailed Apr. 8, 2016", 8 pgs.
"U.S. Appl. No. 14/697,140, Response filed Jun. 13, 2016 to Non Final Office Action mailed Apr. 8, 2016", 10 pgs.
"U.S. Appl. No. 14/794,309, Preliminary Amendment filed Sep. 22, 2015", 6 pgs.
"U.S. Appl. No. 14/794,309, Supplemental Preliminary Amendment filed Mar. 3, 2016", 8 pgs.
"U.S. Appl. No. 14/876,167, Preliminary Amendment filed Oct. 27, 2015", 8 pgs.
"U.S. Appl. No. 14/936,831, Preliminary Amendment filed Nov. 11, 2015", 6 pgs.
"U.S. Appl. No. 14/956,724, Preliminary Amendment filed Dec. 7, 2015", 8 pgs.
"U.S. Appl. No. 14/956,724, Supplemental Preliminary Amendment filed Feb. 11, 2016", 7 pgs.
"U.S. Appl. No. 14/983,108, Preliminary Amendment filed Dec. 30, 2015", 7 pgs.
"U.S. Appl. No. 14/983,747, Preliminary Amendment filed Jan. 4, 2016", 5 pgs.
"U.S. Appl. No. 15/060,007, Preliminary Amendment filed Mar. 9, 2016", 9 pgs.
"U.S. Appl. No. 15/061,352, Preliminary Amendment filed Mar. 7, 2016", 8 pgs.
"U.S. Appl. No. 15/074,553, Preliminary Amendment filed Mar. 21, 2016", 8 pgs.
"U.S. Appl. No. 13/833,567, Response filed Apr. 20, 2016 to Final Office Action mailed Mar. 9, 2016", 10 pgs.
"Chinese Application Serial No. 201480027708.4, Office Action mailed May 26, 2016", W/ English Translation, 15 pgs.
"European Application Serial No. 10727548.9, Office Action mailed Jan. 11, 2016", 6 pgs.
"European Application Serial No. 10727548.9, Response filed Mar. 19, 2015 to Examination Notification Art. 94(3) mailed Sep. 18, 2014", 23 pgs.
"European Application Serial No. 11707316.3, Office Action mailed Nov. 10, 2015", 6 pgs.
"European Application Serial No. 11707316.3, Response filed Jun. 29, 2015 to Examination Notification Art. 94(3) mailed Dec. 17, 2014", 25 pgs.
"European Application Serial No. 12721676.0, Communication pursuant to Article 94(3) EPC mailed Sep. 30, 2015", 4 pgs.
"European Application Serial No. 12721676.0, Response filed Apr. 11, 2016 to Communication pursuant to Article 94(3) EPC mailed Sep. 30, 2015", 38 pgs.
"European Application Serial No. 12791902.5, Examination Notification Art. 94(3) mailed Aug. 14, 2015", 4 pgs.
"European Application Serial No. 12806211.4, Examination Notification Art. 94(3) mailed Aug. 13, 2015", 5 pgs.
"European Application Serial No. 12806211.4, Response filed Feb. 23, 2016 to Communication Pursuant to Article 94(3) EPC mailed Aug. 13, 2015", 11 pgs.
"European Application Serial No. 13818131.8, Office Action mailed Jul. 28, 2015", 2 pgs.
"European Application Serial No. 13818131.8, Response filed Feb. 8, 2016 to Office Action mailed Jul. 28, 2015", 14 pgs.
"European Application Serial No. 14716173.1, Office Action mailed Nov. 5, 2015", 2 pgs.
"European Application Serial No. 14716173.1, Response filed May 16, 2016 to Communication pursuant to Rules 161(1) and 162 EPC mailed Nov. 5, 2015", 10 pgs.
"European Application Serial No. 12806211.4, Communication Pursuant to Article 94(3) EPC mailed Jun. 23, 2016", 4 pgs.

(56) References Cited

OTHER PUBLICATIONS

"International Application Serial No. PCT/US2013/075989, International Preliminary Report on Patentability mailed Jul. 2, 2015", 10 pgs.
"International Application Serial No. PCT/US2014/026413, International Preliminary Report on Patentability mailed Sep. 24, 2015", 10 pgs.
Thomas, Roseberg D, "Technique for ACL Reconstruction with Acufex Director Drill Guide and Endobutton CL", Smith & Nephew, Technique Guide, (1999), 18 pgs.
"U.S. Appl. No. 13/288,459, Corrected Notice of Allowance mailed Sep. 23, 2016", 4 pgs.
"U.S. Appl. No. 13/833,567, Notice of Allowance mailed Sep. 27, 2016", 9 pgs.
"U.S. Appl. No. 14/055,172, Response filed Nov. 14, 2016 to Non Final Office Action mailed Jul. 14, 2016", 19 pgs.
"U.S. Appl. No. 14/159,094, Response filed Sep. 19, 2016 to Non Final Office Action mailed Jun. 29, 2016", 13 pgs.
"U.S. Appl. No. 14/182,038, Response filed Oct. 19, 2016 to Non Final Office Action mailed Jul. 19, 2016", 15 pgs.
"U.S. Appl. No. 14/182,046, Response filed Oct. 17, 2016 to Non Final Office Action mailed Jul. 15, 2016", 11 pgs.
"U.S. Appl. No. 14/324,688, Corrected Notice of Allowance mailed Sep. 22, 2016", 2 pgs.
"U.S. Appl. No. 14/456,286, Non Final Office Action mailed Oct. 17, 2016", 17 pgs.
"U.S. Appl. No. 14/492,590, Notice of Allowance mailed Oct. 5, 2016", 10 pgs.
"U.S. Appl. No. 14/492,590, Supplemental Response filed Sep. 26, 2016 to Restriction Requirement mailed Jul. 25, 2016", 10 pgs.
"U.S. Appl. No. 14/594,285, Restriction Requirement mailed Nov. 7, 2016", 6 pgs.
"U.S. Appl. No. 14/697,140, Final Office Action mailed Sep. 23, 2016", 10 pgs.
"U.S. Appl. No. 14/956,724, Supplemental Preliminary Amendment filed Oct. 3, 2016", 8 pgs.
"U.S. Appl. No. 15/278,777, Preliminary Amendment filed Oct. 3, 2016", 7 pgs.
"U.S. Appl. No. 15/288,183, Preliminary Amendment filed Oct. 31, 2016", 7 pgs.
"U.S. Appl. No. 15/297,844, Preliminary Amendment filed Oct. 20, 2016", 7 pgs.
"Chinese Application Serial No. 201480027708.4, Response filed Oct. 10, 2016 to Office Action mailed May 26, 2016", With English Translation of Claims, 14 pgs.
"European Application Serial No. 12791902.5, Response filed Feb. 23, 2016 to Examination Notification Art. 94(3) mailed Aug. 14, 2015", 12 pgs.
Ziptight™ Fixation System Featuring Zip Loop™ Technology. Ankle Syndesmosis. Surgical Protocol by Timothy Charlton, M.D. Biomet Sports® Medicine brochure. (Jun. 15, 2011) 8 pages.
"U.S. Appl. No. 13/281,009, Corrected Notice of Allowance mailed Nov. 18, 2016", 4 pgs.
"U.S. Appl. No. 13/281,009, Corrected Notice of Allowance mailed Dec. 12, 2016", 2 pgs.
"U.S. Appl. No. 13/281,009, Examiner Interview Summary mailed Nov. 18, 2016", 2 pgs.
"U.S. Appl. No. 14/055,172, Final Office Action mailed Dec. 22, 2016", 8 pgs.
"U.S. Appl. No. 14/055,172, Response filed Feb. 22, 2017 to Final Office Action mailed Dec. 22, 2016", 11 pgs.
"U.S. Appl. No. 14/094,311, Notice of Allowance mailed Dec. 27, 2016", 8 pgs.
"U.S. Appl. No. 14/095,639, Non Final Office Action mailed Jan. 18, 2017", 10 pgs.
"U.S. Appl. No. 14/159,094, Examiner interview Summary mailed Nov. 29, 2016", 1 pg.
"U.S. Appl. No. 14/159,094, Notice of Allowance mailed Nov. 29, 2016", Examiner Interview Summary from Nov. 29, 2016 included, 11 pgs.
"U.S. Appl. No. 14/182,038, Advisory Action mailed Mar. 1, 2017", 3 pgs.
"U.S. Appl. No. 14/182,038, Final Office Action mailed Dec. 19, 2016", 8 pgs.
"U.S. Appl. No. 14/182,038, Response filed Feb. 20, 2017 to Final Office Action mailed Dec. 19, 2016", 11 pgs.
"U.S. Appl. No. 14/182,046, Corrected Notice of Allowance mailed Jan. 20, 2017", 6 pgs.
"U.S. Appl. No. 14/182,046, Notice of Allowance mailed Dec. 8, 2016", 7 pgs.
"U.S. Appl. No. 14/215,550, Final Office Action mailed Feb. 1, 2017", 11 pgs.
"U.S. Appl. No. 14/215,550, Response filed Dec. 5, 2016 to Non Final Office Action mailed Jul. 19, 2016", 13 pgs.
"U.S. Appl. No. 14/456,286, Notice of Allowance mailed Feb. 15, 2017", 9 pgs.
"U.S. Appl. No. 14/456,286, Response filed Nov. 16, 2016 to Non Final Office Action mailed Oct. 17, 2016", 9 pgs.
"U.S. Appl. No. 14/589,101, Advisory Action mailed Feb. 21, 2017", 5 pgs.
"U.S. Appl. No. 14/589,101, Examiner Interview Summary mailed Jan. 30, 2017", 3 pgs.
"U.S. Appl. No. 14/589,101, Response filed Jan. 23, 2017 to Final Office Action mailed Nov. 16, 2016", 9 pgs.
"U.S. Appl. No. 14/594,285, Non Final Office Action mailed Jan. 11, 2017", 15 pgs.
"U.S. Appl. No. 14/594,285, Response filed Dec. 14, 2016 to Restriction Requirement mailed Nov. 7, 2016", 8 pgs.
"U.S. Appl. No. 14/697,140, Non Final Office Action mailed Jan. 10, 2017", 12 pgs.
"U.S. Appl. No. 14/697,140, Response filed Nov. 16, 2016 to Final Office Action mailed Sep. 23, 2016", 13 pgs.
"U.S. Appl. No. 14/794,309, Non Final Office Action mailed Nov. 22, 2016", 13 pgs.
"U.S. Appl. No. 14/794,309, Response filed Feb. 22, 2017 to Non Final Office Action mailed Nov. 22, 2016", 12 pgs.
"U.S. Appl. No. 15/131,663, Preliminary Amendment filed Dec. 21, 2016", 6 pgs.
"U.S. Appl. No. 15/200,546, Preliminary Amendment filed Dec. 21, 2016", 6 pgs.
"U.S. Appl. No. 15/294,994, Preliminary Amendment filed Jan. 25, 2017", 8 pgs.
"U.S. Appl. No. 15/332,590, Preliminary Amendment filed Nov. 22, 2016", 5 pgs.
"U.S. Appl. No. 15/361,917, Preliminary Amendment filed Nov. 30, 2016", 6 pgs.
"U.S. Appl. No. 14/055,172, Notice of Allowance dated Mar. 29. 2017", 10 pgs.
"U.S. Appl. No. 14/094,311, Corrected Notice of Allowance dated Mar. 28, 2017", 5 pgs.
"U.S. Appl. No. 14/095,639, Notice of Allowance dated Apr. 13, 2017", 9 pgs.
"U.S. Appl. No. 14/095,639, Response filed Mar. 2, 2017 to Non Final Office Action dated Jan. 18, 2017", 9 pgs.
"U.S. Appl. No. 14/182,038, Notice of Allowance dated May 24, 2017", 9 pgs.
"U.S. Appl. No. 14/215,550, Corrected Notice of Allowance dated Jul. 27, 2017", 2 pgs.
"U.S. Appl. No. 14/215,550, Examiner Interview Summary dated Mar. 9, 2017", 3 pgs.
"U.S. Appl. No. 14/215,550, Notice of Allowance dated Jun. 21, 2017", 8 pgs.
"U.S. Appl. No. 14/215,550, Response filed May 1, 2017 to Final Office Action dated Feb. 1, 2017", 10 pgs.
"U.S. Appl. No. 14/594,285, Final Office Action dated May 22, 2017", 12 pgs.
"U.S. Appl. No. 14/594,285, Notice of Allowance dated Jun. 27, 2017", 10 pgs.
"U.S. Appl. No. 14/594,285, Response filed Apr. 11, 2017 to Non Final Office Action dated Jan. 11, 2017", 12 pgs.
"U.S. Appl. No. 14/594,285, Response filed Jun. 14, 2017 to Final Office Action dated May 22, 2017", 9 pgs.

(56) References Cited

OTHER PUBLICATIONS

"U.S. Appl. No. 14/599,909, Non Final Office Action dated Jul. 27, 2017", 18 pgs.
"U.S. Appl. No. 14/635,055, Response filed Jun. 27, 2017 to Restriction Requirement dated Apr. 27, 2017", 11 pgs.
"U.S. Appl. No. 14/635,055, Restriction Requirement dated Apr. 27, 2017", 7 pgs.
"U.S. Appl. No. 14/697,140, Final Office Action dated Jun. 30, 2017", 13 pgs.
"U.S. Appl. No. 14/697,140, Response filed Mar. 1, 2017 to Non Final Office Action dated Jan. 10, 2017", 11 pgs.
"U.S. Appl. No. 14/697,140, Response filed Jul. 27, 2017 to Final Office Action dated Jun. 30, 2017", 10 pgs.
"U.S. Appl. No. 14/794,309, Final Office Action dated Mar. 20, 2017", 18 pgs.
"U.S. Appl. No. 14/794,309, Non Final Office Action dated Jun. 20, 2017", 16 pgs.
"U.S. Appl. No. 14/794,309, Response filed May 22, 2017 to Final Office Action dated Mar. 20, 2017", 13 pgs.
"U.S. Appl. No. 14/956,724, Examiner Interview Summary dated Jun. 20, 2017", 3 pgs.
"U.S. Appl. No. 14/956,724, Non Final Office Action dated Mar. 31, 2017", 17 pgs.
"U.S. Appl. No. 14/956,724, Response filed Jun. 16, 2017 to Non Final Office Action dated Mar. 31, 2017", 12 pgs.
"U.S. Appl. No. 15/166,480, Supplemental Preliminary Amendment filed Jul. 18, 2017", 7 pgs.
"U.S. Appl. No. 15/288,183, Supplemental Preliminary Amendment filed Jul. 27, 2017", 7 pgs.
"U.S. Appl. No. 15/294,994, Supplemental Preliminary Amendment filed May 31, 2017", 6 pgs.
"U.S. Appl. No. 15/401,768, Preliminary Amendment filed Mar. 23, 2017", 6 pgs.
"U.S. Appl. No. 15/401,768, Supplemental Preliminary Amendment filed Jun. 22, 2017", 7 pgs.
"U.S. Appl. No. 15/412,676, Preliminary Amendment filed Jul. 3, 2017", 7 pgs.
"U.S. Appl. No. 15/455,895, Preliminary Amendment filed Mar. 13, 2017", 6 pgs.
"U.S. Appl. No. 15/461,675, Preliminary Amendment filed Jun. 24, 2017", 6 pgs.
"U.S. Appl. No. 15/622,718, Preliminary Amendment filed Jun. 15, 2017", 7 pgs.
"U.S. Appl. No. 15/662,572, Preliminary Amendment filed Jul. 31, 2017", 7 pgs.
"U.S. Appl. No. 15/664,572, Preliminary Amendment filed Aug. 3, 2017", 7 pgs.
"Chinese Application Serial No. 201480027708.4, Office Action dated Feb. 14, 2017", (W/ English Translation), 18 pgs.
"Chinese Application Serial No. 201480027708.4, Response filed May 2, 2017 to Office Action dated Feb. 14, 2017", (W/ English Translation), 17 pgs.
"European Application Serial No. 16168202.6, Partial European Search Report dated May 9, 2017", 12 pgs.
"U.S. Appl. No. 12/419,491, Examiner Interview Summary dated May 30, 2012", 3 pgs.
"U.S. Appl. No. 12/419,491, Examiner Interview Summary dated Nov. 29, 2011", 3 pgs.
"U.S. Appl. No. 12/419,491, Final Office Action dated Apr. 12, 2012", 12 pgs.
"U.S. Appl. No. 12/419,491, Non Final Office Action dated Sep. 22, 2011", 12 pgs.
"U.S. Appl. No. 12/419,491, Notice of Allowance dated Jul. 13, 2012", 10 pgs.
"U.S. Appl. No. 12/419,491, Response filed May 30, 2012 to Final Office Action dated Apr. 12, 2012", 12 pgs.
"U.S. Appl. No. 12/419,491, Response filed Dec. 9, 2011 to Non Final Office Action dated Sep. 22, 2011", 17 pgs.
"U.S. Appl. No. 12/788,966, Examiner Interview Summary dated Jun. 1, 2012", 3 pgs.
"U.S. Appl. No. 12/788,966, Final Office Action dated May 4, 2012", 16 pgs.
"U.S. Appl. No. 12/788,966, Non Final Office Action dated Jan. 4, 2012", 12 pgs.
"U.S. Appl. No. 12/788,966, Notice of Allowance dated Aug. 16, 2012", 10 pgs.
"U.S. Appl. No. 12/788,966, Notice of Allowance dated Nov. 23, 2012", 2 pgs.
"U.S. Appl. No. 12/788,966, Response filed Apr. 4, 2012 to Non Final Office Action dated Jan. 4, 2012", 15 pgs.
"U.S. Appl. No. 12/788,966, Response filed Aug. 6, 2012 to Final Office Action dated May 4, 2012", 12 pgs.
"U.S. Appl. No. 12/788,966, Response filed Dec. 16, 2011 to Restriction Requirement dated Dec. 7, 2011", 11 pgs.
"U.S. Appl. No. 12/788,966, Restriction Requirement dated Dec. 7, 2011", 9 pgs.
"U.S. Appl. No. 13/311,936, PTO Response to Rule 312 Communication dated May 10, 2016", 2 pgs.
"U.S. Appl. No. 13/791,014, Final Office Action dated Jan. 8, 2016", 11 pgs.
"U.S. Appl. No. 13/791,014, Non Final Office Action dated Aug. 14, 2015", 9 pgs.
"U.S. Appl. No. 13/791,014, Notice of Allowability dated Jul. 27, 2017", 2 pgs.
"U.S. Appl. No. 13/791,014, Notice of Allowance dated Jan. 10, 2017", 15 pgs.
"U.S. Appl. No. 13/791 014, Notice of Allowance dated Apr. 27, 2017", 8 pgs.
"U.S. Appl. No. 13/791,014, Response filed Jun. 6, 2016 to Final Office Action dated Jan. 8, 2016", 13 pgs.
"U.S. Appl. No. 13/791,014, Response filed Aug. 3, 2015 to Restriction Requirement dated May 1, 2015", 9 pgs.
"U.S. Appl. No. 13/791,014, Response filed Nov. 10, 2015 to Non Final Office Action dated Aug. 14, 2015", 13 pgs.
"U.S. Appl. No. 13/791,014, Restriction Requirement dated May 1, 2015", 6 pgs.
"U.S. Appl. No. 14/589,101, Non Final Office Action dated Sep. 14, 2017", 13 pgs.
"U.S. Appl. No. 14/599,909, Response filed Sep. 21, 2017 to Non Final Office Action dated Jul. 27, 2017", 10 pgs.
"U.S. Appl. No. 14/635,055, Non Final Office Action dated Aug. 28, 2017", 8 pgs.
"U.S. Appl. No. 14/697,140, Advisory Action dated Aug. 11, 2017", 3 pgs.
"U.S. Appl. No. 14/697,140, Notice of Allowance dated Sep. 5, 2017", 7 pgs.
"U.S. Appl. No. 14/794,309, Notice of Allowance dated Sep. 18, 2017", 5 pgs.
"U.S. Appl. No. 14/794,309, Response filed Aug. 17, 2017 to Non Final Office Action dated Jun. 20, 2017", 12 pgs.
"U.S. Appl. No. 14/854,308, Supplemental Preliminary Amendment filed Aug. 31, 2017", 3 pgs.
"U.S. Appl. No. 14/956,724, Notice of Allowance dated Aug. 23, 17", 9 pgs.
"U.S. Appl. No. 15/626,384, Preliminary Amendment filed Aug. 10, 2018", 11 pgs.
"U.S. Appl. No. 15/654,386, Preliminary Amendment filed Aug. 30, 2017", 11 pgs.
"U.S. Appl. No. 15/659,689, Preliminary Amendment filed Jul. 26, 2017", 7 pgs.
"U.S. Appl. No. 15/682,187, Preliminary Amendment filed Sep. 7, 2017", 6 pgs.
"U.S. Appl. No. 15/703,727, Preliminary Amendment filed Sep. 14, 2017", 7 pgs.
"U.S. Appl. No. 15/715,731, Preliminary Amendment filed Sep. 26, 2017", 9 pgs.
"Chinese Application Serial No. 201480027708.4, Office Action dated Aug. 18, 2017", (W/ English Translation), 8 pgs.
"European Application No, 16168202.6, Extended European Search Report dated Aug. 16, 2017", 11 pgs.
"European Application Serial No. 14716173.1, Response filed Sep. 25, 2017 to Office Action dated Mar. 14, 2017", 12 pgs.

(56) References Cited

OTHER PUBLICATIONS

U.S. Appl. No. 15/720,997, filed Sep. 29, 2017, Adjustable Knotless Loops.
U.S. Appl. No. 15/793,216, filed Oct. 25, 2017, Method and Apparatus for Coupling Soft Tissue to a Bone.
U.S. Appl. No. 15/722,002, filed Oct. 2, 2017, Scaffold for Spring Ligament Repair.
"U.S. Appl. No. 14/095,639, Notice of Allowance dated Oct. 30, 2017", 9 pgs.
"U.S. Appl. No. 14/589,101, Response filed Nov. 13, 2017 to Non Final Office Action dated Sep. 14, 2017", 10 pgs.
"U.S. Appl. No. 14/635,055, Response filed Nov. 28, 2017 to Non Final Office Action dated Aug. 28, 2017", 13 pgs.
"U.S. Appl. No. 14/854,308, Restriction Requirement dated Oct. 20, 2017", 8 pgs.
"U.S. Appl. No. 14/876,167, Restriction Requirement dated Nov. 22, 2017", 9 pgs.
"U.S. Appl. No. 14/936,831, Restriction Requirement dated Nov. 22, 2017", 8 pgs.
"U.S. Appl. No. 15/061,352, Non Final Office Action dated Nov. 17, 2017", 6 pgs.
"U.S. Appl. No. 15/074,553, Non Final Office Action dated Nov. 17, 2017", 6 pgs.
"U.S. Appl. No. 15/720,997, Preliminary Amendment filed Oct. 2, 2017", 6 pgs.
"U.S. Appl. No. 15/793,216, Preliminary Amendment filed Oct. 26, 2017", 8 pgs.
"Chinese Application Serial No. 201480027708.4, Response filed Oct. 31, 2017 to Office Action dated Aug. 18, 2017", No Translation, 3 pgs.
"European Application No. 16168202.6, Response filed Nov. 3, 2017 to Extended European Search Report dated Aug. 16, 2017", 9 pgs.
"U.S. Appl. No. 14/854,308, Response filed Dec. 20, 2017 to Restriction Requirement dated Oct. 20, 2017", 8 pgs.
"U.S. Appl. No. 14/936,831, Response filed Jan. 10, 2018 to Restriction Requiremnt dated Nov. 22, 2017", 6 pgs.
"U.S. Appl. No. 14/983,108, Response filed Jan. 24, 2018 to Restriction Requirement dated Dec. 24, 2017", 6 pgs.
"U.S. Appl. No. 14/983,108, Restriction Requirement dated Dec. 4, 2017", 7 pgs.
"U.S. Appl. No. 4/983,747, Response filed Jan. 24, 2018 to Restriction Requirement dated Dec. 20, 2017", 5 pgs.
"U.S. Appl. No. 14/983,747, Restriction Requirement dated Dec. 20, 2017", 7 pgs.
"U.S. Appl. No. 15/061,352, Notice of Allowance dated Jan. 19, 2018", 10 pgs.
"U.S. Appl. No. 15/061,352, Response filed Dec. 12, 2017 to Non Final Office Action dated Nov. 17, 2017", 9 pgs.
"U.S. Appl. No. 15/074,553, Notice of Allowance dated Jan. 19, 2018", 10 pgs.
"U.S. Appl. No. 15/074,553, Response filed Dec. 12, 2017 to Non Final Office Action dated Nov. 17, 2017", 8 pgs.
"U.S. Appl. No. 15/297,844, Supplemental Preliminary Amendment filed Jan. 25, 2018", 6 pgs.
"U.S. Appl. No. 15/715,731, Supplemental Preliminary Amendment filed Dec. 29, 2017", 8 pgs.
"U.S. Appl. No. 15/865,938, Preliminary Amendment filed Jan. 10, 2018", 7 pgs.
"U.S. Appl. No. 15/866,089, Preliminary Amendment filed Jan. 10, 2018", 10 pgs.
"Australian Application Serial No. 2014236885, First Examination Report dated Dec. 11, 2017", 2 pgs.

* cited by examiner

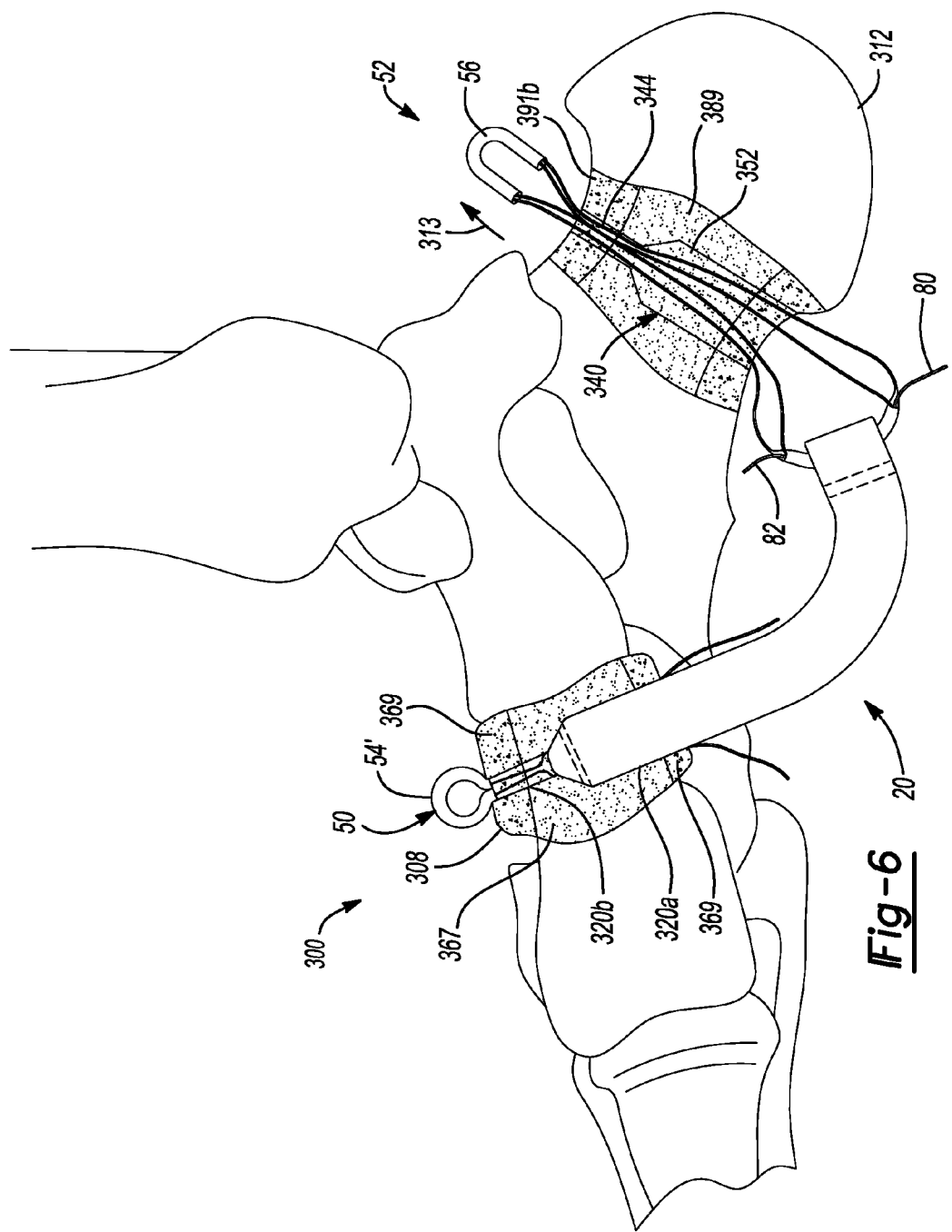

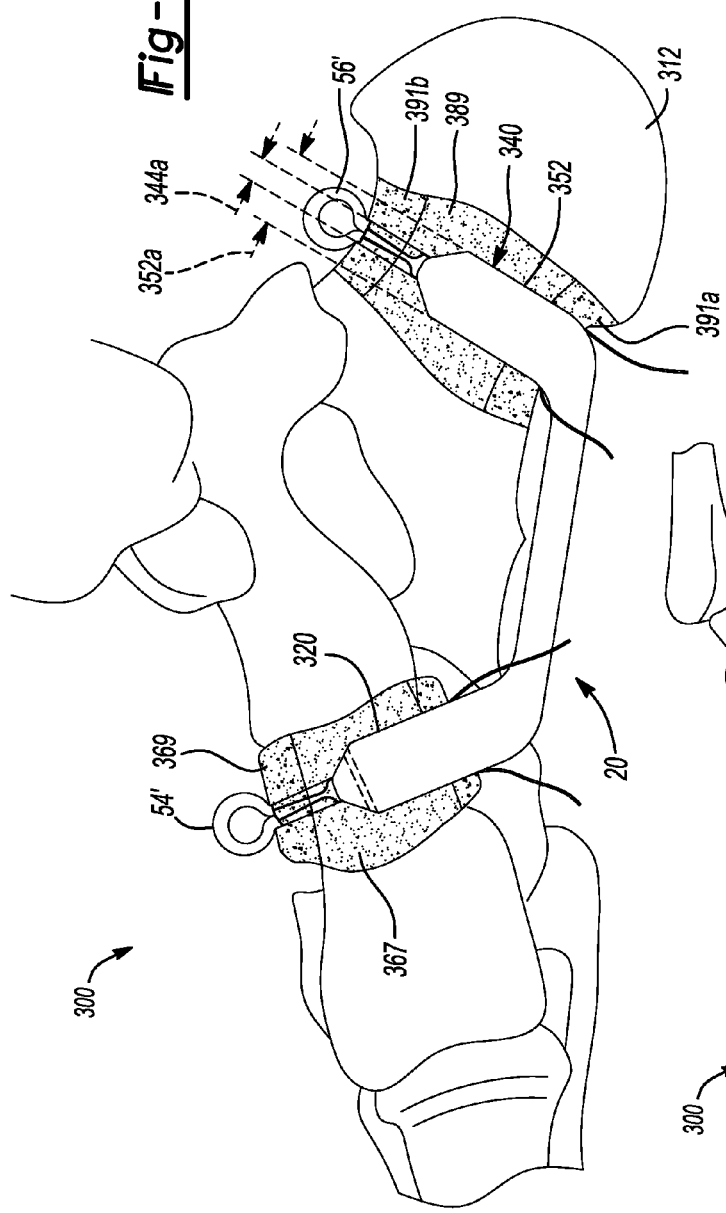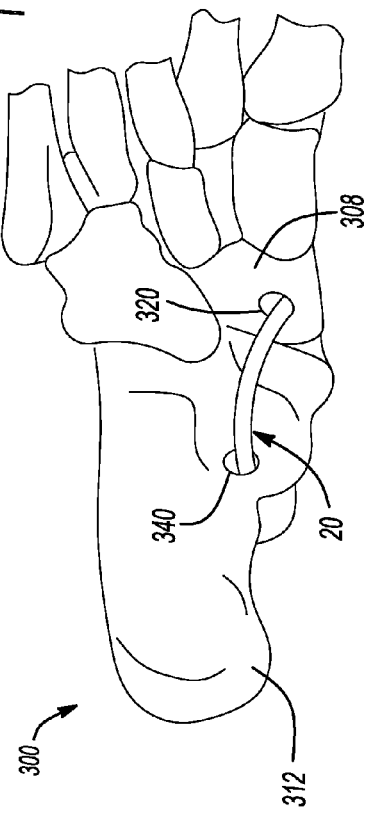

SCAFFOLD FOR SPRING LIGAMENT REPAIR

CROSS-REFERENCE TO RELATED APPLICATIONS

This application claims the benefit of U.S. Provisional Application No. 61/783,976, filed on Mar. 14, 2013.

This application is a continuation-in-part of U.S. patent application Ser. No. 14/055,191 filed on Oct. 16, 2013 and issued as U.S. Pat. No. 9,539,003 on Jan. 10, 2017, which is a divisional of U.S. patent application Ser. No. 13/098,897 filed on May 2, 2011 and issued as U.S. Pat. No. 8,562,645 on Oct. 22, 2013, which is a continuation-in-part of U.S. patent application Ser. No. 12/702,067 filed on Feb. 8, 2010 and issued as U.S. Pat. No. 8,672,968 on Mar. 18, 2014, which is a continuation of U.S. patent application Ser. No. 11/541,505 filed on Sep. 29, 2006 and issued as U.S. Pat. No. 7,658,751 on Feb. 9, 2010.

This application is a continuation-in-part of U.S. patent application Ser. No. 12/719,337 filed on Mar. 8, 2010 and issued as U.S. Pat. No. 9,078,644 on Jul. 14, 2015, which is a continuation-in-part of U.S. patent application Ser. No. 12/489,168 filed on Jun. 22, 2009 and issued as U.S. Pat. No. 8,361,113 on Jan. 29, 2013, which is a continuation-in-part of U.S. patent application Ser. No. 12/474,802 filed on May 29, 2009 and issued as U.S. Pat. No. 8,088,130 on Jan. 3, 2012, which is a continuation-in-part of (a) U.S. patent application Ser. No. 12/196,405 filed on Aug. 22, 2008 and issued as U.S. Pat. No. 8,128,658 on Mar. 6, 2012; (b) U.S. patent application Ser. No. 12/196,407 filed on Aug. 22, 2008 and issued as U.S. Pat. No. 8,137,382 on Mar. 20, 2012; (c) U.S. patent application Ser. No. 12/196,410 filed on Aug. 22, 2008 and issued as U.S. Pat. No. 8,118,836 on Feb. 21, 2012; and (d) U.S. patent application Ser. No. 11/541,506 filed on Sep. 29, 2006 and issued as U.S. Pat. No. 7,601,165 on Oct. 13, 2009.

The entire disclosure of the above applications are incorporated herein by reference.

FIELD

The subject disclosure is generally directed towards ligament repair and/or augmentation, and particularly to an augment construct that is configured to replace or augment a spring ligament in a foot.

BACKGROUND

This section provides background information related to the present disclosure which is not necessarily prior art.

A spring ligament is an anatomical ligament that interconnects various portions of a foot. Generally, the spring ligament may interconnect at least a navicular and a calcaneus. Various branches of the spring ligament, however, may also extend to connect or interconnect the calcaneus with the first cuneiform.

Injury to the spring ligament may lead to various issues, such as flat-foot deformities. Injuries to the spring ligament may not generally be diagnosed or repaired until various auxiliary issues present themselves, such as flat-foot deformities. Repairing a defect in the spring ligament, therefore, may lead to prevention of various afflictions.

SUMMARY

This section provides a general summary of the disclosure, and is not a comprehensive disclosure of its full scope or all of its features.

A ligament construct may be manufactured to repair or replace a selected ligament. For example, a spring ligament replacement or augment may include a synthetic scaffold that may be formed or manufactured to generally replace the spring ligament. The synthetic scaffold may be formed of polyester, polyethylene, resorbable materials, or combinations thereof. The synthetic scaffold may be formed of a woven or braided polyester or polyethylene material that is formed into selected configuration or shape to replace the spring ligament.

Selected suture anchoring systems and tensioning systems may be used to fixedly connect the ligament augment to the anatomy. For example, a Juggerknot™ soft anchor or suture anchor may be used to provide an anchor adjacent to or inside of a bone member. Alternatively, a ToggleLoc™ hard suture anchor may be used. A suture tensioning system, such as the Ziploop™ suture tensioning system may be used to draw the scaffold into the bone, and tension the augment relative to the bone while the Juggerknot™ anchor system is used to anchor the construct. It is understood, however, that the tensioning system may be used in combination with any appropriate anchor, such as an interference screw or other bone anchor system.

The scaffold may be used to replace the spring ligament. For example, a user may identify a spring ligament tear or removal from a bone portion and identify a need for an augment or ligament replacement. The spring ligament construct may then be fixed relative to the bone, such as with an appropriate anchor and tensioning system. The anchors may include the Juggerknot™ soft anchor system. The construct may then be maintained relative to the bone for a procedure and/or fixed to the remaining portion of the spring ligament to assist in augmenting the remaining spring ligament portions.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 6 is a side plan view of bones of a human foot illustrating a partial implantation of a ligament construct in a navicular bone and calcaneus bone;

FIG. 7A is a side plan view of bones of a human foot illustrating an implantation and tensioning of a ligament construct in a navicular bone and calcaneus bone;

FIG. 7B is a bottom plan view of bones of a human foot illustrating an implantation and tensioning of a ligament construct in a navicular bone and calcaneus bone;

Corresponding reference numerals indicate corresponding parts throughout the several views of the drawings.

DETAILED DESCRIPTION

Example embodiments will now be described more fully with reference to the accompanying drawings.

Figure 1A:
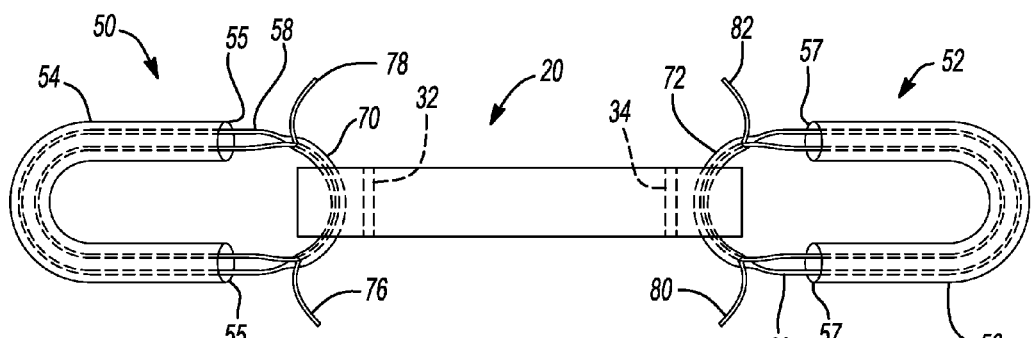
FIG. 1A is a top plan view of a ligament construct connected to suture, according to various embodiments.
Figure 1B:
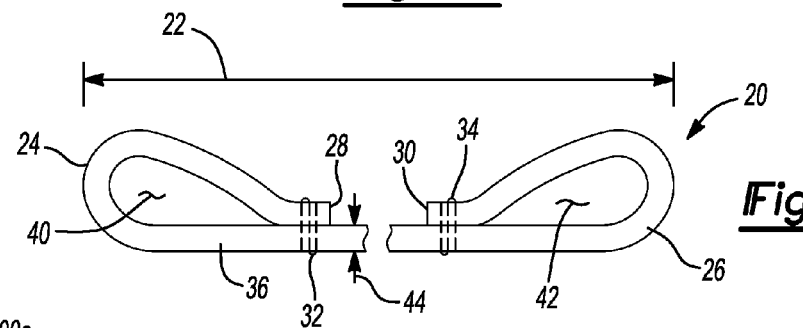
FIG. 1B is a side plan view of the ligament construct of FIG. 1A connected to suture.

With reference to FIGS. 1A and 1B, a ligament augment or replacement construct 20 is illustrated. The ligament construct 20 may be formed of selected materials, such as a woven or braided polyester or polyethylene material. Additionally, various absorbable materials may be included or used to form the construct 20, such as polylactic acid or other selected materials. The construct 20 may be formed of a woven material and/or formed of a solid material of a selected type. The construct 20, according to various embodiments, may be resilient with little to no elasticity. Thus, the length of the construct 20 may be selected and maintained during implantation. Also, the construct 20, therefore, may be tensioned and maintain a tension after implantation.

The construct 20 may include a selected length 22 that extends between a first end 24 and a second end 26. The two ends 24, 26 may be formed by folding terminal end regions 28 and 30 over and towards a center of the construct 20. The terminal ends 28, 30 may be folded onto a body portion 36 of the construct 20. The terminal ends 28, 30 may be stitched, sonically welded, or otherwise fixed with a mechanism 32, 34 to the main body portion 36 of the construct. The folding over of the terminal ends 28, 30 may form passages, also referred to as eyelets, a loop, or open regions 40 and 42 near the ends 24, 26 of the construct 20. The passages, as discussed herein, may be engaged or coupled to sutures and/or anchor members.

The main body portion, or selected portions of the construct 20, may have a thickness 44 based upon various characteristics of the construct 20, such as strength, rigidity, elasticity, and the like. Moreover, it is understood that if the construct 20 is formed of a braided, woven, or other appropriate material that the thickness 44 may decrease under a load between the two eyelet portions 40, 42. The thickness 44, however, may be defined by one or more strands of a woven material According to various embodiments, the eyelets 40, 42 may be formed around suture and one or more suture constructs including a first suture construct 50 and a second suture construct 52; and/or the suture constructs 50, 52 may be formed within the eyelets 40, 42 and around the construct 20. The suture constructs 50 and 52 may be separate, but substantially identical and interconnected with the separate eyelets 40, 42 for fixation of the construct 20 relative to a selected anatomy, as discussed further herein. The suture constructs 50, 52 may be similar to the suture constructs disclosed in U.S. Pat. No. 8,118,836, issued Feb. 21, 2012; U.S. Pat. App. Pub. No. 2011/0098727, published on Apr. 28, 2011; or U.S. Pat. App. Pub. No. 2012/0095470, published on Apr. 19, 2012; all incorporated herein by reference.

Generally, the suture constructs may include respective anchors that may be formed as tubes 54, 56 through which a suture or selected filament 58, 60 passes. The suture 58, 60, when acted upon by a user, may cause the tubes 54, 56 to form an anchoring mass as knots or soft anchors to hold the construct 20 in a selected position. The anchoring mass can be formed on an exterior surface of a bone or formed within a bone surface, as discussed further herein. The suture anchors may include the Ziploop™ constructs to allow for slip tensioning of a portion positioned relative to the Ziploop suture construct and a Juggerknot™ anchor portion that may be formed by the respective tubes 54, 56. Each of the Ziploop™ suture construct and the Juggerknot™ soft anchor portion are sold by Biomet, Inc.

The sutures 58, 60 may further pass through a body or passage portion 70, 72 where two suture ends of each suture construct 50, 52 extend from the respective passage portions 70, 72. Each of the sutures 50, 52 has the respective passage portion 70, 72 and each defines a respective through-passage through the passage portions 70, 72. Each suture construct 50, 52 further has two ends 76, 78 and 80, 82. For each suture construct the first end 76, 80 is passed into the through-passage through a first aperture to form a first loop and exits the through-passage through a second aperture and the second end 78, 82 is passed into the through-passage through a third aperture to form a second loop and exits the through-passage through a fourth aperture. It is understood, according to various embodiments, the first and third aperture may be the same aperture as may be the second and fourth aperture. Thus, each passage portion may include 2, 3, or 4, or a selected number of apertures into the through-passage of the passage portion. Each of the two suture ends 76, 78 and 80, 82 may be acted upon by a user to collapse the respective anchors 50, 56 to form the soft anchoring masses and tension the construct 20 between two points of the anchors 54 and 56, as discussed further herein.

The anchor assemblies 50, 52 including the anchors 54, 56, also referred to as tubes, which may generally include a collapsible tube that is a closed loop of suture material that is formed into the tube shape. According to various embodiments, the tube assembly 54, 56 may be slideable relative to the suture loops or filaments 58, 60. Briefly, although disclosed in the U.S. Pat. No. 8,118,836, incorporated herein by reference, the suture assemblies 50, 52 may include the suture portions 58, 60 that pass through openings 55, 57 of the respective tubes 54, 56. Alternatively, the suture portions may pass out an aperture that is not at the openings 55, 57 such that one or both ends of the tubes 54, 56 form flaccid or unbound ends.

Generally, the suture portions 58, 60 may be single or continuous suture filaments that extend through the respective tubes, 50, 56 in the respective braided bodies 70, 72 of the suture assemblies 50, 52. The suture assemblies 50, 52, therefore, may be manipulated by a user to generate a soft anchor, as discussed herein, by collapsing the respective tubes 50, 56, and tensioning the construct 20 relative to selected areas of a subject by moving the ends 76-82 to tension the construct 20 relative to the respective anchors formed by the tubes 54, 56. The anchors 54, 56 collapse under a force, such as a tensile force, provided by or through the respective suture portions 58, 60 to form soft or anchor masses in respective areas, as discussed further herein. The tubes 54, 56 may form the anchors by collapsing the tubes 54, 56 relative to a positive or adjacent surface of the tube 54, 56.

Figure 2A:
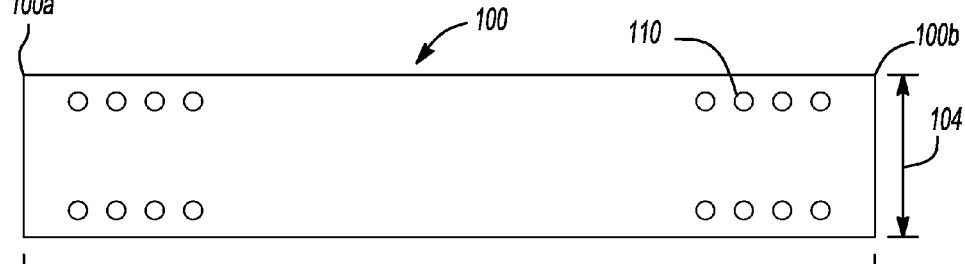
FIG. 2A is a top plan view of a ligament construct according to various embodiments.
Figure 2B:
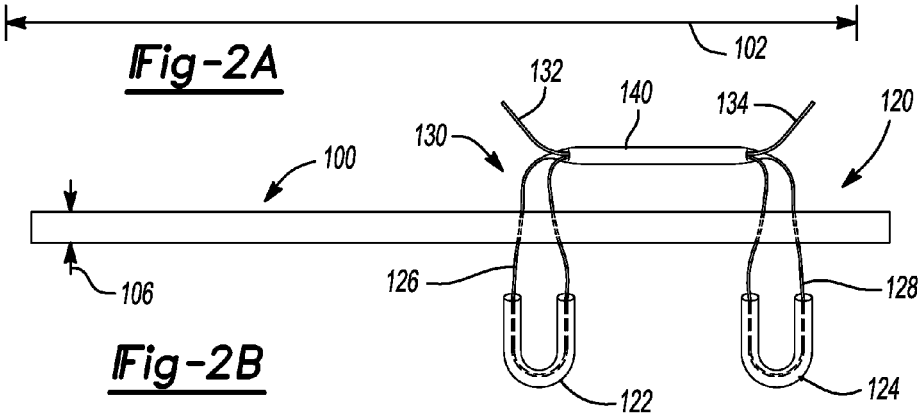
FIG. 2B is a side plan view of the ligament construct of FIG. 2A connected to suture.

With reference to FIGS. 2A and 2B, a construct 100 is illustrated. The construct 100 may be similar to the construct 20 in general construction. For example, the construct 100 may be formed of a woven selected material, such as polyester or polyethylene. Additionally, the construct 100 may be formed from a selected material including bioabsorbable materials that may be absorbed into a selected anatomy over time and allow for ingrowth of various tissues to replace portions of the construct 100.

The construct 100, however, may also be formed in a substantially elongated and rectangular construct including a length 102 from a first end 100a to a second end 100b of about 4 centimeters (cm) to about 10 cm, and further including 4 cm to about 8 cm. Additionally, the construct 100 may include a width 104 that is about 0.5 cm to about 4 cm, including about 1-3 cm, and further including about 1 cm to about 2 cm. The construct 100, as illustrated in FIG. 2B, may further include a thickness 106 that is about 0.5 millimeters (mm) to about 4 mm, and further including about 1 mm to about 3 mm.

The construct 100 may include one or more bores 110 formed from a first side to a second side through the thickness 106 of the construct 100. The bores 110 may be formed in a selected configuration, such as near a perimeter of the construct 100. The bores 110 are generally formed at or near both of the ends 100a, 100b of the construct 100. Thus, the ends 100a, 100b of the construct 100 can be engaged and tensioned relative to selected anchoring regions, as discussed herein. The bores 110 may allow for passage of selected anchor assemblies, such as an anchor assembly 120, as discussed further herein. Any appropriate anchoring assembly, such as the construct 50, however, may also be used.

The anchor assembly 120 may pass through one or more of the throughbores 110 to allow for fixation of the construct 100 relative to a selected subject. The bores 110 may be throughbores formed through the construct 100 through various techniques such as puncturing, drilling, ultrasonic welding or puncturing, or other appropriate mechanisms. Also, the through bores 110 may be formed between braided or woven fibers of the construct 100. Regardless, the bores 110 may be throughbores formed through the entire thickness 106 of a construct 100 to allow for passage of anchor assemblies 120.

The anchor assembly 120 may be an anchor assembly including an anchor assembly as disclosed in U.S. Pat. No. 8,118,836, incorporated herein by reference. The anchor assembly 120 may include various portions similar to the anchor assemblies 50, 52 described above. Generally, the anchor assembly 120 may include a first collapsible anchor 122 (also referred to as a tube) and a second collapsible anchor 124 (also referred to as a tube) which are disposed about or around respective suture loops 126 and 128 that are a part of a single elongated suture of the anchor assembly 120. As tension is applied on the respective suture loops 126, 128, the anchors 122, 124 collapse and may form anchoring masses relative to selected portions of a subject, similar to the anchors 54, 56 discussed above. It is understood that the respective suture anchors 122, 124 may be collapsed simultaneously and/or at staggered times, as selected and/or desired by a user.

The suture loops 126, 128 are portions of a suture 130 that further include suture ends 132 and 134. The suture ends may be gasped or manipulated by a user to collapse the tubes 122, 124 to form the soft anchors. Additionally, the suture 130 may be passed through a passage portion 140 having a through-passage as discussed above and as disclosed in U.S. Pat. No. 8,118,836, incorporated herein by reference. The suture ends 132, 134 may be manipulated to move the passage portion 140 relative to the tubes 122, 124. As discussed above, the movement of the passage portion 140 relative to the tubes 122, 124 may tension the construct 100 relative to the tubes 122, 124 when the tubes are collapsed against a respective positive surface, such as a bone surface. Accordingly, the construct 100 may be tensioned relative to a bone surface as discussed further herein by pulling on the ends 132, 134 of the suture loop 130.

Figure 3:
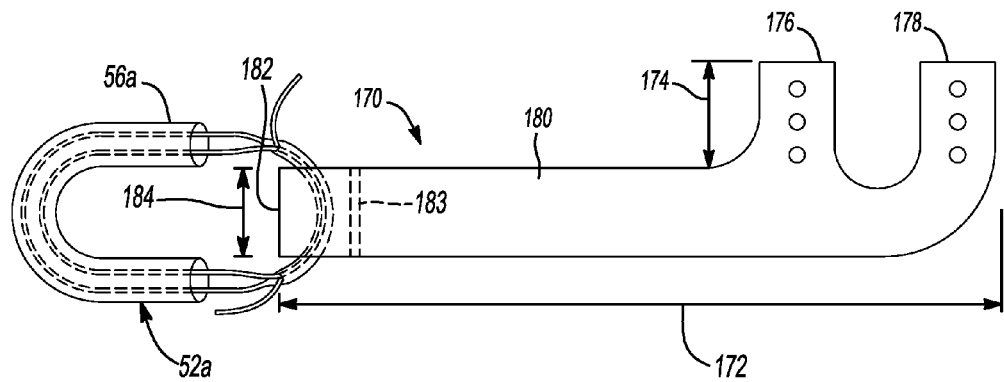
FIG. 3 is a top plan view of a ligament construct according to various embodiments.

With reference to FIG. 3, a construct 170, according to various embodiments, is illustrated. The construct 170 may include various dimensions, such as a length 172 that may be about 3 cm to about 10 cm, including about 4 cm to about 8 cm. The construct 170 may further include a height 174 that includes a selected height of about 1 cm to about 4 cm, including about 2-3 cm. The height 174 may include a height or a length of arm portions 176 and 178 that extend from a main body portion 180 of the construct 170. The main body portion 180, however, may include an end 182 that may include a height 184 having a dimension of about 0.5 cm to about 2 cm, and further including a height of about 1 cm.

The construct 170 may be similar in construction to the constructs 20 and 100, as discussed above. Accordingly, the construct 170 can include any selected portion to interconnect with a suture and/or anchor assembly. For example, an eyelet can be formed near the terminal ends of the construct and/or throughbores may be formed through the construct 170. For example, a suture construct 52a that includes an anchor 56a can be coupled to an eyelet formed by folding over a terminal end and fixing it with a fixing structure 183 near the first end 182. The suture construct can be similar or identical to the suture construct 52. It is understood that each arm 176, 178 can include a fold formed eyelet and one or more throughbores and individual coupled suture constructs, according to various embodiments.

The construct 170, however, may include the single end 182 and the two arms 176 and 178 extending from an area at the second end of the construct 170. As discussed herein, the first end 182 may engage a first bone member or portion while the two arms 176 and 178 may engage separate bone members or constructs as discussed herein. Thus, at each arm 176, 178 and the first end 182 a suture construct including an anchor portion can be connected. Fixation of the construct 172 to selected bone portions may include various suture anchors and assemblies 50, 52 and 120 as discussed above. Accordingly, the construct 170 may be fixed relative to a selected portion of a subject similar to the fixation or anchoring mechanisms as discussed above.

Figure 4:
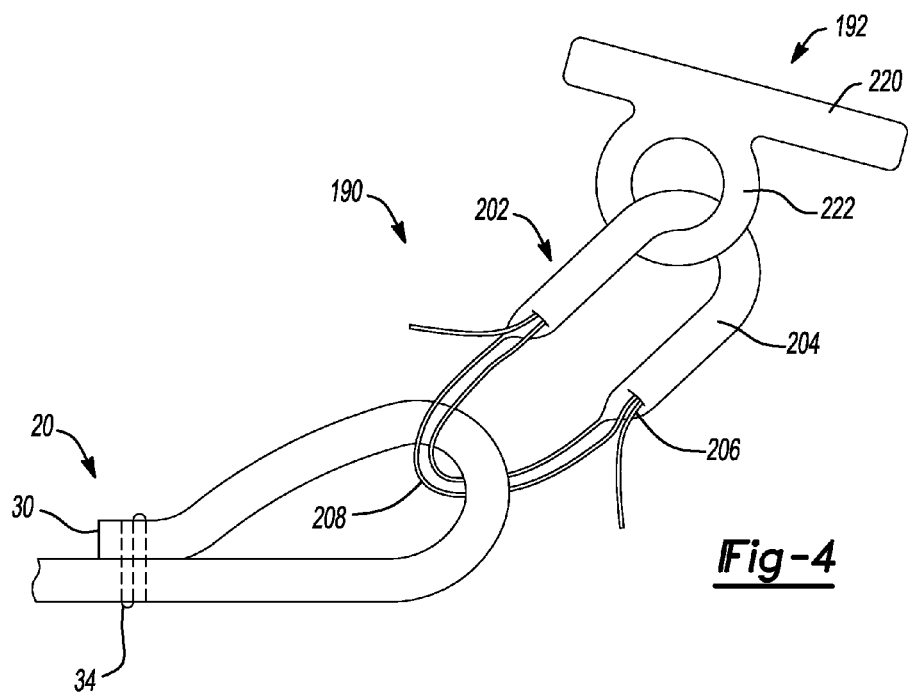
FIG. 4 is a detail view of a portion of a ligament construct connected to a suture and an anchor, according to various embodiments.

With reference to FIGS. 1A-1B, discussed above, and additional reference to FIG. 4, the construct 20, or construct according to various embodiments as discussed above, may be engaged or associated with an anchor assembly 190. The anchor assembly 190 may include a fixation member 192, such as a Toggleloc™ anchor, sold by Biomet, Inc., that is rigid. The rigid fixation member 192 may include that illustrated and disclosed in U.S. Patent Application Publication No. 2012/0116452 and U.S. Pat. No. 7,695,503, both incorporated herein by reference. In addition, the anchor 192 may be interconnected or associated with a suture assembly 202, similar to the suture assemblies 50, 52 discussed above. The suture assembly 202 may include a passage portion 204 to which a continuous suture 206 is passed. The continuous suture 206 may include a continuous loop of suture that passes through the passage portion 204. The passage portion 204 may be formed through the anchor 192, as illustrated in FIG. 4.

The construct 20 may also be formed around the filament or loop portions of the suture portion 208 to engage the construct 20 relative to the anchor 192. The construct 20 may have the eyelet 42 formed by suturing or interconnecting an end 30 of the construct 20 with a suture portion 34. The construct 20, therefore, may be held relative to the anchor 192 with the suture assembly 202. Generally, the anchor 192 may include an elongated arm portion 220 and an eyelet or interconnection portion 222 to engage the suture assembly 202.

Accordingly, it is understood that the construct, according to various embodiments including the construct 20, the construct 100, and the construct 170, may be interconnected with a selected anchor or connecting portion. The connecting portion may include soft anchors, such as those illustrated with the suture assembly 50 or the suture anchor assembly 120. Additionally, a hard or rigid fixation member may include the fixation member 192 illustrated in FIG. 4.

Figure 5:
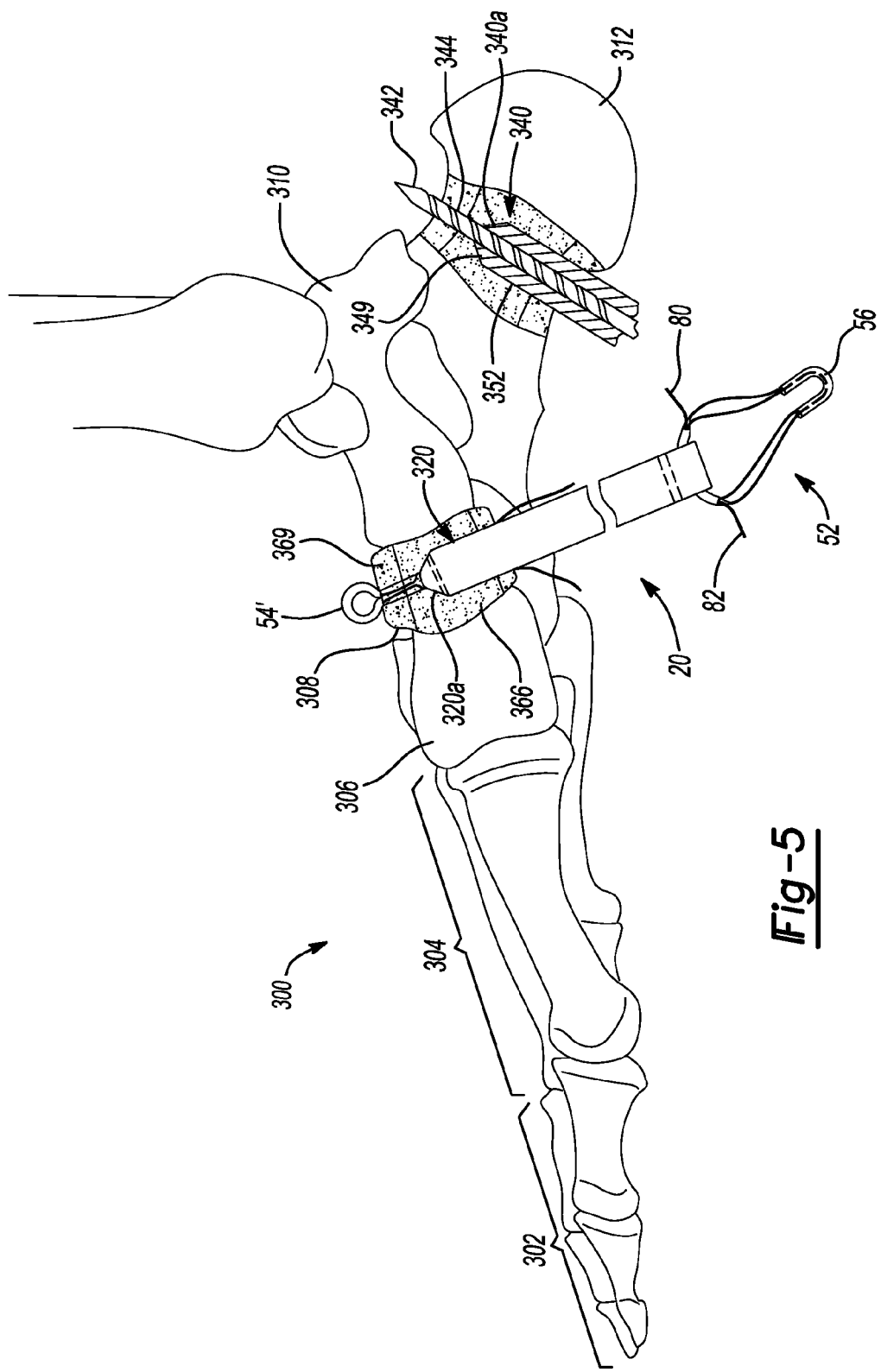
FIG. 5 is a side plan view of bones of a human foot illustrating a partial implantation of a ligament construct in a navicular bone.

The ligament construct, according to various embodiments as discussed above, may be provided relative to a selected portion of a subject, such as a foot 300 of a subject, illustrated in FIG. 5. The foot 300 of the subject may include various anatomical bone portions, such as those generally known in the art. For example, the foot 300 may include phalange members 302, metatarsal members 304, a medial (first tarsal) cuneiform 306, a navicular 308, a talus 310, and a calcaneus 312. The foot 300 may be connected or articulated with other boney portions, such as a tibia and a fibula, as is generally understood in the art.

With additional reference to FIG. 5, the various boney portions of the foot 300 may be interconnected with a construct, including the various embodiments of a construct as discussed above. For exemplary purposes, the construct 20 is illustrated and discussed. It is understood, however, that the construct 100 may be used relative to the foot 300 including the suture assembly 50, 52 and/or the anchor suture assembly 120, as discussed above. Nevertheless, for illustration of a selected procedure to replace a spring ligament or augment a spring ligament in a foot 300, the construct 20 is discussed further herein.

As illustrated in FIG. 5, the navicular 308 may be configured to include a throughbore 320 through which the anchor 54 may be passed and collapsed upon an exterior bone surface of the navicular 308 to form the anchoring mass or portion 54', such as a soft anchor, relative to the navicular bone 308. The anchor portion 54' may be defined as a large or anchoring mass formed near the bone surface. A locking profile of the tube 54 may allow the anchoring mass to be formed by the application of a tensile force with the suture 58. The bore 320 may be formed to allow for passage and receipt of at least a portion of the construct 20 into a portion of the bore 320. The drawing or tensioning of the construct 20 into the bore 320 may be performed with the suture assembly 52 by drawing or tensioning the suture ends 76, 78 and drawing the construct 20 into the bore 320. The formation of the bore 320 and tensioning of the construct 20 into the bore 320 will be discussed further in relation to the calcaneus 312 in a bore 340 formed therein, discussed further herein.

With a continuing reference to FIG. 5, the calcaneus 312 may have a bore 340 formed therein including a plurality of diameters. For example, a first or small drill/pin 342 may be passed through or drilled through the calcaneus 312 to form a small bore or first bore passage 344. A second or larger drill bit 349 (the larger drill bit 349 may be cannulated) may be passed over the small bit 342 to form a second or larger bore 352. Accordingly, the bore 340 formed through the calcaneus 312 may include a first diameter bore 344 and a second diameter bore 352. The bore 320 formed in the navicular 308 may include a similar large diameter bore portion and a small diameter bore portion. The large diameter bore portion may receive a portion of the construct 20 while the small diameter bore portion may allow for passage of the suture construct 50, 52 to allow for movement of the respective tubes 54, 56 to a second portion of the respective bone to form the soft anchor relative thereto. Moreover, a shoulder or ledge 320a, 340a is formed within the respective bores 320, 340 due to the different diameters.

With reference to FIG. 6, the anchor assembly, including the suture anchor assembly 52 that is connected to an end of the construct 20, may be passed through the bore 340 formed to the calcaneus 312, or selected bone portion. The suture assembly 52 and/or only the anchor 56 alone may be passed through the bore 340. An appropriate passing member may interconnect with the anchor 56 and/or the suture ends 80, 82 to push or pull the suture assembly through the bore 340 formed to the calcaneus 312. The construct 20 interconnected with the suture anchor assembly 52, however, may be moved relative to the calcaneus 312 to allow for passage of the suture anchor assembly 52 through the bore 340 formed through the calcaneus 312.

As illustrated in FIG. 6, the construct 20 may be pulled into the bore 320 formed in the navicular 308 and the anchoring portion 54' may be formed relative to the navicular 308 by tensioning the anchor 54 relative to the navicular 308, as is generally understood in the art. The suture assembly 52 may then be moved through the bore 340 formed through the calcaneus 312, as illustrated in FIG. 6. It is understood, however, that the suture assembly 52 may be first passed through the calcaneus 312 prior to passage of the suture assembly 50 through the navicular 308. The order of placing the anchors relative to individual bone portions is exemplary, and not intended to be limiting. After forming the bore 340 through the calcaneus 312, the suture assembly 52 may be passed through the calcaneus 312. According to various embodiments, the anchors, including the soft anchors, can be formed on the surface of the bone portions at all selected anchoring points. Then each end of the construct can be alternatingly tightened to substantially ensure uniform tensioning of the construct 20.

The passage of the suture assembly 52 through the calcaneus 312 may generally be in the direction of arrow 313. The passage of the suture assembly 52 may be according to appropriate mechanisms, such as pulling the suture assembly 52 through the bore 340 or pushing the suture assembly 52 through the bore 340. Generally, however, the anchor 56 may be passed through a distal cortical bone portion 391a, as illustrated in FIG. 7A, and a second cortical bone portion 391b, is also illustrated in FIG. 7A. The bore 340 may further be formed through both of the cortical bone portions 391a and 391b and further through the cancellous bone portion 389, therebetween.

Accordingly, a soft anchor may be formed by the anchor 56 on an exterior distal surface of the cortical bone portion of the calcaneus 312. The anchor 56 may be formed by drawing the construct 20 into the large bore portion 352, by manipulating the ends of the suture filaments 80, 82, to form the soft anchor 56'. The construct 20 may then be tensioned and drawn into the bore 340.

With continuing reference FIGS. 5 and 6, and additional reference to FIGS. 7A and 7B, the construct 20 may be tensioned into the bore 320 formed within the navicular 308 and the bore 340 formed in the calcaneus 312. The bore 320 in the navicular 308 may include a large bore portion 320a and a small bore portion 320b similar to the large bore 352 and the small bore portion 344 formed through the calcaneus 312. The large bore portion, of both the navicular 308 and the calcaneus 312, may include a diameter 352a such as about 4 mm to about 6 mm. The small bore portion of both the calcaneus 312 and the navicular 308 may include a diameter 344a of about 2 mm to about 4 mm. It is understood, however, that the bore formed through the respective bone portions may be any appropriate diameter to receive the constructs positioned within the respective bore portions and interact with the anchor members positioned relative to the bone portions.

The anchor portion 54' formed by the tube 54 and anchor portion 56' formed by the tube 56 may be formed on an exterior surface of the bone portions 308, 312 such as on an exterior surface of the cortical bone thereof. The anchor portions 54', 56' can fix or anchor the construct 20 relative to the bone portions. The anchor portions 54', 56' may be defined as a large or anchoring mass formed near the bone surface. A locking profile of the tubes 54, 56 may allow the anchoring mass to be formed by the application of a tensile force with the suture 58, 60. The construct 20 may then be tensioned relative to the anchor portions 54', 56' to form a selectively tensioned construct 20 relative to the two bones of the navicular 308 and the calcaneus 312 to augment or replace the spring ligament.

The soft anchors 54', 56' however, may be formed within the respective bone portions 308 and 312 relative to a cancellous bone portions 389 and 367 to engage the proximal cortical bone portions 391b and 369 of the respective bone members 308 and 312. Accordingly, the soft anchor portions 54', 56' need not be formed on the exterior surface of the respective bone member 308 and 312 to anchor the construct 20 relative to the respective bone portions 308 and 312. Rather, the bone anchors or construct anchors may be formed within the bone surfaces to provide for fixation of the construct 20 relative to the respective bone members 308 and 312. Formation of an anchor assembly within the bone member may be formed as discussed above and with an anchor assembly as disclosed in U.S. Patent Application 2011/0098727, published Apr. 28, 2011, incorporated herein by reference. The formation of the soft anchor 54', 56' may be substantially similar, save that the soft anchor is formed within the tunnel 340 and 320 of the respective bone members.

Figure 8:
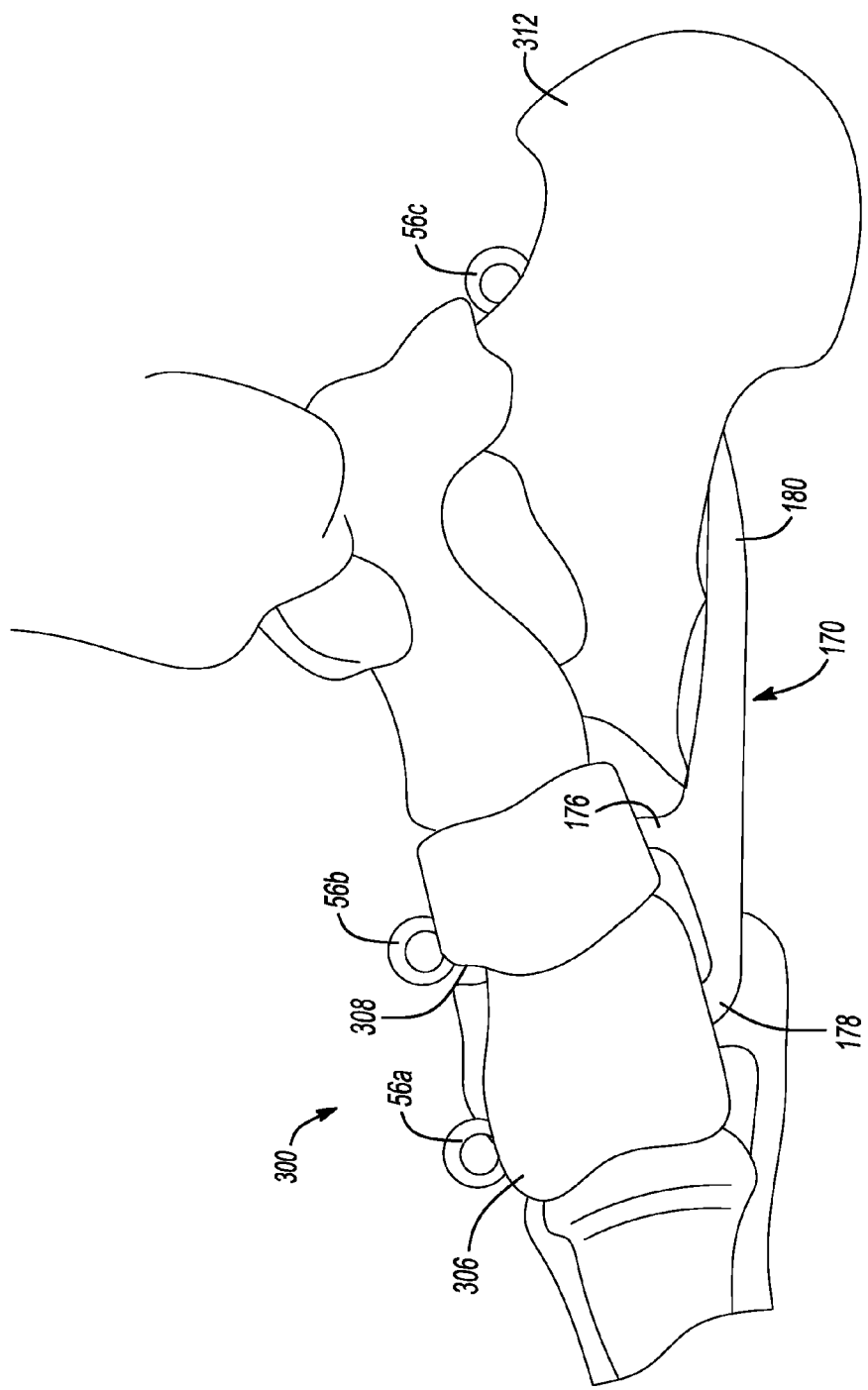
FIG. 8 is a side plan view of bones of a human foot illustrating an implantation and tensioning of a ligament construct in a cuneiform, a navicular bone, and a calcaneus bone, according to various embodiments.

The construct 20 may be positioned relative to respective bone portions, such as the calcaneus 312 and navicular 308, as discussed above and illustrated in various figures, including FIGS. 6-7B. The construct 100 may be similarly positioned between two selected bone portions, such as the calcaneus 312 and navicular 308. According to various embodiments, the construct 170 may be interconnected with two or more bones portions of the foot 300, as illustrated in FIG. 8. The construct 170, including the main body portion 180, the arm member 178, and the arm member 176 may be connected or positioned relative to the navicular 308 and the first cuneiform 306. Additionally, the end of 182 of the main body 180 may be positioned relative to the calcaneus 312 of the foot 300.

The fixation of the construct 170 relative to the respective bone portions may be with the suture anchor construct, such as the suture anchor construct 52. Accordingly, each of the ends of the construct 170 may be coupled to bone portions with a suture anchor such as the suture anchor at 56a relative to the first cuneiform, a suture anchor 56b relative to the navicular 308, and a suture anchor 56c relative to the calcaneus 312. It is understood, however, that the various anchor of fixation members may be positioned relative to the respective boney members, including the first cuneiform 306, navicular 308, and the calcaneus 312, to fix the construct 170 relative thereto. For example, the suture anchor assembly 120 may be interconnected with the construct 170 to anchor relative to the selected bone portions in addition to the anchor fixation member 190, as illustrated in FIG. 4.

Accordingly, a ligament construct may be provided to augment and/or replace the spring ligament. The ligament construct, therefore, can interconnect various portions of the foot 300, including the calcaneus 312 and the navicular 308. In various embodiments, the first cuneiform 306 may also be interconnected relative to the navicular 308 and the calcaneus 312. The interconnection of the respective boney portions of the foot 300 may be provided to augment or replace the spring ligament of the foot 300. The spring ligament to the foot 300 may be further augmented by interconnecting the respective construct, such as the construct 20 or the construct 170, with the spring ligament. The interconnection of the construct relative to the spring ligament may be provided by further suturing the construct to the spring ligament. For example, the construct may be sutured directly to the spring ligament by generally known suture techniques such as threading or knotting the appropriate construct to a portion of the spring ligament that is remaining in the foot 300. For example, the spring ligament may be interconnected by the navicular bone 308 portion and the augment may be sutured to the spring ligament that remains connected at the bone portion. Accordingly, it is understood that the construct, as discussed above, may be provided to replace or augment the spring ligament in the foot 300. Moreover, the construct may be interconnected with a respective bone portion of the foot 300, according to various embodiments, including those discussed above. The construct, such as the construct 20, the construct 100, or the construct 170 may be formed through various weaving and molding techniques to provide an appropriate construct to replace or augment the spring ligament in the foot 300.

Figure 9:
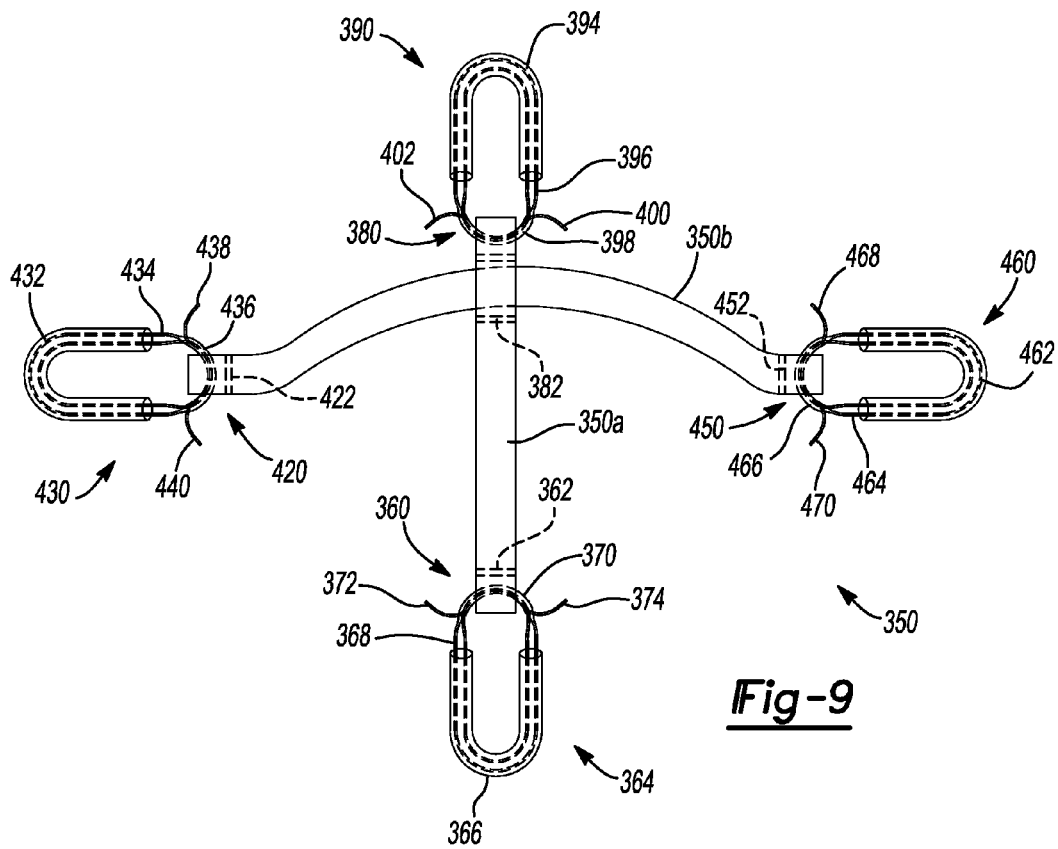
FIG. 9 is a top plan view of a ligament construct connected to a suture, according to various embodiments.
Figure 10:
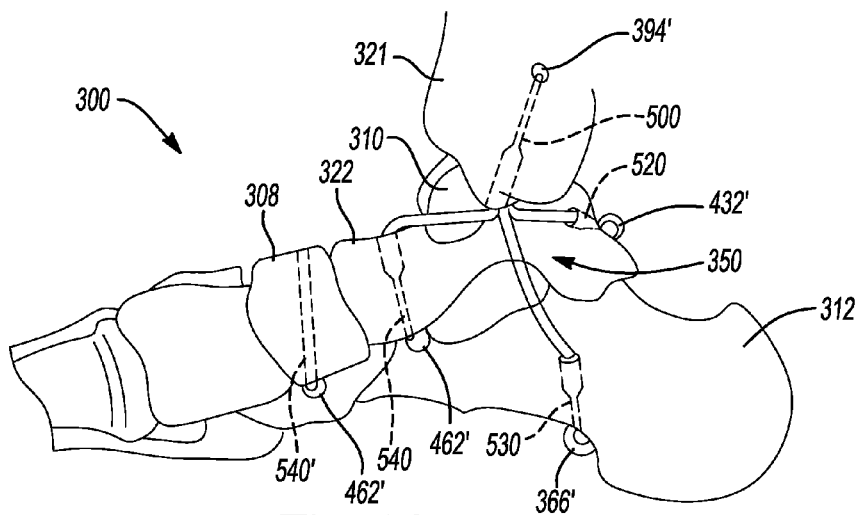
FIG. 10 is a side plan view of bones of a human foot illustrating an implantation and tensioning of a ligament construct in a navicular bone, talus bone, and calcaneus bone, according to various embodiments.

With reference to FIGS. 9 and 10, a deltoid ligament in the foot 300 can interconnect a tibia 321 relative to the foot 300. The deltoid ligament can interconnect the tibia 320 relative to the calcaneus 312, the navicular 308, and a talus 322. The tibia 321, the talus 322, the navicular 308 and the calcaneus 312 can be interconnected with a construct 350, as illustrated in FIG. 9. The ligament construct 350 can include construct bodies 350a and 350b that are formed similar to the ligament construct 20, as discussed above. Accordingly, the construct bodies 350a and 350b can be formed as substantially elongated members extending between first and second respective ends and can be formed of a woven polymer material and/or a solid material.

According to various embodiments, the first construct body 350a can extend from a first end 360 that has a first eyelet formed by folding over and fixing (e.g. via suturing or sonically welding) with a fixing member or system 362 a terminal end of the main body to an internal position of the body 350a. Positioned through the eyelet at the first end 360 can be a first suture construct 364. The first suture construct 364 can be similar to the suture construct 50 discussed above, and will not be described here in detail. Nevertheless, the suture construct 364 can include a collapsible tube 366 that is formed around a suture 368 that passes through a passage portion 370 with first and second suture ends 372 and 374 extending therefrom. As discussed above, the suture construct 364 can be positioned relative to a bone portion, as discussed further herein, to allow the collapsible tube 366 to form an anchoring mass by drawing or pulling on the suture end 372 and 374.

The first construct body 350a may extend from the first end 360 to a second end 380 that also has an eyelet that may be formed by fixing a terminal end at the second end 380 with a fixation portion 382. A second suture construct 390 can also be passed through the eyelet that includes a collapsible tube 394 formed around a suture 396. The suture 396 can have a passage portion 398 through which the suture passes and a first end 400 and a second end 402 extends therefrom. Again, the suture construct 390 can be used to tension and anchor the first body 350a relative to selected boney portions, as discussed further herein.

Additionally, passed or formed through the eyelet at the second end 380 can be the second construct body 350b. The second construct body 350b can extend from a first end 420 that forms an eyelet by having a terminal end portion fixed a distance from the terminal end with a fixation mechanism 422. Passed through the eyelet formed at the first end 420 can be a third suture construct 430, similar to the suture constructs 364 and 390. Accordingly, the suture construct 430 can include a collapsible tube 432 that is formed around a suture 434 that passes through a passage body or portion 436 with a first terminal end 438 and a second terminal end 440 extending therefrom. Again, the suture construct 430 can be used to fix or anchor the second body portion 350b by forming the collapsible tube 432 into an anchor mass by pulling on the terminal suture ends 438 and 440.

The second construct body 350b may extend from the first end 420 to a second end 450 that may also include a second eyelet formed by fixing a terminal end a distance from the terminal end with a fixation portion 452. A fourth suture construct 460 can also be passed through the eyelet formed at the second end 450. The fourth suture construct 460 can include a collapsible tube 462 that is formed over a suture 464. The suture 464 can include a passage portion 466 from which extends a first terminal suture end 468 and a second terminal suture end 470. Therefore, the fourth suture construct 460 can also be used to form an anchoring mass by drawing the terminal suture ends 468 and 470 as discussed above.

The augment or replacement construct 350 can be used to interconnect at least a tibia 321, talus 322, navicular 308, and calcaneus 312 by positioning the respective suture constructs, 390, 430, 460, and 364 in bone tunnels formed in the respective bone portions. Without repeating the procedure discussed above for forming the bone tunnels, bone tunnels can be formed in and/or through each of the bone portions similar to a manner as discussed above. Accordingly, a first tunnel 500 can be formed in the tibia 321 and the collapsible tube 394 can be formed into the anchoring mass 394' on an exterior surface of the tibia 321. A portion of the construct 350 can then be tensioned or drawn into the tunnel 500, as discussed above. A second tunnel 520 can be formed through the talus 322 and the collapsible tube 432 can be formed into the anchoring mass 432' on an exterior surface of the talus 322. A portion of the construct 350 can be tensioned into the tunnel 520, as discussed above. A third tunnel 530 can be formed in the calcaneus 312 and an anchor mass 366' can be formed from the collapsible tube 366 and the construct can be tensioned into or onto the calcaneus 312, as discussed above.

A fourth tunnel 540 can be formed into the interior talus or, alternatively, into the navicular 308 (shown in phantom at 540'). It is understood, however, that if the alternative tunnel 540' is formed in the navicular 308 the tunnel 540 may also be formed in an anterior portion of the talus 322 to allow connection of the navicular 308 and the talus 322. The suture construct can be similar to the anchor 120, illustrated in FIG. 2B, to allow for interconnection with a tunnel formed in the anterior portion of the talus 322. Accordingly, it is understood that the construct 350 can be provided to interconnect a plurality of bone portions of the foot 300 including interconnection with a leg bone portion, such as the tibia 321. Moreover, it is understood that the suture constructs can be provided in various configurations to allow for fixing of the ligament or tendon construct 350 to the respective bone portions.

It is understood that the various embodiments of the ligament constructs including the eyelets discussed above can be formed in substantially similar manner and interchanged for various purposes. Moreover, a selected eyelet can be formed in an appropriate manner for selected procedures, as is understood by one skilled in the art. Moreover, forming the eyelets in various manners can be used for productions, efficiencies and/or costs and specific procedures.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and may be used in a selected embodiment, even if not specifically shown or described. The same may also be varied in many ways. Such variations are not to be regarded as a departure from the disclosure, and all such modifications are intended to be included within the scope of the disclosure. The terminology used herein is for the purpose of describing particular example embodiments only and is not intended to be limiting. As used herein, the singular forms "a," "an," and "the" may be intended to include the plural forms as well, unless the context clearly indicates otherwise.

What is claimed is:

1. A method of augmenting a ligament, comprising:
    forming a first bore in a first bone, wherein forming the first bore in the first bone includes forming the first bore in a navicular bone;
    forming a second bore in a second bone, wherein forming the second bore in the second bone includes forming the second bore in a calcaneus bone, wherein the second bone is separate from the first bone and naturally connected with a natural ligament;
    positioning a first anchoring mass relative to the first bone via the first bore;
    positioning a second anchoring mass relative to the second bone via the second bore; and
    tensioning a ligament construct between the first anchoring mass and the second anchoring mass anchor.

2. The method of claim 1, wherein positioning the first anchoring mass relative to the first bone via the first bore includes passing a first anchor through the first bone and positioning the first anchor on an exterior surface of the first bone opposite an insertion position of the ligament construct.

3. The method of claim 2, further comprising:
    applying a tensile load to the first anchor after passing the first anchor through the first bore, including applying the tensile load to a portion of a suture construct to form the first anchoring mass with the first anchor having a locking profile engaging the exterior surface of the first bone, wherein applying the tensile load collapses the first anchor from a first profile to a second profile having a larger diameter to form the anchoring mass.

4. The method of claim 1, wherein positioning the first anchoring mass relative to the first bone via the first bore includes passing a first anchor into the first bore and into the first bone and positioning the first anchor on an exterior surface of the first bone away from an insertion position of the ligament construct.

5. The method of claim 4, further comprising:
applying a tensile load to the first anchor after passing the first anchor into the first bore, including applying the tensile load to a portion of a suture construct to form the first anchoring mass with the first anchor having a locking profile engaging the interior of the first bone, wherein applying the tensile load collapses the first anchor from a first profile to a second profile having a larger diameter to form the first anchoring mass.

6. The method of claim 1, wherein tensioning the ligament construct includes applying tension to a first and a second end of a suture portion;
wherein the suture portion is interconnected with the ligament construct and at least one of a first anchor and a second anchor;
wherein the suture portion has a passage portion that defines a through-passage and the suture portion is a continuous loop, wherein the first end is passed through a first aperture defined by the suture into the through-passage of the passage portion defined by the suture and out a second aperture defined by the suture so as to place the first end outside of the passage portion and form a first suture loop and the second end of the suture is passed through a third aperture into the through-passage of the passage portion and out a fourth aperture so as to place the second end outside of the passage portion to form a second suture loop.

7. The method of claim 1, wherein forming the first bore in the first bone and forming the second bore in the second bone includes, separately:
drilling a first through bore through a proximal cortical bone layer and a distal cortical bone layer with a first diameter drill;
over drilling a second bore through the proximal cortical bone layer and short of the distal cortical bone layer;
wherein each of the first bore and the second bore define an internal shoulder.

8. The method of claim 1, further comprising:
connecting the ligament construct with at least a portion of the ligament configured to interconnect the first bone and the second bone.

9. The method of claim 1, further comprising:
positioning a third anchoring relative to a third bone; and
tensioning the ligament construct relative to each of the first bone, the second bone, and the third bone;
wherein all of the first bone, the second bone, and the third bone are within a foot.

10. The method of claim 1, further comprising:
positioning a fourth anchoring relative to the third bone or a fourth bone; and
tensioning the ligament construct relative to each of the first bone, the second bone, the third bone, and the fourth bone;
wherein all of the first bone, the second bone, the third bone, and the fourth bone are within a foot or articulate with the foot;
wherein positioning the fourth anchoring may be in the third bone.

11. The method of claim 1, forming the first bore in the first bone and forming the second bore in the second bone includes, separately:
forming each of the first bore and the second bore to define an internal shoulder.

12. A method of augmenting a ligament, comprising:
forming a first bore in a tibia bone;
forming a second bore in a calcaneus bone, wherein the calcaneus bone is separate from the tibia bone;
providing a ligament construct connected to a first suture construct and a second suture construct, each of the first suture and the second suture having a passage portion that defines a through-passage and at least one suture loop relative to the passage portion and a first end and a second end;
providing a first collapsible soft anchor connected to the first suture construct;
providing a second collapsible soft anchor connected to second suture construct;
positioning the first collapsible soft anchor tube relative to the tibia bone via the first bore;
positioning a second collapsible soft anchor relative to the calcaneus bone via the second bore;
applying a first force to the first collapsible soft anchor with the first suture construct to form a first anchoring mass with the first collapsible soft anchor;
applying a second force to the second collapsible soft anchor with the second suture construct to form a second anchoring mass with the second collapsible soft anchor; and
tensioning the ligament construct between the first anchoring mass and the second anchoring mass.

13. The method of claim 12, wherein positioning the first collapsible soft anchor relative to the tibia bone via the first bore and positioning the second collapsible soft anchor relative to the calcaneus bone via the second bore includes passing the respective first collapsible soft anchor and the second collapsible soft anchor through the respective first bore and second bore to place the first collapsible soft anchor on an exterior surface of the tibia and to place the second collapsible soft anchor on an exterior surface of the calcaneus.

14. The method of claim 12, wherein tensioning the ligament includes applying a force to the first end and the second end of the first suture construct after the first anchoring mass is formed to at least draw the ligament construct towards the tibia bone.

15. The method of claim 12, wherein tensioning the ligament includes applying a force to the first end and the second end of the second suture construct after the second anchoring mass is formed to at least draw the ligament construct towards the calcaneus bone.

16. The method of claim 12, wherein providing a ligament construct connected to a first suture construct and a second suture construct includes providing an elongated construct having a first terminal end folded and attached centrally of the first terminal end to form a first eyelet through which the first suture construct is positioned and a second terminal end folded and attached centrally of the second terminal end to form a second eyelet through which the second suture construct is positioned.

17. The method of claim 16, further comprising:
providing the ligament construct formed of a woven polymer material.

18. The method of claim 12, wherein providing a ligament construct connected to a first suture construct and a second suture construct includes providing an elongated construct having a first bore formed through a first end through which the first suture construct is positioned and a second bore formed through a second end through which the second suture construct is positioned.

19. The method of claim 12, further comprising:
forming a third bore in a calcaneous;
forming a fourth bore in the calcaneous;
positioning a third collapsible soft anchor relative to the calcaneous bone via the third bore; and
positioning a fourth collapsible soft anchor relative to the calcaneous bone via the fourth bore.

20. A method of augmenting a ligament, comprising:
forming a ligament construct extending from a first terminal end to a second terminal end;
forming a first passage near the first terminal end of the ligament construct;
forming a second passage near the second terminal end of the ligament construct;
connecting a first suture construct to the ligament construct through the first passage;
connecting a second suture construct to the ligament construct through the second passage;
providing each of the first suture construct and the second suture construct having a passage portion that defines a through-passage, where a first end of each suture is passed into the through-passage through a first aperture to form a first loop and exits the through-passage through a second aperture and a second end of each suture is passed into the through-passage through a third aperture to form a second loop and exits the through-passage through a fourth aperture; and
coupling a first soft anchor to the first suture construct and a second soil anchor to the second suture construct.

21. The method of claim 20, wherein forming the first passage near the first terminal end of the ligament construct includes folding the first terminal end inwards to a first position towards a center of the ligament construct and fixing the first terminal end at the first position; and
wherein forming the second passage near the second terminal end of the ligament construct includes folding the second terminal end inwards to a second position towards the center of the ligament construct and fixing the second terminal end at the second position.

22. The method of claim 20, wherein forming the first passage near the first terminal end of the ligament construct and forming the second passage near the second terminal end of the ligament construct includes forming a through-bore through the ligament construct from a first side to a second side.

23. The method of claim 20, where coupling the first soil anchor to the first suture construct includes coupling a first collapsible tube about the first suture construct and the second soft anchor to the second suture construct includes coupling a second collapsible tube about the second suture construct.

24. The method of claim 23, further comprising:
providing the first collapsible tube to collapse and the second collapsible tube to collapse when a tensile force is applied by the respective first suture or second suture.

25. The method of claim 20, wherein forming the ligament construct extending from the first terminal end to the second terminal end includes forming a first arm and a second atm to extend near the second end transverse to a longitudinal axis of the ligament construct defined between the first terminal end to the second terminal end.

\* \* \* \* \*

UNITED STATES PATENT AND TRADEMARK OFFICE
CERTIFICATE OF CORRECTION

PATENT NO. : 9,918,826 B2  
APPLICATION NO. : 14/095614  
DATED : March 20, 2018  
INVENTOR(S) : Berelsman et al.

Page 1 of 2

It is certified that error appears in the above-identified patent and that said Letters Patent is hereby corrected as shown below:

On the Title Page

In item (57), in "Abstract", in Column 2, Line 3, delete "resorbtion." and insert --resorption.-- therefor On page 17, in Column 1, under "Other Publications", Line 6, delete ""Bio-lntrafix" and insert --"Bio-Intrafix-- therefor On page 22, in Column 2, under "Other Publications", Line 27, delete "13/791 014," and insert --13/791,014,-- therefor On page 23, in Column 2, under "Other Publications", Line 7, delete "Requiremnt" and insert --Requirement-- therefor On page 23, in Column 2, under "Other Publications", Line 9, delete "Dec. 24, 2017"," and insert --Dec. 04, 2017",-- therefor On page 23, in Column 2, under "Other Publications", Line 12, delete "4/983,747," and insert --14/983,747,-- therefor In the Claims In Column 15, Line 9, in Claim 19, delete "calcaneous;" and insert --calcaneus;-- therefor In Column 15, Line 10, in Claim 19, delete "calcaneous;" and insert --calcaneus;-- therefor In Column 15, Line 12, in Claim 19, delete "calcaneous" and insert --calcaneus-- therefor In Column 15, Line 14, in Claim 19, delete "calcaneous" and insert --calcaneus-- therefor In Column 16, Line 2, in Claim 20, delete "soil" and insert --soft-- therefor Signed and Sealed this  
Twenty-sixth Day of March, 2019

Andrei Iancu  
*Director of the United States Patent and Trademark Office*

CERTIFICATE OF CORRECTION (continued)
U.S. Pat. No. 9,918,826 B2

In Column 16, Line 18, in Claim 23, delete "soil" and insert --soft-- therefor

In Column 16, Line 31, in Claim 25, delete "atm" and insert --arm-- therefor